United States Patent
Bassarab et al.

(10) Patent No.: US 7,611,709 B2
(45) Date of Patent: *Nov. 3, 2009

(54) 1,4 O-LINKED SACCHAROSE DERIVATIVES FOR STABILIZATION OF ANTIBODIES OR ANTIBODY DERIVATIVES

(75) Inventors: Stefan Bassarab, Biberach (DE); Karoline Bechtold-Peters, Biberach (DE); Richard Fuhrherr, Nuremberg (DE); Wolfgang Friess, Iffeldorf (DE); Patrick Garidel, Norderstedt (DE); Torsten Schultz-Fademrecht, Biberach (DE)

(73) Assignee: Boehringer Ingelheim Pharma GmbH and Co. KG, Ingelheim am Rhein (DE)

( * ) Notice: Subject to any disclaimer, the term of this patent is extended or adjusted under 35 U.S.C. 154(b) by 338 days.

This patent is subject to a terminal disclaimer.

(21) Appl. No.: 11/120,300

(22) Filed: May 2, 2005

(65) Prior Publication Data

US 2005/0255119 A1    Nov. 17, 2005

Related U.S. Application Data

(60) Provisional application No. 60/572,224, filed on May 18, 2004.

(30) Foreign Application Priority Data

May 10, 2004    (DE) ................ 10 2004 022 927

(51) Int. Cl.
  *A61K 39/395*    (2006.01)
  *A61K 9/14*    (2006.01)
  *C07K 16/00*    (2006.01)
(52) U.S. Cl. .............. 424/177.1; 424/489; 424/499; 530/390.5
(58) Field of Classification Search .............. None
  See application file for complete search history.

(56) References Cited

U.S. PATENT DOCUMENTS

| | | | |
|---|---|---|---|
| 3,634,582 A | 1/1972 | Hartley et al. | |
| 3,894,146 A | 7/1975 | Tsuyama | |
| 3,906,950 A | 9/1975 | Cocozza | |
| 4,013,075 A | 3/1977 | Cocozza | |
| 4,570,630 A | 2/1986 | Elliott et al. | |
| 4,811,731 A | 3/1989 | Newell et al. | |
| 5,035,237 A | 7/1991 | Newall et al. | |
| 5,296,473 A | 3/1994 | Hara et al. | |
| 5,320,094 A | 6/1994 | Laube et al. | |
| 5,458,135 A | 10/1995 | Patton et al. | |
| 5,489,577 A | 2/1996 | Ikeda et al. | |
| 5,505,945 A * | 4/1996 | Gristina et al. ........... | 424/164.1 |
| 5,522,385 A | 6/1996 | Lloyd et al. | |
| 5,626,874 A | 5/1997 | Conte et al. | |
| 5,672,581 A | 9/1997 | Rubsamen et al. | |
| 5,753,469 A * | 5/1998 | Nakada et al. .............. | 435/99 |
| 5,785,049 A | 7/1998 | Smith et al. | |
| 5,922,324 A | 7/1999 | Aga et al. | |
| 5,947,118 A | 9/1999 | Hochrainer et al. | |
| 5,972,388 A | 10/1999 | Sakon et al. | |
| 6,453,795 B1 | 9/2002 | Eicher et al. | |
| 2003/0059511 A1 | 3/2003 | Ishii | |
| 2005/0191246 A1 | 9/2005 | Bechtold-Peters et al. | |
| 2005/0250704 A1 | 11/2005 | Bassarab et al. | |
| 2005/0250705 A1 | 11/2005 | Bassarab et al. | |
| 2005/0255119 A1 * | 11/2005 | Bassarab et al. ......... | 424/178.1 |
| 2006/0008574 A1 | 1/2006 | Begli et al. | |
| 2007/0298116 A1 | 12/2007 | Bechtold-Peters et al. | |
| 2008/0089849 A1 | 4/2008 | Schultz-Fademrecht et al. | |

FOREIGN PATENT DOCUMENTS

| | | | |
|---|---|---|---|
| CA | 2273241 | * | 7/1998 |
| CA | 2273277 | | 7/1998 |
| CA | 2297174 A1 | | 2/1999 |
| CA | 2565019 A1 | | 12/2005 |
| DE | 19732351 | | 2/1999 |
| DE | 19953727 A1 | | 5/2001 |
| EP | 129985 A1 | | 1/1985 |
| EP | 237507 A1 | | 9/1987 |
| EP | 467172 A1 | | 1/1992 |
| EP | 0630651 A2 | | 12/1994 |
| EP | 00630651 A2 | | 12/1994 |
| EP | 0739986 | | 10/1996 |
| EP | 0745382 A1 | | 12/1996 |

(Continued)

OTHER PUBLICATIONS

G. Xie, et al., "The thermodynamic mechanism of protein stabilization by trehalose". Biophysical Chemistry, vol. 64, No. 1, 1997, pp. 25-43.

(Continued)

*Primary Examiner*—David A Saunders
(74) *Attorney, Agent, or Firm*—Michael P. Morris; Mary-Ellen M. Devlin; Anthony P. Bottino

(57) ABSTRACT

Disclosed are applications of oligosaccharides/oligosaccharide mixtures for the production and stabilization of pharmaceutical compositions, chiefly powders, that contain antibodies or antibody derivatives as pharmaceutical active substance. The production of powders is accomplished through spray drying or freeze drying. Also disclosed are the corresponding antibody-containing powders as well as processes for their production.

43 Claims, 14 Drawing Sheets

FOREIGN PATENT DOCUMENTS

| | | |
|---|---|---|
| EP | 0911037 A1 | 4/1999 |
| EP | 0974358 A2 | 1/2000 |
| EP | 1174148 A1 | 1/2002 |
| EP | 1223175 A1 | 7/2002 |
| WO | 89/11297 A1 | 11/1989 |
| WO | 90/13328 A1 | 11/1990 |
| WO | 91/14468 A1 | 10/1991 |
| WO | 94/07607 A1 | 4/1994 |
| WO | 94/28958 A1 | 12/1994 |
| WO | 95/31479 A1 | 11/1995 |
| WO | 96/09814 A1 | 4/1996 |
| WO | 96/32096 A1 | 10/1996 |
| WO | 96/32149 A1 | 10/1996 |
| WO | 97/04801 A1 | 2/1997 |
| WO | 97/12683 A1 | 4/1997 |
| WO | 97/12687 A1 | 4/1997 |
| WO | 97/20590 A1 | 6/1997 |
| WO | 97/41031 A1 | 11/1997 |
| WO | 97/41833 A1 | 11/1997 |
| WO | 97/44013 A1 | 11/1997 |
| WO | 98/16205 A2 | 4/1998 |
| WO | 98/31346 A1 | 7/1998 |
| WO | WO 9927071 A1 | 6/1999 |
| WO | 99/66903 A2 | 12/1999 |
| WO | WO 00/09164 * | 2/2000 |
| WO | 00/10541 A1 | 3/2000 |
| WO | 01/00263 A2 | 1/2001 |
| WO | 01/13893 A2 | 3/2001 |
| WO | 01/32144 A1 | 10/2001 |
| WO | 02/43750 A2 | 6/2002 |
| WO | WO 03041512 A1 | 5/2003 |
| WO | WO 03/064473 A2 * | 8/2003 |
| WO | WO 03080027 A1 | 10/2003 |
| WO | 2005/112996 A1 | 12/2005 |
| WO | 2005112892 | 12/2005 |
| WO | 2008055951 | 5/2008 |

OTHER PUBLICATIONS

G. Xie, et al., "Mechanism of the stabilization of ribonuclease A by sorbitol: Preferential hydration is greater for the denatured than for the native protein". Protein Science, vol. 6, 1997, pp. 211-221.

S. N. Timasheff. "The control of protein stability and association by weak interactions with water: How do solvents affect these processes?". Annual Rev. Biophysics and Biomolecular Structure, vol. 22, 1993, pp. 67-97.

A. M. Boctor, et al., "Enhancement of the stability of thrombin by polyols: microcalorimetric studies". Journal of Pharmacy and Pharmacology, vol. 44, No. 7, 1992, pp. 600-603.

B. S. Chang, et al., "Stabilization of lyophilized porcine pancreatic elastase". Pharmaceutical Research, vol. 10, No. 10, 1993, pp. 1478-1483.

A. C. Herman, et al., "Characterization, formulation, and stability of neupogen (Filgrastim), a recombinant human granulocyte-colony stimulating factors". Pharmaceutical Biotechnology, vol. 9, 1996, pp. 303-328.

H.K. Chan, et al., "Effects of additives on heat denaturation of rhDNase in solutions". Pharmaceutical Research, vol. 13, No. 5, 1996, pp. 756-761.

J. Zhang, et al., "NMR study of the cold, heat, and pressure unfolding of ribonuclease A". Biochemistry, 1995, vol. 34, No. 27, pp. 8631-8641.

R. L. Remmele, Jr., et al., "Interleukin-1 receptor (IL-1R) liquid formulation development using differential scanning calorimetry". Pharmaceutical Research, vol. 15, No. 2, 1998, pp. 200-208.

Y. F. Maa, et al., "Effect of spray drying and subsequent processing conditions on residual moisture content and physical/biochemical stability of protein inhalation powders". Pharmaceutical Research, Vol. 15, No. 5, 1998, pp. 768-775.

J. Broadhead, et al., "The effect of process and formulation variables on the properties of spray-dried b-galactosidase". Journal Pharm. Pharmacol, 1994, vol. 46, No. 6, pp. 458-467.

M. T. Vidgren, et al., "Comparison of physical and inhalation properties of spray-dried and mechanically micronized disodium cromoglycate". Int. J. Pharmaceutics, vol. 35, 1987, pp. 139-144.

R. W. Niven, et al., "Pulmonary delivery of powders and solutions containing recombinant human granulocyte colony-stimulating factor (rhG-CSF) to the rabbit". Pharmaceutical Research, vol. 11, No. 8, 1994, pp. 1101-1109.

Y. F. Maa, et al., "The effect of operating and formulation variables on the morphology of spray-dried protein particles". Pharmaceutical Development and Technology, vol. 2, No. 3, 1997, pp. 213-223.

H. R. Costantino, et al., "Effect of mannitol crystallization on the stability and aerosol performance of a spray-dried pharmaceutical protein, recombinant humanized anti-IgE monoclonal antibody". Journal of Pharmaceutical Sciences, Vo.87, No. 11, 1998, pp. 1406-1411.

C. Bosquillon, et al., "Influence of formation excipients and physical characteristics of inhalation dry powders on their aerosolization performance". Journal of Controlled Release, vol. 70, No. 3, 2001, pp. 329-339.

J. S. Huston, et al., "Protein engineering of antibody binding sites: recovery of specific activity in an anti-digoxin single-chain Fv analogue produced in *Escherichia Coli*". Proc. Natl. Acad. Sci., USA, vol. 85, 1988, pp. 5879 ff.

O. Perisic, et al., "Crystal structure of a diabody, a bivalent antibody fragment". Structure, vol. 2, 1994, pp. 1217 ff.

S. Z. Hu., et al., "Minibody: a novel engineered anti-carcinoembryonic antigen antibody fragment (single-chain Fv-CH3) which exhibits rapid, high-level targeting of xenografts". Cancer Research, vol. 56, 1996, pp. 3055 ff.

B. Lovejoy, et al. "Crystal structure of a synthetic triple-standard a-Helical bundle". Science, vol. 259, 1993, pp. 1288 ff.

P. Pack, et al., "Tetravalent miniantibodies with high avidity assembling in *Escherichia coli*". Journal Mo. Biol., 1995, 1995, 246, p. 28-34.

P. Pack, et al., "Improved bivalent miniantibodies, with identical avidy as whole antibodies, produced by high cell density fermentation of *Escherichia coli*". Bio/technology, vol. 11, 1993, pp. 1271 ff.

M. Adler, et al., "Stability and surface activity of lactate dehydrogenase in spray-dried trehalone". Journal of Pharmaceutical Sciences, vol. 88, No. 2, 1999, pp. 199-208.

S. N. Timashieff, et al., "Control of protein stability and reactions by weakly interacting cosolvents: the simplicity of the complicated". Advances in Protein Chemistry, vol. 51, p. 355.

ISR for PCT/EP2005/004807 dated May 5, 2005.

Bauer, et al. Basic Physical-Chemicals Principles for Dosage Forms, Edition 6, Chapter 4, pp. 70-73.

Bauer, et al. Basic Physical-Chemicals Principles for Dosage Forms, Edition 6, Chapter 2, pp. 103-107.

Bauer, et al. Basic Physical-Chemicals Principles for Dosage Forms, Edition 7, Chapter 6, pp. 167-191.

V. Windisch, et al. "Degradation Pathways of Salmon Calcitonin in Aqueous Solutions". Journal of Pharmaceutical Sciences, vol. 86, No. 3, Mar. 1997, pp. 359-364.

K. Masters. Spray Drying Handbook. 4$^{th}$ Edition, Longman Scientific & Technical. Copublished in the US with John Wiley & Sons, Inc., NY. Boehringer Ingelheim Vetmedica GmbH. pp. 1-335, Parts 1-5.

M. Willmann. Dissertation Stabilization of Pharmaceutical Protein Solutions by Vacuum Drying, pp. 14-23.

M. Adler. Dissertation. Chapter 2.3, pp. 11-19.
M. Adler. Dissertation. Chapter 4, pp. 41-56.
M. Adler. Dissertation. Chapter 5.1, pp. 58-70.
M. Adler. Dissertation. Chapter 5.2, pp. 71-83.
M. Adler. Dissertation. Chapter 5.4, pp. 84-102.
M. Adler. Dissertation. Chapter 6.3, pp. 111-123.

D. B. Dix, et al. "Increasing the Physical Stability of a Hydrophobic Protein: RHCNTF". Pharmaceutical Research (Supplement), 1995, Biotec 2074, 12, S-97.

S. M. Chamow, et al., Editors. "Antibody Fusion Proteins". Wiley-Liss Publication. Copyright 1999, pp. 1-316.

"Handbook of Pharmaceutical Excipients". American Pharmaceutical Association & The Pharmaceutical Society of Great Britain. 1986, pp. 153-162, 304-308, 231.

A. A. Kortt, et al., "Single-chain Fv fragments of anti-neuraminidase antibody NC10 containing five-and ten-residue linkers form dimmers and with zero-residue linker a trimer". Protein Engineering, vol. 10, No. 4, 1997, pp. 423-433.

Bauer, et al. Basic Physical-Chemicals Principles for Dosage Forms, Edition 6, Chapter 4, pp. 70-73, 1999.

Bauer, et al. Basic Physical-Chemicals Principles for Dosage Forms, Edition 6, Chapter 2, pp. 103-107, 1999.

Bauer, et al. Basic Physical-Chemicals Principles for Dosage Forms, Edition 7, Chapter 6, pp. 167-191, 2002.

M. Adler. Dissertation, Spray Embedding of Proteins In Structure-Forming Agents: Stability and Surface Analysis, Chapter 2.3, Changes in Protein Structure, pp. 11-19, Jul. 23, 1999.

M. Adler. Dissertation, Spray Embedding of Proteins In Structure-Forming Agents: Stability and Surface Analysis, Chapter 4, Materials and Methods, pp. 41-56, Jul. 23, 1999.

M. Adler. Dissertation, Spray Embedding of Proteins In Structure-Forming Agents: Stability and Surface Analysis, Chapter 5.1, Sugars and Sugar Alcohols, pp. 58-70, Jul. 23, 1999.

M. Adler. Dissertation, Spray Embedding of Proteins In Structure-Forming Agents: Stability and Surface Analysis, Chapter 5.2, Amino Acids, pp. 71-83, Jul. 23, 1999.

M. Adler. Dissertation, Spray Embedding of Proteins In Structure-Forming Agents: Stability and Surface Analysis, Chapter 5.4, Spray Drying of Structure Forming Agents, pp. 84-102, Jul. 23, 19993, 1999.

M. Adler. Dissertation, Spray Embedding of Proteins In Structure-Forming Agents: Stability and Surface Analysis, Chapter 6.3, Influence of polysorbate 80 and Lipoid E80 On the Process and Storage Stability of LDH, pp. 111-123, Jul. 23, 1999.

M. Adler; Foreword, Spray Embedding of Proteins In Structure-Forming Agents: Stability and Surface Analysis, Table of Contents & Symbols, indexing sections 4-9 listed above, Jul. 23, 1999.

International Search Report for PCT/EP2005/004806 mailed Aug. 1, 2005 (01-1591).

International Search Report for PCT/EP2005/004808 mailed May 17, 2006 (01-1694).

International Search Report for PCT/EP2005/004807 mailed Oct. 13, 2005. (01-1693).

* cited by examiner

Figure: 1
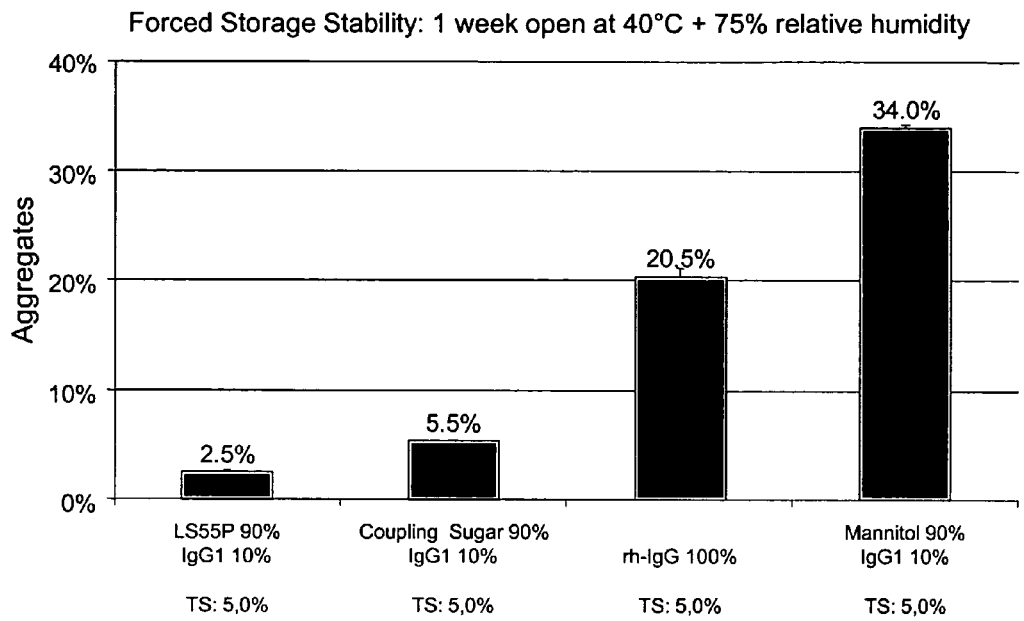
Figure: 2
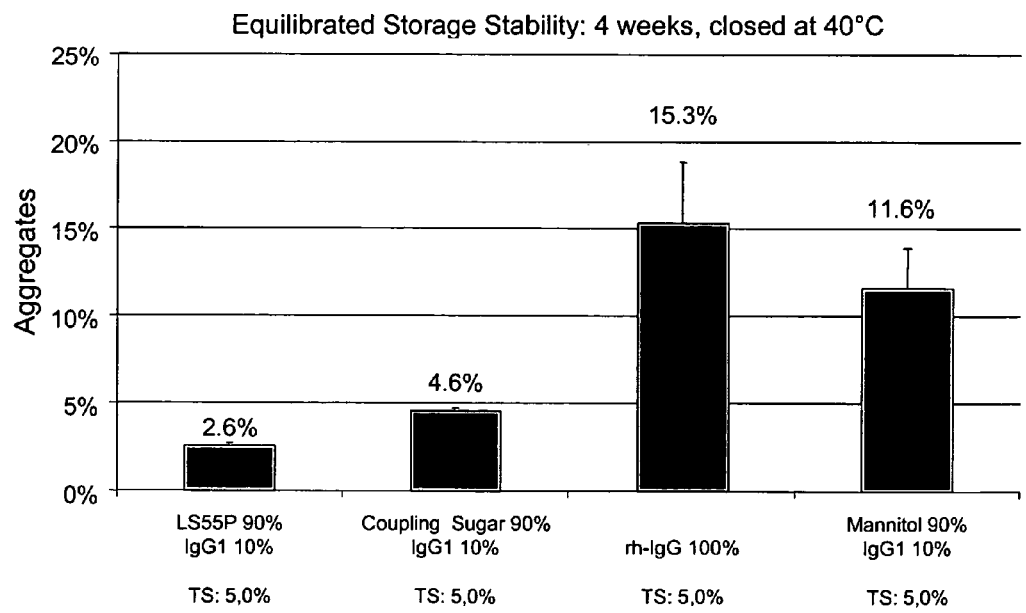

Figure: 3
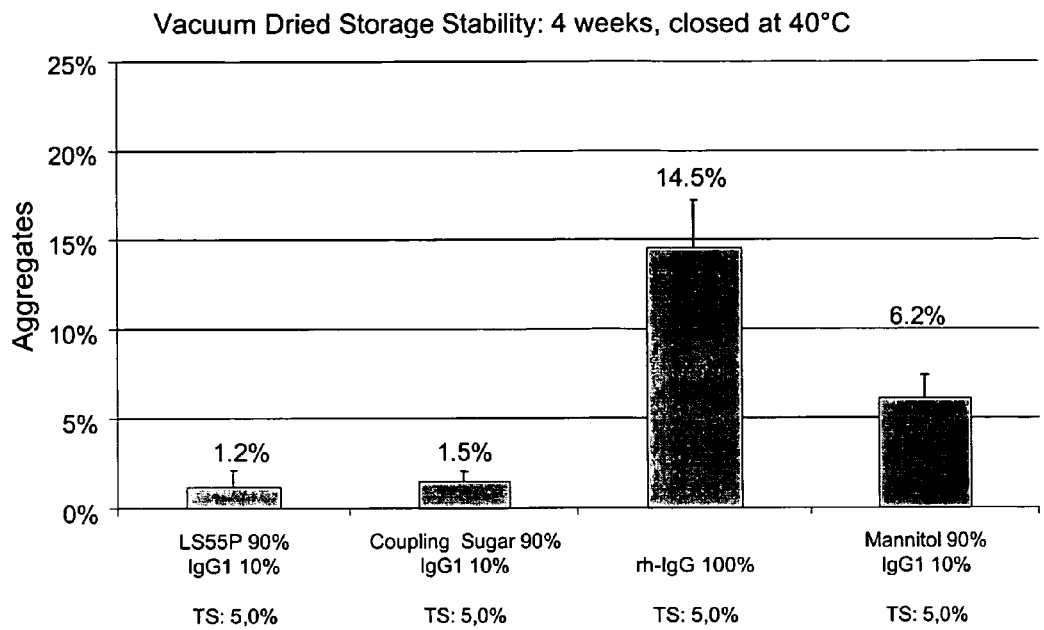
Figure: 4
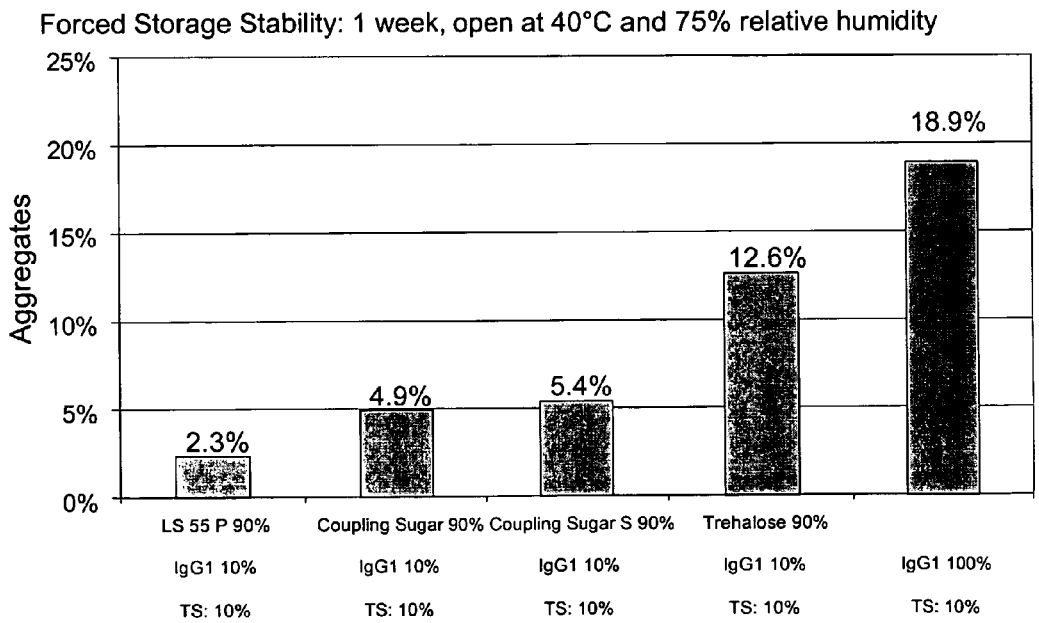

Figure: 5
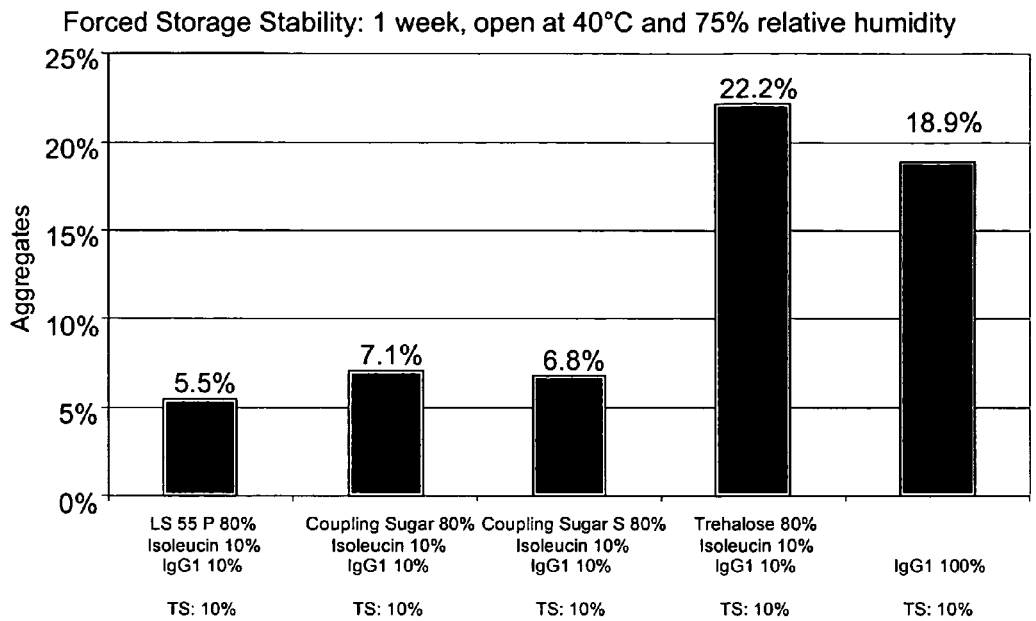
Figure: 6
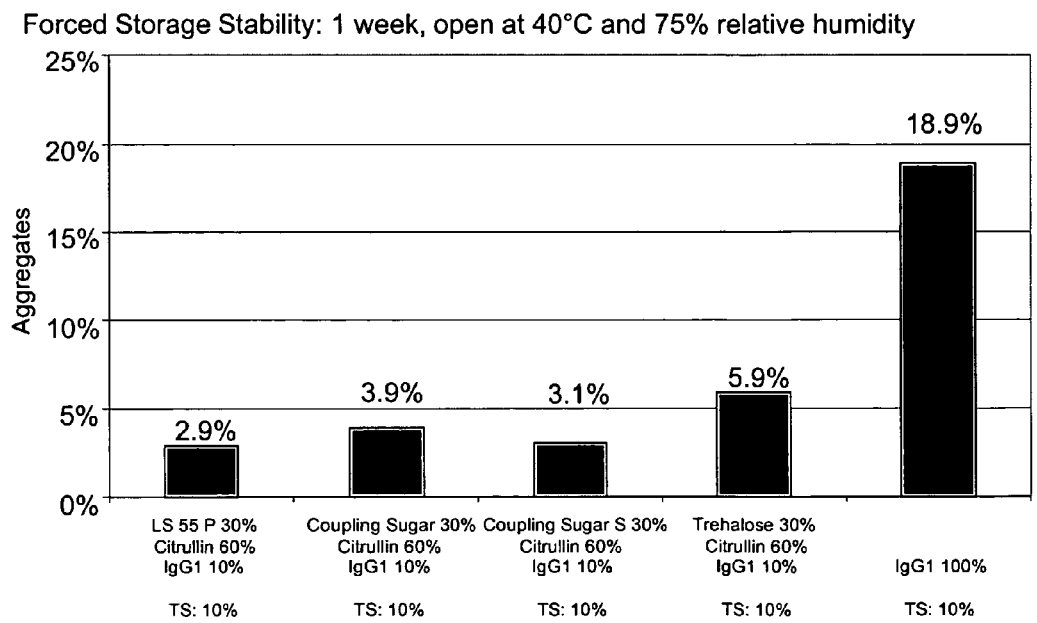

Figure: 7
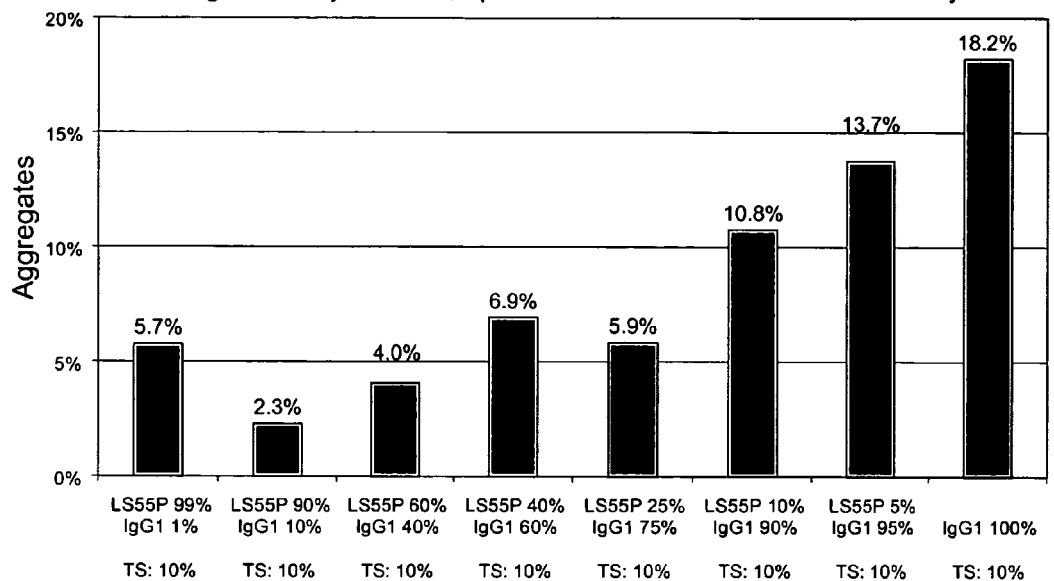
Figure: 8
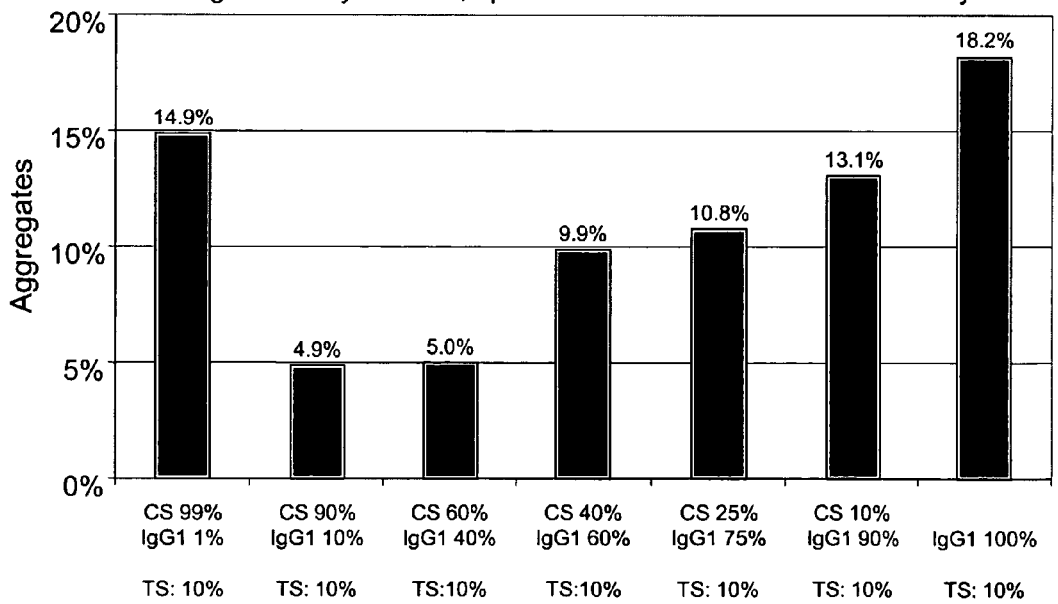

Figure: 9
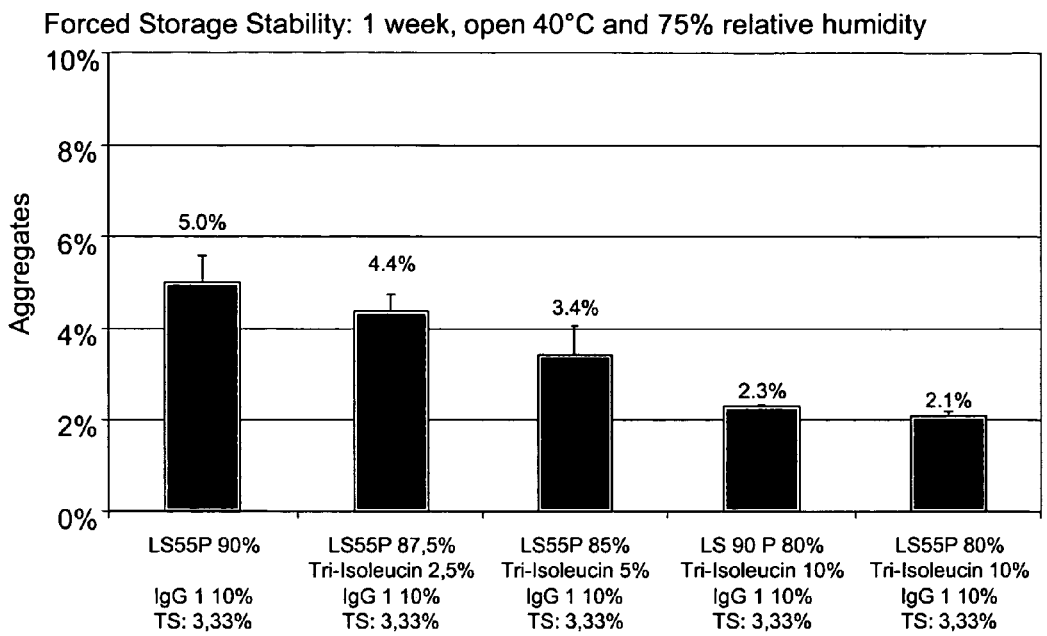
Figure: 10
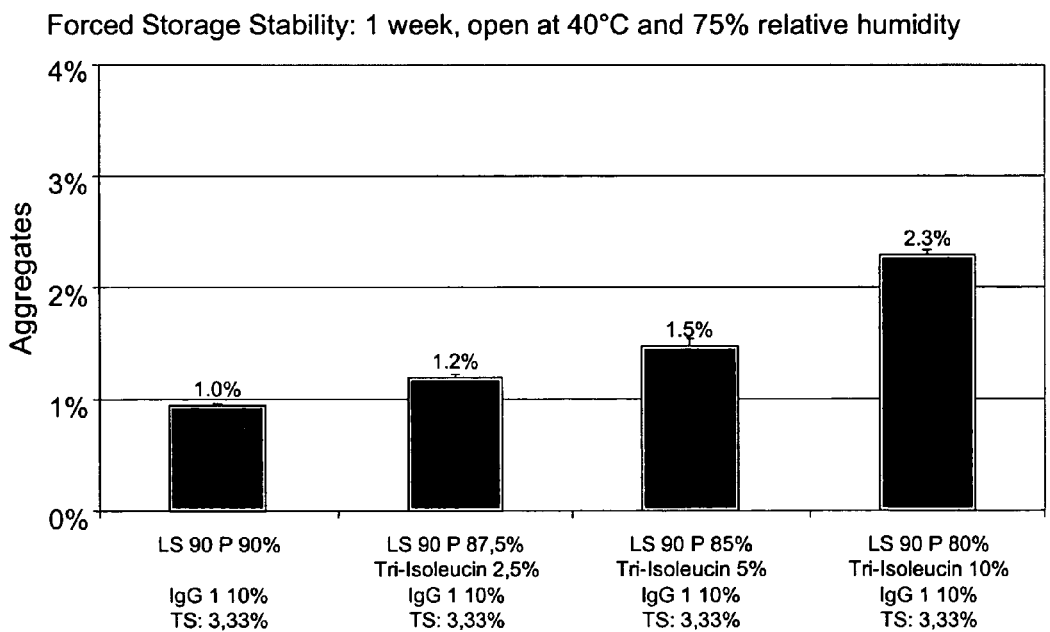

Figure: 11
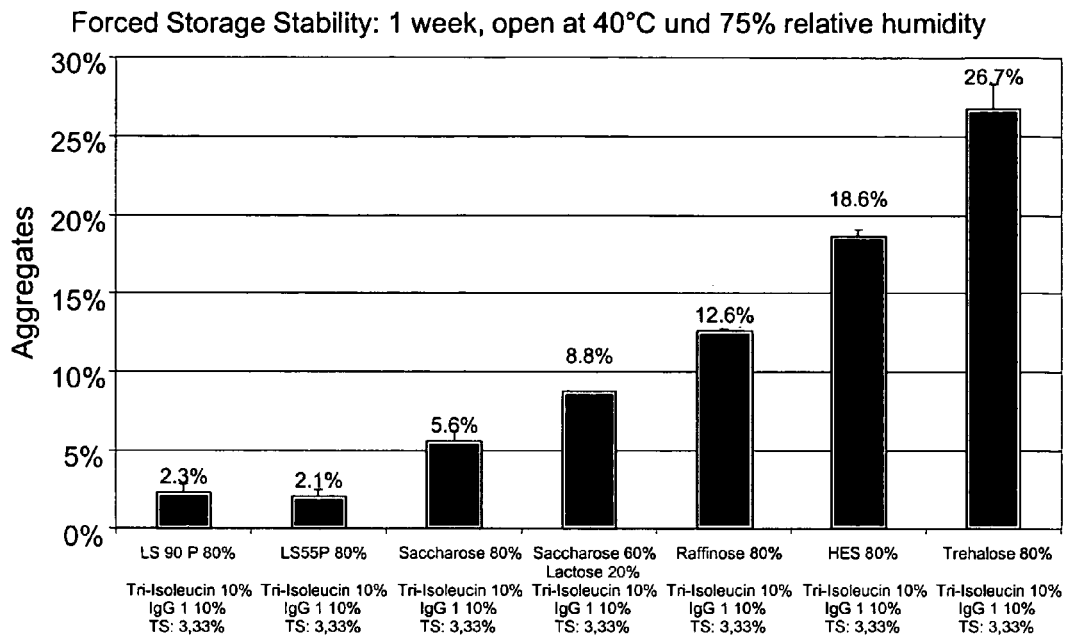
Figure: 12
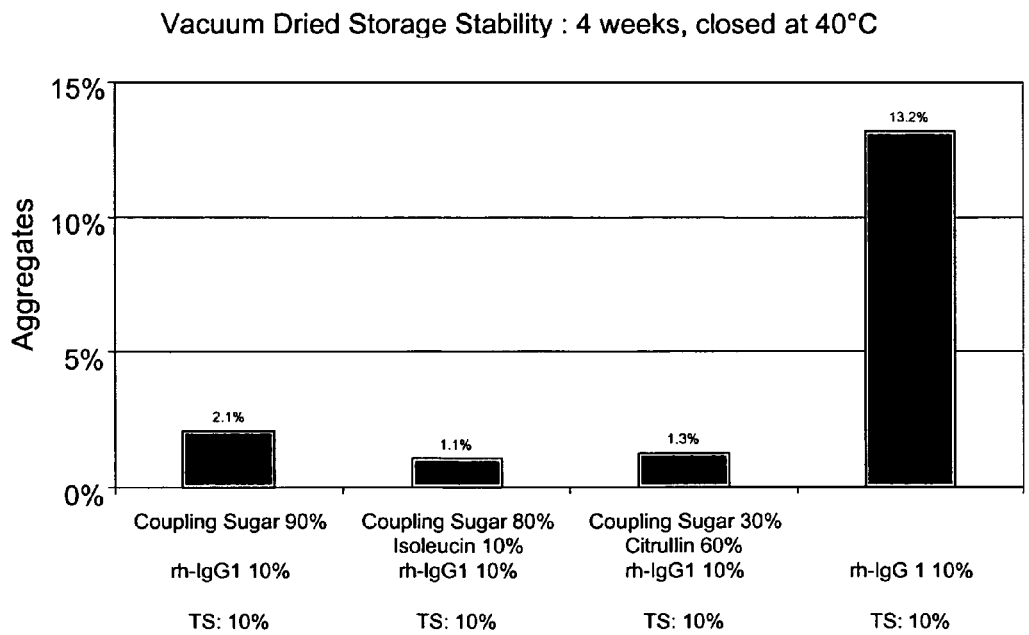

Figure: 13
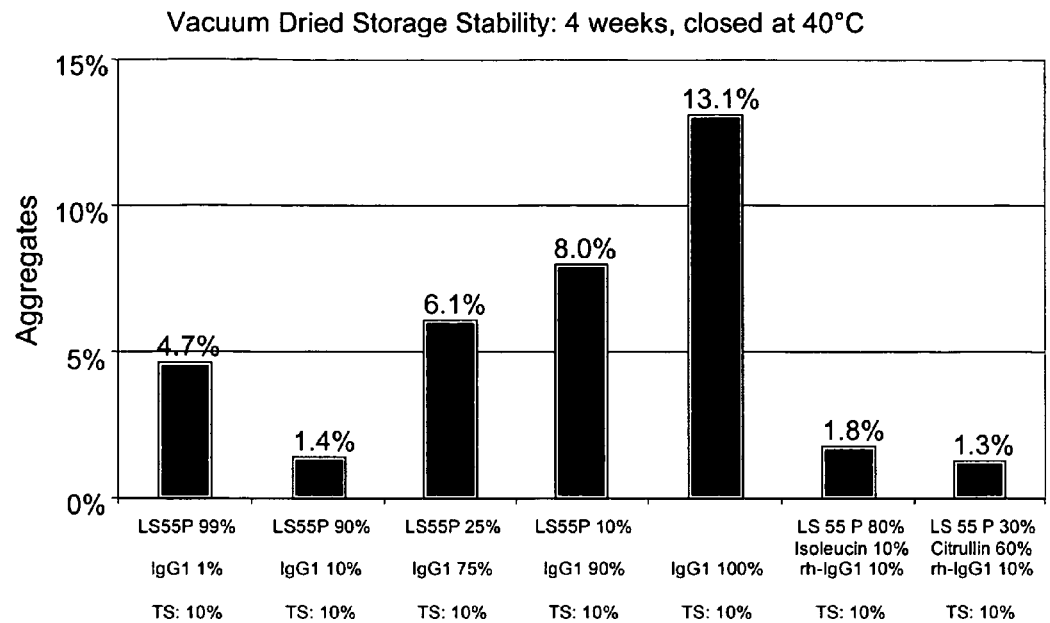
Figure: 14a
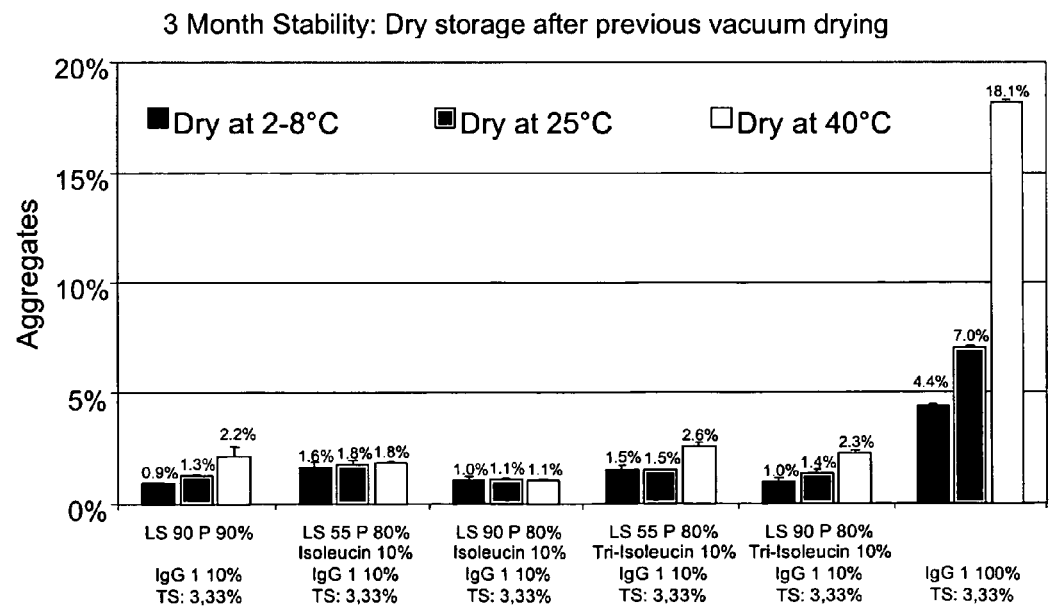

Figure: 14b
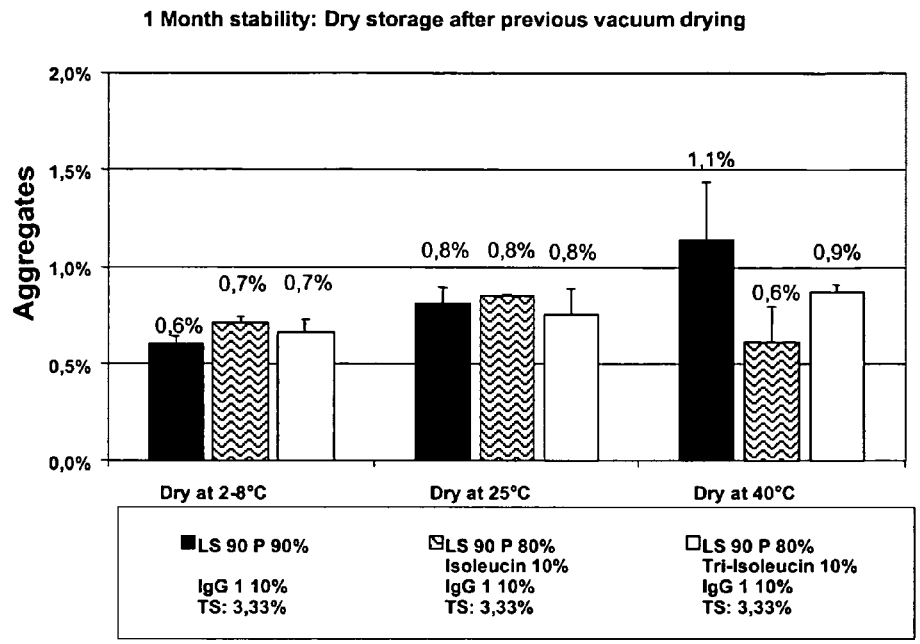
Figure: 15a
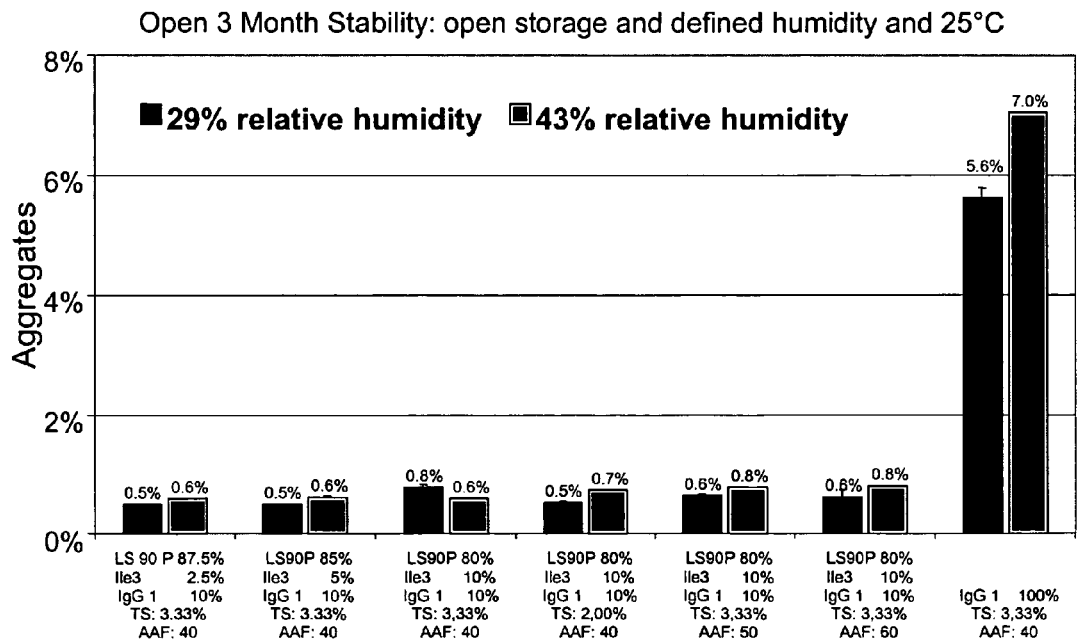

Figure: 15b
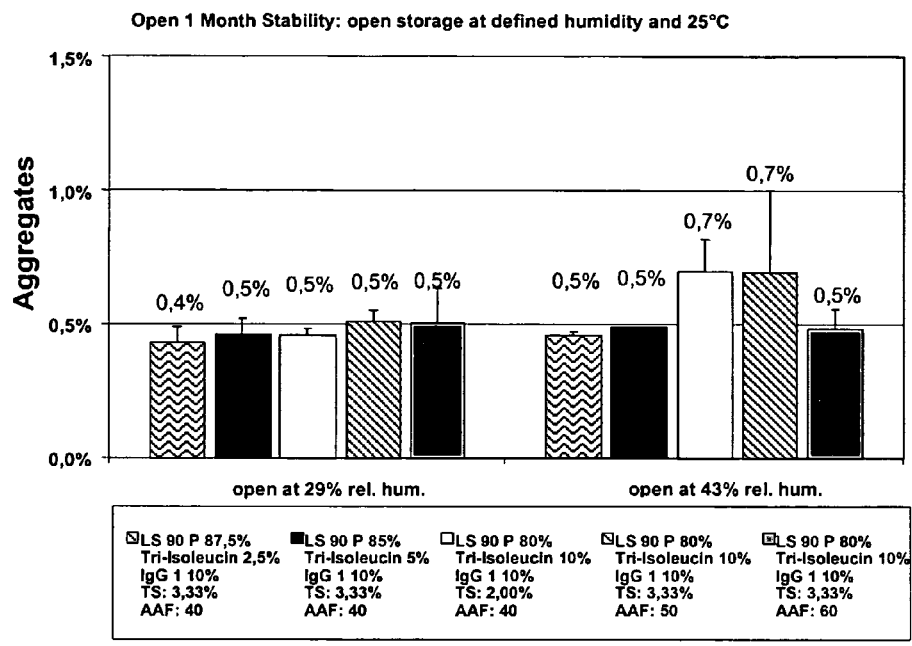
Figure: 16
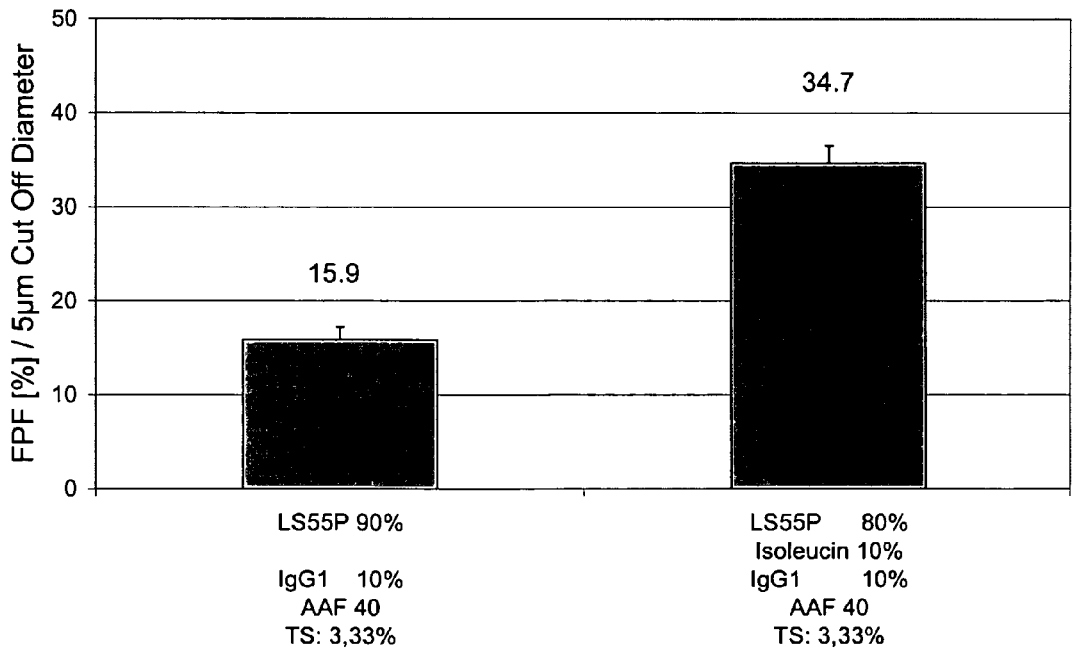

Figure: 17
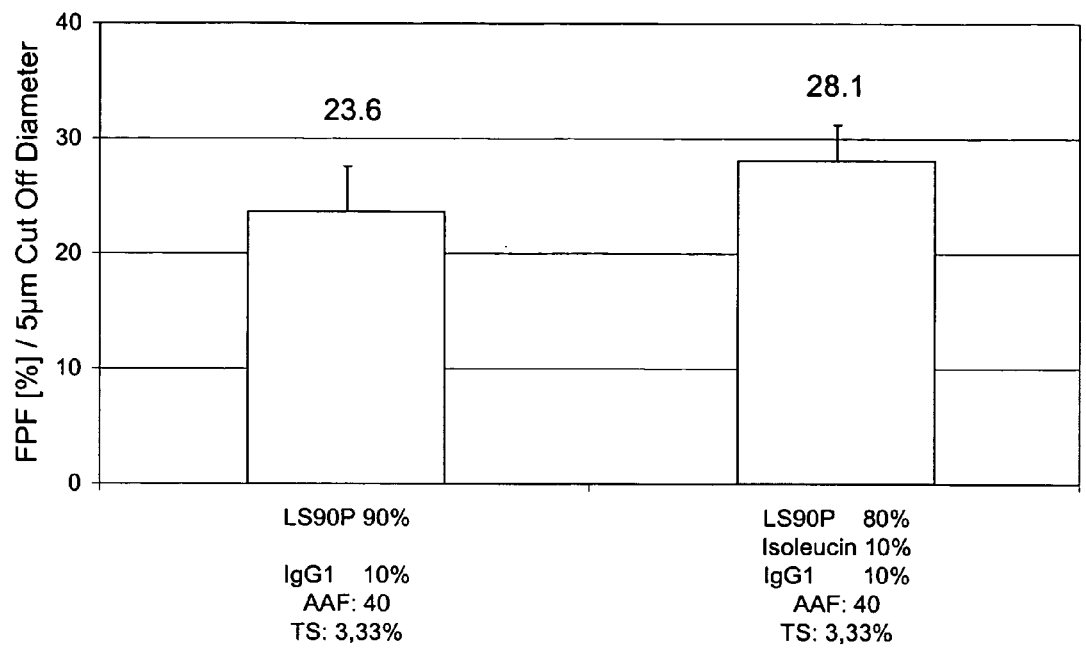
Figure: 18
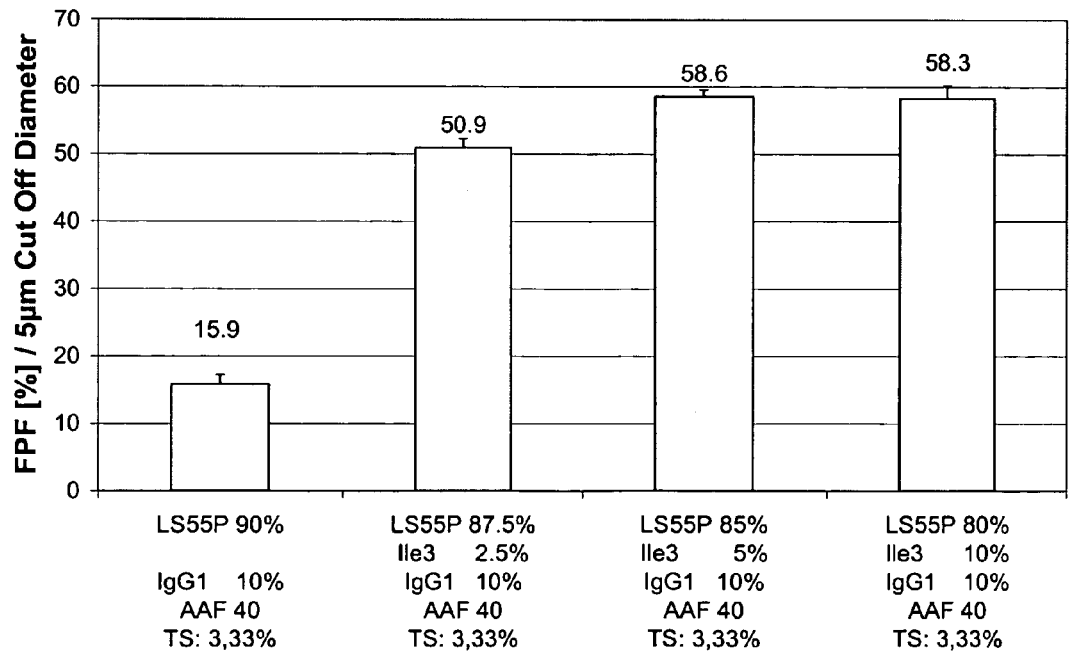

Figure: 19
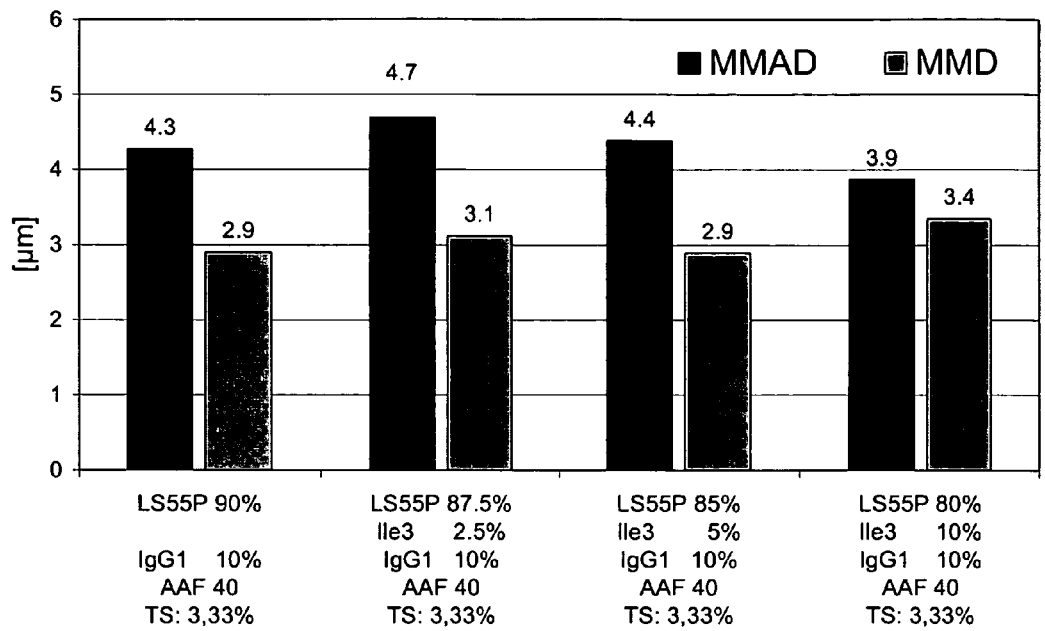
Figure: 20
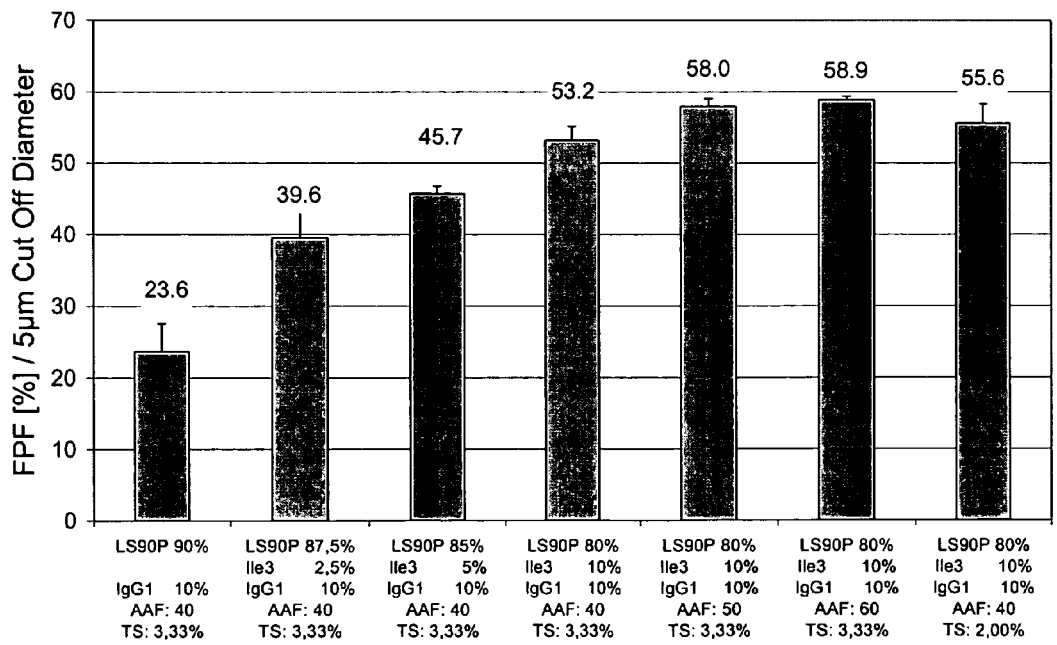

Figure: 21
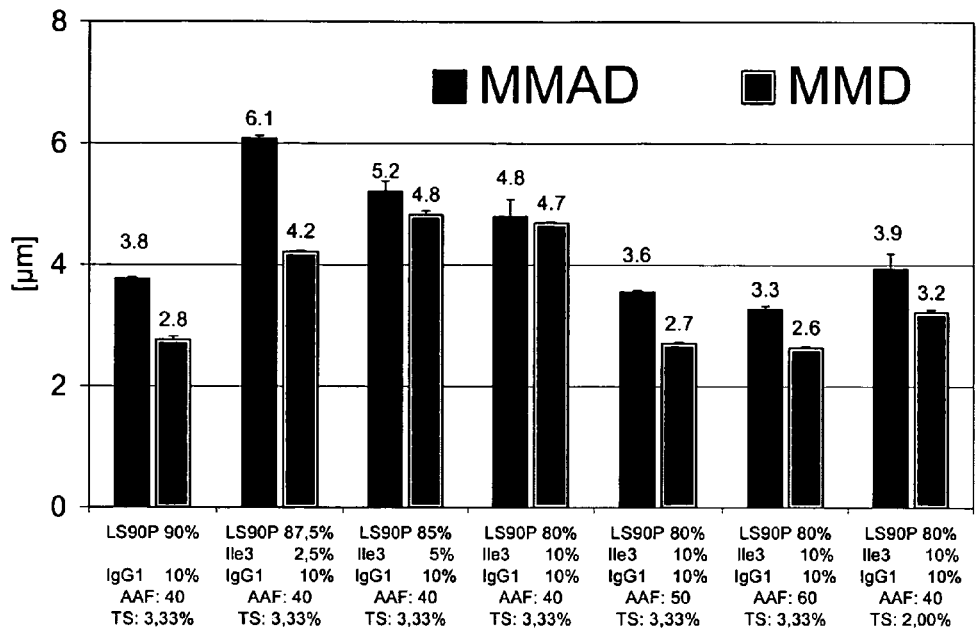
Figure: 22
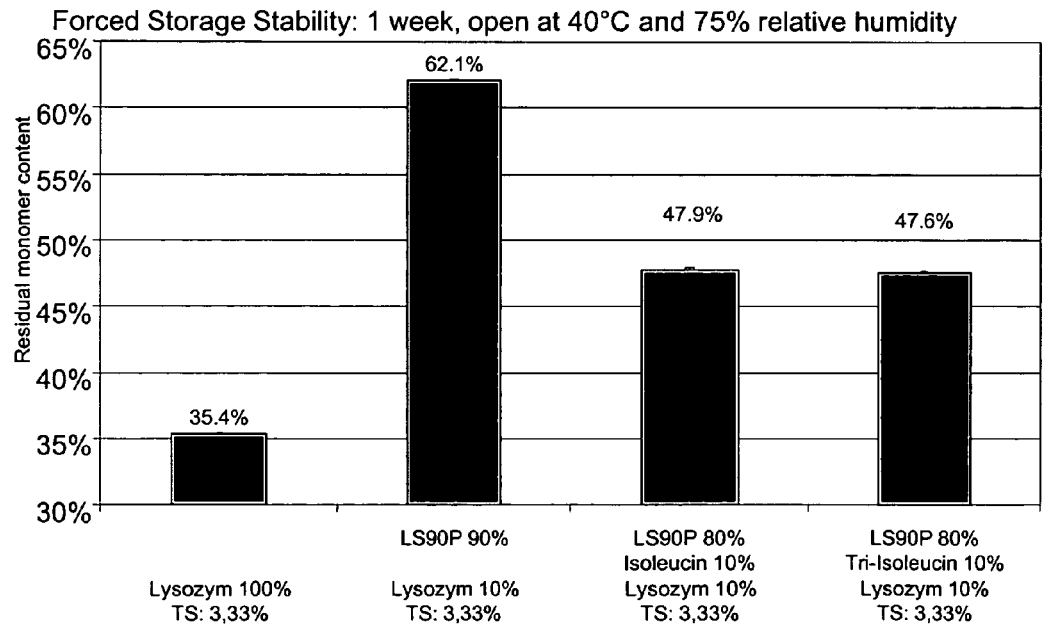

Figure: 23
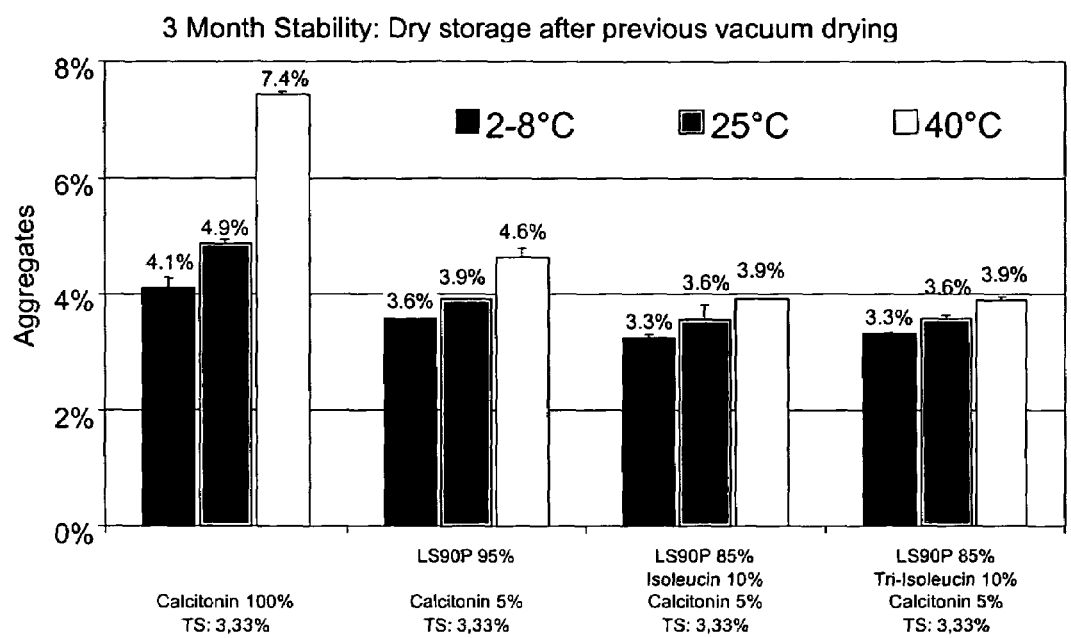

Figure: 24
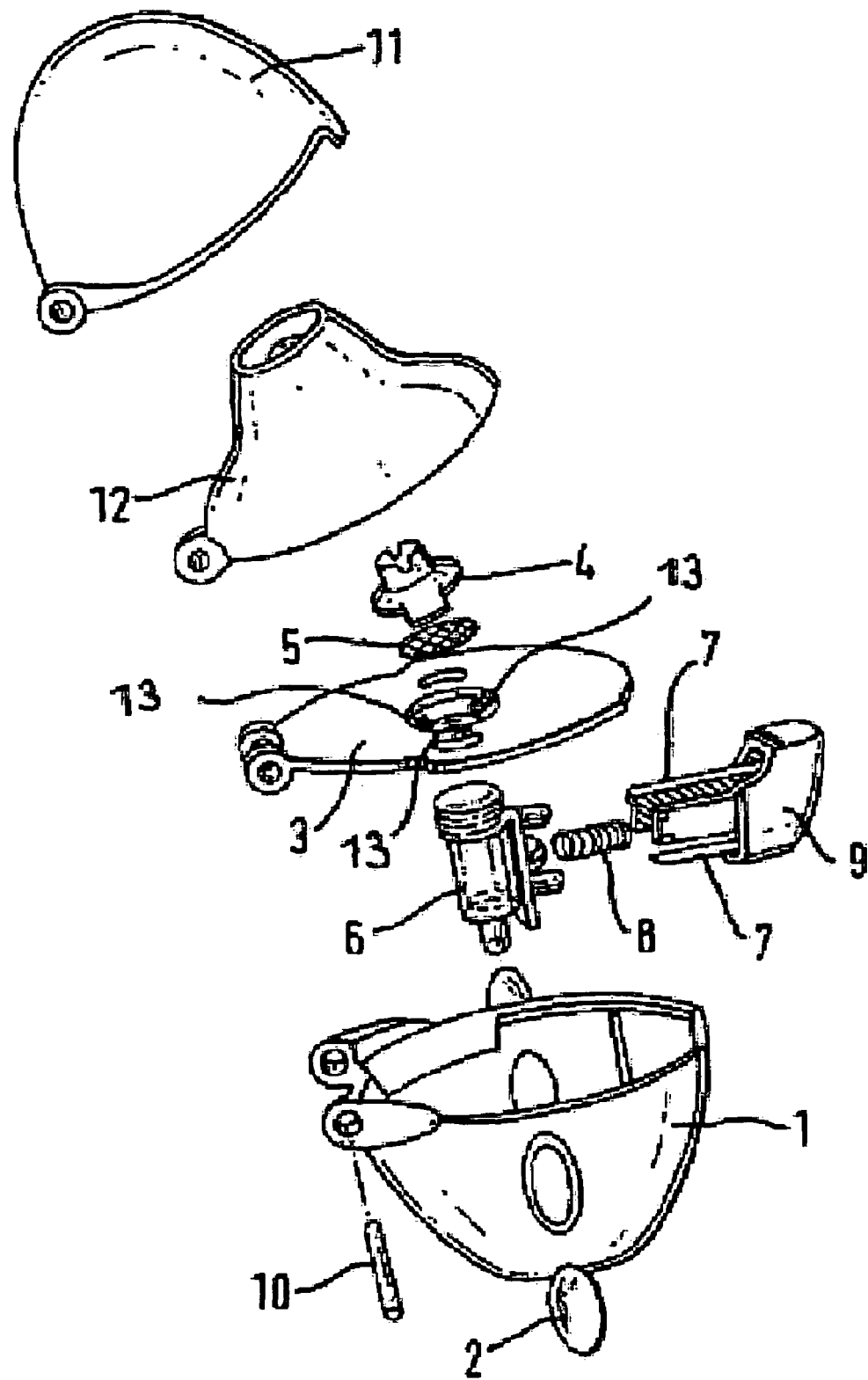

US 7,611,709 B2

1,4 O-LINKED SACCHAROSE DERIVATIVES FOR STABILIZATION OF ANTIBODIES OR ANTIBODY DERIVATIVES

APPLICATION DATA

This application claims benefit to German application no. DE 102004022927.9 filed May 10, 2004 and U.S. provisional application No. 60/572,224 filed May 18, 2004.

INVENTION FIELD

The invention concerns the application of novel oligosaccharides/oligosaccharide mixtures for the production and stabilization of pharmaceutical compositions, chiefly powders, that contain antibodies or antibody derivatives as pharmaceutical active substance. The production of powders is preferably accomplished through spray drying or freeze drying. The present invention particularly concerns corresponding antibody-containing powders as well as processes for their production.

BACKGROUND

Active substances/preparations of active substances formulated in aqueous solutions are to some extent subject to instabilities that may lead to reduced efficacy or bioactivity and elevated toxicity or incompatibilities. This applies to both conventional pharmaceuticals and peptide- or protein-containing active substances. The stability of pharmaceutical active substances can be positively affected through modification of the structure (internal) or through the addition of suitable adjuvants (external).

A conventional process for external stabilization of pharmaceutical active substances is the application of suitable adjuvants. Adjuvants that stabilize active substances can be broadly classified into: sugars and polyols, amino acids, amines, salts, polymers, and tensides.

Sugars and polyols are often used as unspecific stabilizers. Their stabilizing effect on biological active substances is chiefly ascribed to "preferential exclusion" (Xie and Timasheff, 1997, Biophysical Chemistry 64(1-3), 25-43; Xie and Timasheff, 1997, Protein Science, 6(1), 211-221; Timasheff, 1998, Advances in Protein Chemistry, 51, 355-432). During the selection of sugars, reducing sugars are mostly avoided for biological active substances. Saccharose and trehalose as non-reducing sugars are preferably used. Other examples of suitable adjuvants are glucose, sorbitol, glycerol (Boctor and Mehta, 1992, Journal of Pharmacy and Pharmacology, 44 (7), 600-3; Timasheff, 1993, Annual Review of Biophysics and Biomolecular Structure, 22, 67-97; Chang et al., 1993, Pharmaceutical Research, 10(10), 1478-83, and Mannitol (Hermann et al., 1996, Pharmaceutical Biotechnology, 9 (Formulation, Characterization, and Stability of Protein Drugs) 303-328; Chang et al., 1996, Pharmaceutical Research, 13(5), 756-761). Also known is the stabilizing effect that a wide variety of polymers have on pharmaceutical active substances, chiefly proteins, such as e.g. antibodies. Human serum albumin (HAS) frequently used in the past, while in fact featuring very good stabilizing and aggregation-inhibiting properties, has in the meantime been found unsuitable because of its potential contamination with blood-borne pathogens. Among previously known polymers, hydroxypropyl-β-cyclodextrin (HP-β-CD) is especially suitable, since it can also be used parenterally in a completely safe way. Further examples are higher-molecular dextrans (18 to 82 kD), PVP, heparin, type A and B gelatins, and hydroxyethyl starch (HES), heparin, dextran sulphate, polyphosphoric acid, poly-L-glutamic acid, poly-L-lysine.

Alongside sugars and polyols, amino acids can also be used in a stabilizing role or in combination with other adjuvants. Amino acids are chiefly used in the stabilization of proteins. For example, addition of histidine, glycine, sodium aspartate (Na-Asp), glutamate, and lysine hydrochloride (Lys-HCl) inhibits the aggregation of rhKGF in 10 mM sodium phosphate buffer (pH 7.0) together with 5% mannitol (Zhang et al., 1995, Biochemistry, 34 (27), 8631-41). Combination of amino acids and propylene glycol, for example, improves the structural stability of rhCNTF (Dix et al., 1995, Pharmaceutical Research (Supplement), 12, S97). Lysine and arginine enhance the thermal stability of IL-1R (Tm enhancement), whereas glycine and alanine have a destabilizing effect (Remmele et al., 1998, Pharmaceutical Research, 15(2), 200-208).

The stability of pharmaceutical active substances can be moreover enhanced through various drying processes. Drying, however, also mostly proceeds in the presence of adjuvants intended to maintain the stability of active substances and to improve the properties of the dry powder. A decisive factor affecting stabilization through drying is immobilization of the active substance in an amorphous matrix. The amorphous state confers high viscosity with low molecular mobility and low reactivity. Advantageous adjuvants must therefore be able to form an amorphous matrix with an as high as possible glass transition temperature wherein the active substance is embedded. Selection of adjuvants therefore particularly depends on their stabilization capabilities. Other factors, such as the pharmaceutical acceptability of the adjuvant, its influence on particle formation, dispersibility, and fluidity, also play an important role, particularly in respect of spray drying processes.

Spray drying constitutes an especially suitable process for enhancement of the chemical and physical stability of peptide-/protein-containing pharmaceutical active substances (Maa et al., 1998, Pharmaceutical Research, 15(5). 768-775). Spray drying is being increasingly used particularly in the field of pulmonary therapy (U.S. Pat. No. 5,626,874; U.S. Pat. No. 5,972,388; Broadhead et al., 1994, J. Pharm. Pharmacol., 46(6), 458-467), since application in an inhaler in the meantime represents a viable alternative in the treatment of systemic diseases (WO 99/07340). A prerequisite is that the particle size of powders should be in the 1-10 μm range, preferably in the 1-7.5 μm range, so that the particles can penetrate into deeper lung segments and thus into the bloodstream. For example, DE-A-179 22 07 describes the production of corresponding spray drying particles. In the meantime, numerous processes for the production of corresponding powders have been described (WO 95/31479; WO 96/09814; WO 96/32096; WO 96/32149; WO 97/41833; WO 97/44013; WO 98/16205; WO 98/31346; WO 99/66903; WO 00/10541; WO 01/13893; Maa et al., 1998, ibid; Vidgren et al., 1987, Int. J. Pharmaceutics, 35, 139-144; Niven et al., 1994, Pharmaceutical Research, 11(8), 1101-1109).

Also suitable as adjuvants are sugars and their alcohols (e.g. trehalose, lactose, saccharose, or mannitol) as well as various polymers (Maa et al., 1997, Pharm. Development and Technology, 2(3), 213-223; Maa et al., 1998, ibid, Adler, 1998, Dissertation University of Erlangen; Costantino et al., 1998, J. Pharm. Sci, 87(11), 1406-1411). The adjuvants chiefly used, however, have various disadvantages. For example, addition of trehalose and mannitol impairs the fluidity of spray drying formulations (C. Bosquillon et al., 2001, Journal of Controlled Release, 70(3), 329-339). At a content of more than 20 weight percent, mannitol additionally tends to recrystallize (Constantino et al., 1998, ibid), with stabilizing effects dramatically decreasing. Lactose, a frequently used adjuvant, while improving the fluidity of spray drying formulations (C. Bosquillon et al., 2001, ibid), raises problems particularly during the formulation of peptide-/protein-containing active substances, since lactose, because of its reducing property, may engage in destabilizing Maillard reactions with peptides/proteins.

During spray drying of antibodies without addition of stabilizers, dehydration, heat, and shearing regularly lead to unfolding of the native secondary structure and thus to dramatic loss of bioactivity. Previously inward facing hydrophobic fractions of the antibody then revert to facing outwards. This progressively occurs on the hydrophobic interfaces between the water droplets generated during spray drying and ambient air. Antibodies in the aqueous phase moreover accumulate to form dimers or higher-order aggregates. Such aggregation is often irreversible. The high temperature at which the proteins are sprayed further represents a critical parameter. The high energy consumption may lead to destabilization of the peptide bonds and to denaturation of the antibody. Aggregation of spray-dried antibodies further occurs during storage of powders. The residual water content of the powder then exerts a particularly adverse effect. Protein aggregates are characterized by reduced or lacking biological activity and reinforced antigenicity.

Multiple sugars described as Coupling Sugars (oligosaccharides) with their principal components of maltosyl sucrose and glucosyl sucrose as well as lactosucrose are used in the food industry. They are used as fillers and dispersants, alongside sweeteners such as aspartame, as moderately sweet components in chewing gums for stabilization of trehalose syrups against crystallizing out, or as so-called NDOs (non-digestible oligosaccharides). Also known is improvement and stabilization of the sweetening quality of asparagyl peptides or the sweet-sour relationship in ballast- and sweetener-containing beverages (US 2003/0059511, EP 1 223 175, DE 199 53 727). Further known from U.S. Pat. No. 5,489,577 and EP 0630 651 is the application of oligosaccharides for stabilization of suspensions produced from therapeutic proteins and fat or oil bases. It is stated that, without premixing with the oligosaccharides during blending and kneading with the hydrophobic, semi-solid masses, the proteins would lose their activity. The stabilization potential over storage, in hydrophilic mixtures or in powders, is not mentioned in any way.

A task of the invention was to propose new adjuvants for the production of pharmaceutical preparations. The corresponding preparations were to be distinguished, inter alia, by good long-term stability.

A further task of the present invention was to provide new adjuvants for the production of dried pharmaceutical preparations. The corresponding pulverulent pharmaceutical preparations were to be distinguished by good long-term stability and, if possible, by inhalability.

A further task of the present invention was to provide novel adjuvants for the production of peptide/protein-containing pharmaceutical formulations, particularly those generated by spray drying. The corresponding peptide/protein-containing pharmaceutical preparations were to be distinguished by good long-term stability and, if possible, by inhalability.

A further task of the present invention was to provide novel adjuvants for the formulation of therapeutic antibodies or antibody derivatives, particularly those generated by spray drying. The corresponding antibody-containing pharmaceutical preparations were again to be distinguished by good long-term stability and, if possible, by inhalability.

A further task of the present invention was to provide corresponding pharmaceutical preparations for application in an inhaler, whether in the form of a dry powder, propellant-containing dosage aerosol, or propellant-free inhalation solution.

The tasks underlying the invention are resolved by the following specifications as well as by the objects/processes represented in the patent claims.

INVENTION SUMMARY

The present invention concerns compositions containing one antibody or one antibody derivative and one or more 1,4 O-linked saccharose derivative(s) selected from the combinations: 1,4 O-linked D-Gal-saccharose (lactosucrose), 1,4 O-linked D-Glu-saccharose (glucosyl sucrose), or 1,4 O-linked Glu-Glu-saccharose (maltosyl sucrose). Preferred combinations are those that contain glucosyl and maltosyl sucrose.

The term lactosucrose further means molecules with the following structural formula:

Glucosyl sucrose in the sense of the present invention is further understood to mean molecules with the following structural formula:

The term maltosyl sucrose further means molecules with the following structural formula:

According to a further embodiment form of the invention, the corresponding compositions contain, alongside the antibody or antibody derivative and the 1,4 O-linked saccharose derivative, additionally one or more mono-, di, and/or polysaccharides, whereby the additional application of mono- and/or di-saccharides is preferred. Compositions produced from a combination of glucosyl and maltosyl sucrose in combination with one antibody or one antibody derivative have also proven to accord with the invention, again preferably in combination with mono-, di, and/or polysaccharides.

Compositions particularly according with the invention are thus those with a fraction of (a) 25 to 99.99% (w/w), preferably 80 to 90% (w/w), of at least one 1,4 O-linked saccharose derivative or of a sugar mixture containing at least one 1,4 O-linked saccharose derivative (in relation to the dry weight of the composition) and (b) one antibody or one antibody derivative, preferably at a concentration between 0.01 and 75% (w/w), again in relation to the dry weight of the composition, whereby the sum of the weight percentages of sugar/sugar mixture and antibody or antibody derivative amounts to max 100% (w/w).

The compositions may refer to aqueous compositions, solid or semi-solid compositions. Particularly preferred are solid compositions, preferably pulverulent compositions. It was surprisingly found that corresponding pulverulent antibody-containing compositions i) form an amorphous structure, ii) have a glass transition temperature greater than 40° C., and iii) have a low tendency to recrystallize. This particularly applies to spray-dried powders.

The compositions according to the invention, particularly pulverulent compositions, alongside at least one 1,4 O-linked saccharose derivative or one sugar mixture containing at least one 1,4 O-linked saccharose derivative, may contain further adjuvants, such as e.g. amino acids, peptides, proteins, and other sugars. Particularly advantageous are compositions which, alongside at least one 1,4 O-linked saccharose derivative or one sugar mixture containing at least one 1,4 O-linked saccharose derivative and one antibody or antibody derivative, contain at least one amino acid, one peptide, preferably a di-peptide or tri-peptide, and/or one salt. According to a preferred embodiment form, the present invention preferably concerns pulverulent compositions, such as e.g. spray-dried powders which, in relation to their dry weight, contain (a) between 25 and 90% (w/w) of at least one 1,4 O-linked saccharose derivative or one sugar mixture containing at least one 1,4 O-linked saccharose derivative, (b) between 1 and 39.99% (w/w) of at least one amino acid and/or at least one peptide as a further adjuvant, and (c) at least 0.01% (w/w) of one antibody or antibody derivative. The further adjuvant preferably refers to the amino acid isoleucine or to a peptide, preferably to a di- or tri-peptide, with at least some isoleucine remnant. According to a specific embodiment form, the present invention concerns compositions, such as e.g. spray-dried powders which, in relation to their dry weight, contain (a) around 60 to 80% (w/w) of at least one 1,4 O-linked saccharose derivative or one sugar mixture containing at least one 1,4 O-linked saccharose derivative, (b) around 10 to 19.99% (w/w) of at least one amino acid, preferably isoleucine, and (c) around 0.01 to 30% (w/w) of one antibody or antibody derivative. According to a further alternative embodiment form, the present invention concerns compositions, preferably pulverulent compositions, such as e.g. spray-dried powders, which, in relation to their dry weight, contain (a) around 60 to 80% (w/w) of at least one 1,4 O-linked saccharose derivative or one sugar mixture containing at least one 1,4 O-linked saccharose derivative, (b) around 1 to 19.99% (w/w) of a peptide, preferably an isoleucine-containing peptide, particularly preferably an isoleucine-containing di- or tri-peptide, further preferably tri-isoleucine, and (c) around 0.01 to 39% (w/w) of one antibody or antibody derivative. After being mixed with isoleucine or isoleucine-containing tri-peptides, particularly powders with a corresponding composition show very good fluidity. Corresponding spray-dried powders further have a very high fraction of inhalable particles. Corresponding powders further have very good process and storage stability.

According to a further embodiment form, the present invention concerns corresponding pulverulent compositions, preferably spray-dried powders, which contain a) one or more 1,4 O-linked saccharose derivative(s) in the combinations described above or one sugar mixture containing at least one 1,4 O-linked saccharose derivative and b) at least one antibody or one antibody derivative, whereby the powder has a glass transition temperature greater than 40° C., preferably greater than 45° C., further preferably greater than 50° C., yet further preferably greater than 55° C., and particularly preferably greater than 60° C. The corresponding powders according to the invention normally have a maximum glass transition temperature of around 96 to 110° C. In individual cases, however, the value may be even higher. The fraction of added adjuvant, particularly the fraction of 1,4 O-linked saccharose derivative or the fraction of derivative mixture in the powder, is primarily responsible for the corresponding glass transition temperature.

According to a further embodiment form, the present invention concerns pharmaceutical compositions containing antibodies or antibody derivatives for applications in an inhaler, which contain one of the pulverulent compositions according to the invention described here and consist thereof. Preferred in this context are pharmaceutical compositions which contain the powders according to the invention as propellant-containing dosage aerosols or propellant-free inhalation solutions. The powders according to the invention used for production of the pharmaceutical compositions, preferably powders produced by spray drying, are distinguished according to a further embodiment form by a high fraction of inhalable particles with a median aerodynamic particle diameter (mass median aerodynamic diameter, MMAD) smaller than 10 µm, preferably 0.5-7.5 µm, further preferably 0.5-5.5 µm, particularly preferably 0.5-5.0 µm.

The invention further proposes processes for production of the corresponding compositions according to the invention, preferably pulverulent compositions, such as e.g. production of spray-dried powders, characterized in that an aqueous composition which contains a) one or more 1,4 O-linked saccharose derivative(s) or one sugar mixture containing at least one 1,4 O-linked saccharose derivative and b) at least one antibody or one antibody derivative is produced, and, in the case of a pulverulent composition, the latter is dried under suitable conditions, e.g. sprayed.

DESCRIPTION OF THE FIGURES

All percentage data specified in the descriptions relate to concentrations of solids in solutions (w/w). All legends in the drawings described below relate to the percentage (w/w) composition of powders achieved by spray drying and freeze drying with ensuing pulverization. The legends further specify the total solids concentrations of solutions (total solids=TS) in percent (w/w). In the legend of FIG. 8, Coupling Sugar is abbreviated to CS. In the legends of FIGS. 18, 19, 20, and 21, tri-isoleucine is abbreviated to Ile3. FIGS. 15, 16, 17, 18, 19, 20, and 21 further specify the atomization rate (AAF=atomizing air flow) set during the spray drying process on the Büchi B-290. The figure 40 then corresponds to a real volume flow of ~0.67 m$^3$/h, 50 to a real volume flow of ~1.05 m$^3$/h, and 60 to a real volume flow of ~1.74 m$^3$/h. In all other drawings, the atomization rate of 40 corresponded to a real volume flow of ~0.67 m$^3$/h respectively.

FIG. 1 shows the aggregate content after freeze drying, pulverization, one week's open storage at 75% relative humidity and 40° C. (forced storage stability), and reconstitution. Aqueous solutions with a) 4.5% LS55P fraction and 0.5% IgG fraction, b) 4.5% Coupling Sugar fraction and 0.5% IgG fraction, c) 5.0% IgG fraction, and d) 4.5% mannitol fraction and 0.5% IgG fraction were freeze-dried. Both the LS55P- and Coupling Sugar-containing powders are distinguished by a low aggregate fraction.

FIG. 2 shows the aggregate content after freeze drying, pulverization, equilibration, and four weeks' dry storage at 40° C. (equilibrated storage stability), and reconstitution. Aqueous solutions with a) 4.5% LS55P fraction and 0.5% IgG fraction, b) 4.5% Coupling Sugar fraction and 0.5% IgG fraction, c) 5.0% IgG fraction, and d) 4.5% mannitol fraction and 0.5% IgG fraction were freeze-dried. Both the LS55P- and Coupling Sugar-containing powders are distinguished by a low aggregate fraction.

FIG. 3 shows the aggregate content after freeze drying, pulverization, vacuum drying, four weeks' dry storage at 40° C. (vacuum-dried storage stability), and reconstitution. Aqueous solutions with a) 4.5% LS55P fraction and 0.5% IgG fraction, b) 4.5% Coupling Sugar fraction and 0.5% IgG fraction, c) 5.0% IgG fraction, and d) 4.5% mannitol fraction and 0.5% IgG fraction were freeze-dried. Both the LS55P- and Coupling Sugar-containing powders are distinguished by a low aggregate fraction.

FIG. 4 shows the aggregate content after spray drying, one week's open storage at 75% relative humidity and 40° C. (forced storage stability), and reconstitution. Aqueous solutions with a) 9% LS55P fraction and 1% IgG fraction, b) 9% Coupling Sugar fraction and 1% IgG fraction, c) 9% Coupling Sugar S fraction and 1% IgG fraction, d) 9% trehalose fraction and 1% IgG fraction, and e) 10% IgG fraction were spray-dried. Both the LS55P- as well as the Coupling Sugar- and Coupling Sugar S-containing powders are distinguished by a low aggregate fraction.

FIG. 5 shows the aggregate content after spray drying, one week's open storage at 75% relative humidity and 40° C. (forced storage stability), and reconstitution. Aqueous solutions with a) 8% LS55P fraction, 1% isoleucine fraction, and 1% IgG fraction, b) 8% Coupling Sugar fraction, 1% isoleucine fraction, and 1% IgG fraction, c) 8% Coupling Sugar S fraction, 1% isoleucine fraction, and 1% IgG fraction, d) 8% trehalose fraction, 1% isoleucine fraction, and 1% IgG fraction, and e) 10% IgG fraction were spray-dried. Both the LS55P- as well as the Coupling Sugar- and Coupling Sugar S-containing powders are distinguished by a low aggregate fraction.

FIG. 6 shows the aggregate content after spray drying, one week's open storage at 75% relative humidity and 40° C. (forced storage stability), and reconstitution. Aqueous solutions with a) 3% LS55P fraction, 6% citrulline fraction, and 1% IgG fraction, b) 3% Coupling Sugar fraction, 6% citrulline fraction, and 1% IgG fraction, c) 3% Coupling Sugar S fraction, 16% citrulline fraction, and 1% IgG fraction, d) 3% trehalose fraction, 6% citrulline fraction, and 1% IgG fraction, and e) 10% IgG fraction were spray-dried. Both the LS55P- as well as the Coupling Sugar- and Coupling Sugar S-containing powders are distinguished by a low aggregate fraction.

FIG. 7 shows the aggregate content after spray drying, one week's open storage at 75% relative humidity and 40° C. (forced storage stability), and reconstitution. Aqueous solutions with a) 9.9% LS55P fraction and 0.1% IgG fraction, b) 9% LS55P fraction and 1% IgG fraction, c) 6% LS55P fraction and 4% IgG fraction, d) 4% LS55P fraction and 6% IgG fraction, e) 2.5% LS55P fraction and 7.5% IgG fraction, f) 9% LS55P fraction and 1% IgG fraction, g) 0.5% LS55P fraction and 9.5% IgG fraction, and h) 10% IgG fraction were spray-dried. The LS55P-containing powders are distinguished by a low aggregate fraction.

FIG. 8 shows the aggregate content after spray drying, one week's open storage at 75% relative humidity and 40° C. (forced storage stability), and reconstitution. Aqueous solutions with a) 9.9% Coupling Sugar fraction and 0.1% IgG fraction, b) 9% Coupling Sugar fraction and 1% IgG fraction, c) 6% Coupling Sugar fraction and 4% IgG fraction, d) 4% Coupling Sugar fraction and 6% IgG fraction, e) 2.5% Coupling Sugar fraction and 7.5% IgG fraction, f) 1% Coupling Sugar fraction and 9% IgG fraction, and g) 10% IgG fraction were spray-dried. The LS55P-containing powders are distinguished by a low aggregate fraction.

FIG. 9 shows the aggregate content after spray drying, one week's open storage at 75% relative humidity and 40° C. (forced storage stability), and reconstitution. Aqueous solutions with a) 3.00% LS55P fraction and 0.33% IgG fraction, b) 2.9166% LS55P fraction, 0.0833% tri-isoleucine fraction, and 0.33% IgG fraction, c) 2.833% LS55P fraction, 0.166% tri-isoleucine fraction, and 0.33% IgG fraction, and d) 2.66% LS55P fraction, 0.33% tri-isoleucine fraction, and 0.33% IgG fraction were spray-dried. The LS55P-containing powders are distinguished by a low aggregate fraction. Protein aggregation is further significantly reduced by an increase in the tri-isoleucine fraction from 0% to 10% in relation to the total solids content of the LS55P-containing powders.

FIG. 10 shows the aggregate content after spray drying, one week's open storage at 75% relative humidity and 40° C. (forced storage stability), and reconstitution. Aqueous solutions with a) 3.00% LS90P fraction and 0.33% IgG fraction, b) 2.9166% LS90P fraction, 0.0833% tri-isoleucine fraction, and 0.33% IgG fraction, c) 2.833% LS90P fraction, 0.166% tri-isoleucine fraction, and 0.33% IgG fraction, and d) 2.66% LS90P fraction, 0.33% tri-isoleucine fraction, and 0.33% IgG fraction were spray-dried. The LS90P-containing powders are distinguished by a low aggregate fraction.

FIG. 11 shows the aggregate content after spray drying, one week's open storage at 75% relative humidity and 40° C. (forced storage stability), and reconstitution. Aqueous solutions with a) 2.66% LS90P fraction, 0.33% tri-isoleucine fraction, and 0.33% IgG fraction, b) 2.66% LS55P fraction, 0.33% tri-isoleucine fraction, and 0.33% IgG fraction, c) 2.66% saccharose fraction, 0.33% tri-isoleucine fraction, and 0.33% IgG fraction, d) 2.00% saccharose fraction, 0.66% lactose fraction, 0.33% tri-isoleucine fraction, and 0.33% IgG fraction, e) 2.66% raffinose fraction, 0.33% tri-isoleucine fraction, and 0.33% IgG fraction, f) 2.66% hydroxyethyl starch (HES) fraction, 0.33% tri-isoleucine fraction, and 0.33% IgG fraction, and g) 2.66% trehalose fraction, 0.33% tri-isoleucine fraction, and 0.33% IgG fraction were spray-dried. The LS90P- and LS55P-containing powders are distinguished by a low aggregate fraction, particularly in comparison with raffinose and hydroxyethyl starch (HES) specified as state-of-the-art.

FIG. 12 shows the aggregate content after spray drying, vacuum drying, four weeks' dry storage at 40° C. (vacuum-dried storage stability), and reconstitution. Aqueous solutions with a) 9% Coupling Sugar fraction and 1% IgG fraction, b) 8% Coupling Sugar fraction, 1% (w/w) isoleucine fraction, and 1% IgG fraction, c) 3% Coupling Sugar fraction, 6% citrulline fraction, and 1% IgG fraction, and d) 10% IgG fraction were spray-dried. The Coupling Sugar-containing powders are distinguished by a low aggregate fraction.

FIG. 13 shows the aggregate content after spray drying, vacuum drying, four weeks' dry storage at 40° C. (vacuum-dried storage stability), and reconstitution. Aqueous solutions with a) 9.9% LS55P fraction and 0.1% IgG fraction, b) 9% LS55P fraction and 1% IgG fraction, c) 2.5% LS55P fraction and 7.5% IgG fraction, d) 1% LS55P fraction and 9% IgG fraction, e) 10% IgG fraction, f) 8% LS55P fraction, 1% isoleucine fraction, and 1% IgG fraction, and g) 3% LS55P fraction, 6% citrulline fraction, and 1% IgG fraction were spray-dried. The LS55P-containing powders are distinguished by a low aggregate fraction.

FIGS. 14a+b shows the aggregate content after spray drying, vacuum drying, one or three months' dry storage at 2-8° C., 25° C., and 40° C. (1 or 3 months' stability), and reconstitution. Aqueous solutions with a) 3.00% LS90P fraction and 0.33% IgG fraction, b) 2.66% LS55P fraction, 0.33% isoleucine fraction, and 0.33% IgG fraction, c) 2.66% LS90P fraction, 0.33% isoleucine fraction, and 0.33% IgG fraction, d) 2.66% LS55P fraction, 0.33% tri-isoleucine fraction, and 0.33% IgG fraction, e) 2.66% LS90P fraction, 0.33% tri-isoleucine fraction, and 0.33% IgG fraction, and f) 3.33% IgG fraction were spray-dried. Both the LS90P- and LS55P-containing powders are distinguished by a particularly low aggregate fraction after three months' storage.

FIGS. 15a+b shows the aggregate content after spray drying, vacuum drying, open one or three months' dry storage at 29% relative humidity and 43% relative humidity at 25° C. respectively (open 1 or 3 months' stability), and reconstitution. Aqueous solutions with a) 2.9166% LS90P fraction, 0.0833% tri-isoleucine fraction, and 0.33% IgG fraction at an AAF of 40, b) 2.833% LS90P fraction, 0.166% tri-isoleucine fraction, and 0.33% IgG fraction at an AAF of 40, c) 2.66% LS90P fraction, 0.33% tri-isoleucine fraction, and 0.33% IgG fraction at an AAF of 40, d) 1.60% LS90P fraction, 0.20% tri-isoleucine fraction, and 0.33% IgG fraction at an AAF of 40, e) 2.66% LS90P fraction, 0.33% tri-isoleucine fraction, and 0.33% IgG fraction at an AAF of 50, f) 2.66% LS90P fraction, 0.33% tri-isoleucine fraction, and 0.33% IgG fraction at an AAF of 60, and g) 3.33% IgG fraction at an AAF of 40 were spray-dried. The LS90P-containing powders are distinguished by a particularly low aggregate fraction after three months' storage.

FIG. 16 shows the fine particle fraction (FPF) with a cut-off diameter smaller than 5 µm for various powders. The powders were produced by spray drying of aqueous solutions which have contained LS55P and IgG1 or LS55P, isoleucine and IgG1. The solutions were produced and sprayed as described under EXAMPLES. Isoleucine-containing powder has a FPF of ~35%, whereas isoleucine-free powder only has a FPF of ~16%.

FIG. 17 shows the fine particle fraction (FPF) with a cut-off diameter smaller than 5 µm for various powders. The powders were produced by spray drying of aqueous solutions which have contained LS90P and IgG1 or LS90P, isoleucine and IgG1. The solutions were produced and sprayed as described under EXAMPLES. Isoleucine-containing powder has a FPF of ~28%, whereas isoleucine-free powder only has a FPF of ~23%.

FIG. 18 shows the fine particle fraction (FPF) with a cut-off diameter smaller than 5 µm for various powders. The powders were produced by spray drying of aqueous solutions which have contained LS55P and IgG1 or LS55P, tri-isoleucine and IgG1. The solutions were produced and sprayed as described under EXAMPLES. Tri-isoleucine-containing powders have a FPF of more than 50 or 58%, whereas tri-isoleucine-free powder only has a FPF of ~16%.

FIG. 19 shows the mass median aerodynamic diameter (MMAD) and mass median diameter (MMD) of various powders. The powders were produced by spray drying of aqueous solutions which have contained LS55P and IgG1 or LS55P, tri-isoleucine and IgG1. The solutions were produced and sprayed as described under EXAMPLES. All powders have a MMAD smaller than 5 µm and a MMD smaller than 3.5 µm. The diagram shows the effect of the tri-isoleucine fraction at constant total solids concentrations and spraying parameters on the MMAD and MMD. A 10% tri-isoleucine fraction related to the total solids content of the formulation significantly reduces the MMAD.

FIG. 20 shows the fine particle fraction (FPF) with a cut-off diameter smaller than 5 µm for various powders. The powders were produced by spray drying of aqueous solutions which have contained LS90P and IgG1 or LS90P, tri-isoleucine and IgG1. The solutions were produced and sprayed as described under EXAMPLES. Tri-isoleucine-containing powders have a FPF of ~40% to ~59%, whereas tri-isoleucine-free powder only has a FPF of ~24%.

FIG. 21 shows the mass median diameter (MMD) and mass median aerodynamic diameter (MMAD) of various powders. The powders were produced by spray drying of aqueous solutions which have contained LS90P and IgG1 or LS90P, tri-isoleucine and IgG1. The solutions were produced and sprayed as described under EXAMPLES. All powders have a MMAD smaller than 6.5 µm and a MMD smaller than 5 µm. The diagram shows the effect of the tri-isoleucine fraction at constant total solids concentrations and spraying parameters on the MMAD and MMD. A 10% tri-isoleucine fraction related to the total solids content of the formulation significantly reduces the MMAD. Both a lower solids content (e.g. TS: 2%) and a higher spraying pressure (AAF of 50 or 60), however, significantly reduce the MMD.

FIG. 22 shows the residual monomer content after spray drying, forced storage, and reconstitution. Aqueous solutions with a) 3.33% (w/w) lysozyme fraction, b) 0.33% (w/w) lysozyme fraction and 3.0% (w/w) LS90P fraction, c) 0.33% (w/w) lysozyme fraction, 0.33% (w/w) isoleucine fraction, and 2.66% (w/w) LS90P fraction, and d) 0.33% (w/w) lysozyme fraction, 0.33% (w/w) tri-isoleucine fraction, and 2.66% (w/w) LS90P fraction were sprayed. The LS90P-containing powder is distinguished by a high residual monomer content.

FIG. 23 shows the aggregate content after spray drying, vacuum drying, three months' dry storage at 2-8° C., 25° C., and 40° C. (3 months' stability), and reconstitution. Aqueous solutions with a) 3.33% (w/w) calcitonin fraction, b) 0.166% (w/w) calcitonin fraction and 3.166% (w/w) LS90P fraction, c) 0.166% (w/w) calcitonin fraction, 0.33% (w/w) isoleucine fraction, and 2.833% (w/w) fraction, and d) 0.166% (w/w) calcitonin fraction, 0.33% (w/w) tri-isoleucine fraction, and 2.833% (w/w) fraction were sprayed. The LS90P-containing powder is distinguished by a low aggregate content.

FIG. 24 shows an inhaler for application of dry powder preparations.

DETAILED DESCRIPTION OF THE INVENTION

Definitions

The terms and expressions used within the frame of this invention specification have the meanings defined below. The weight and weight percentage data, unless otherwise indicated, respectively relate to the dry weight of the compositions or to the solids content of the solutions/suspensions. The general embodiment forms "containing" and "contains" are inclusive of the more specific embodiment form "consisting of". "Singular" and "plural" are further used without limitation.

The expression "1,4 O-linked saccharose derivative or a sugar mixture containing at least one 1,4 O-linked saccharose derivative" means i) a 1,4 O-linked saccharose derivative with one of the formulae specified in this patent specification, ii) a mixture thereof, preferably a mixture of maltosyl and glucosyl sucrose, iii) a mixture of at least one 1,4 O-linked saccharose derivative with one of the formulae specified above and further sugars, preferably a mixture of lactosucrose, lactose, and saccharose or of glucosyl and/or maltosyl sucrose, saccharose, fructose, and glucose, iv) a mixture of at least 55% (w/w) lactosucrose, max 25% (w/w) lactose, and max 10% (w/w) saccharose, v) a mixture of at least 88% (w/w) lactosucrose, max 10% (w/w) lactose and saccharose, vi) a mixture of respectively 25% (w/w) glucosyl and/or maltosyl sucrose, between 48 and 56% (w/w) saccharose and not more than 10% (w/w) glucose and fructose, vii) a mixture of respectively 18% (w/w) glucosyl and maltosyl sucrose, between 11 and 15% (w/w) saccharose, and respectively between 5 and 9% (w/w) glucose, viii) a sugar mixture described as Nyuka-Oligo® LS40L (abbreviated to LS40L), Nyuka-Oligo® LS55L (abbreviated to LS55L), Nyuka-Oligo® LS55P (abbreviated to LS55P), Nyuka-Oligo® LS-90P (abbreviated to LS90P), Coupling Sugar®, or Coupling Sugar S® as made by Hayashibara Shoji Inc., Japan.

The expression "composition" means liquid, semi-solid, or solid mixtures of at least two starting substances.

The term "pharmaceutically acceptable adjuvants" relates to adjuvants that can be optionally contained in the formulation within the frame of the invention. The adjuvants may e.g. have pulmonary applications without then having significantly adverse toxicological effects on subjects or subjects' lungs.

The expression "pharmaceutically acceptable salts" covers e.g. the following salts, although not limited thereto: salts of inorganic acids, such as chloride, sulphate, phosphate, diphosphate, bromide, and nitrate salts. Additionally salts of organic acids, such as malate, maleate, fumarate, tartrate, succinate, ethylsuccinate, citrate, acetate, lactate, methanesulphonate, benzoate, ascorbate, para-toluenesulphonate, palmoate, salicylate, and stearate as well as estolate, gluceptate, and lactobionate salts.

The term "pharmaceutically acceptable cations", without being limited thereto, covers e.g. lithium, sodium, potassium, calcium, aluminium, and ammonium (including substituted ammonium).

The expression "amino acid" means compositions containing at least one amino and at least one carboxyl group. Although the amino group is normally located in the α-position to the carboxyl group, any other arrangement in the molecule is conceivable. The amino acid may also contain other functional groups, such as e.g. amino, carboxamide, carboxyl, imidazole, thio, and other groups. Amino acids of natural or synthetic origin with racemic or optical (D or L form) activity, including the different stereoisomeric relationships, are used. For example, the term covers isoleucine as well as D-isoleucine, L-isoleucine, racemic isoleucine, and the different relationships of both enantiomers.

The term "biological macromolecule" means, peptides, proteins, fats, fatty acids, or nucleic acids as well.

The term "peptide" or "polypeptide" means polymers of amino acids consisting of two to one hundred amino acid remnants. The term peptide or polypeptide is used as a pseudonym and covers both homo- and heteropeptides, ie polymers of amino acids consisting of identical or different amino acid remnants. A "di-peptide" is thus composed of two peptidically linked amino acids and a "tri-peptide" of three peptidically linked amino acids. The term "protein" used in this context means polymers of amino acids with more than 100 amino acid remnants.

The term "analogues" means peptides/proteins wherein individual or more amino acids have been substituted, eliminated (e.g. fragments), added (e.g. derivatives with a C or N terminal extension), or otherwise modified from the native (wild type) sequence. Derivatization of native proteins e.g. by sugar, polyethylene glycol, or the like is also possible. Analogues have a bioactivity of at least 10, 20, 30, or 40%, preferably of at least 50, 60, or 70%, and particularly preferably of at least 80, 90, 95, 100% or more than 100% of the bioactivity of the native, non-synthetic protein.

The expression "oligosaccharide" or "polysaccharide" means multiple sugars composed of at least three monomeric sugar molecules.

The expression "pure protein formulation" means a powder consisting of one or more antibodies or antibody derivatives and optionally a suitable buffer (typically 0 to 15% (w/w) in relation to the weight of the dry powder). The powder basically contains no other adjuvants, ie the content of any other adjuvants that may be included is less than 1% (w/w) in relation to the weight of the dry powder.

The term "spray-dried powder formulation" or "dry powder formulation" means powder formulations which normally contain less than around 10% (w/w) residual moisture, preferably less than 7% (w/w) residual moisture, particularly preferably less than 5% (w/w) residual moisture, and yet further preferably less than 3% (w/w) residual moisture. Given constant spray, vacuum, or freeze drying conditions and identical adjuvants, the residual moisture largely depends on the type and fraction of the pharmaceutical active substance in the powder formulation.

The term "amorphous" means that the pulverulent formulations contain less than 10% crystalline fractions, preferably less than 7%, further preferably less than 5%, and particularly preferably less than 4, 3, 2, or 1%.

The term "inhalable" means that the powders are suitable for pulmonary application. Inhalable powders can be dispersed and inhaled with the aid of an inhaler so that the particles can reach the lungs and where necessary unfold systemic action via the alveoli. Inhalable particles e.g. have a particle diameter (mass median diameter, MMD) between 0.4-10 μm, mostly between 0.5-5.0 μm, preferably between 1-3 μm and/or a median aerodynamic particle diameter (mass median aerodynamic diameter, MMAD) between 0.5-10 μm, preferably between 0.5-7.5 μm, further preferably between 0.5-5.5 μm, yet further preferably between 1-5 μm, and particularly preferably between 1-4.5 μm.

Mass median diameter or MMD is a unit characterizing the median particle size distribution, since the powders specified in the invention are generally polydisperse. The results are expressed as the diameter of the total volume distribution at 50% total throughput. The MMD values can be e.g. determined by means of laser diffractometry (cf. the chapter on EXAMPLES, Methods), whereby any other conventional method can also be used (such as e.g. electron microscopy, centrifugal sedimentation).

The term "median aerodynamic particle diameter" (=mass median aerodynamic diameter, MMAD) indicates the aerodynamic particle size at which 50% of powder particles normally have a smaller aerodynamic diameter. The method specified in this patent specification (cf. the chapter on EXAMPLES, Methods) serves as the reference method for MMAD determination in doubtful cases.

The term "fine particle fraction" (FPF) describes the inhalable part of a powder consisting of particles with a particle size of ≦5 μm MMAD. In well dispersible powders, the FPF amounts to more than 20%, preferably more than 30%, particularly preferably more than 40%, yet further preferably more than 50%, and further preferably more than 55%. The term "cut-off diameter" used in this context indicates the particles being considered during FPF determination. An FPF of 30% at a cut-off diameter of 5 μm ($FPF_5$) means that 30% of all particles in the powder have a median aerodynamic particle diameter smaller than 5 μm.

The term "spray solution" means aqueous solutions or suspensions wherein the pharmaceutical active substance is dissolved/suspended together with at least one adjuvant.

The term "time of flight" is the description used in a standard measurement method as described in more detail in the chapter on EXAMPLES. The MMAD and FPF are simultaneously determined during a time of flight measurement (cf. the chapter on EXAMPLES, Methods).

A "surface active" substance is able to reduce the surface tension of the solution wherein it is dissolved. The surface activity is e.g. measured by the tensiometer method proposed by Lecomte du Noüy (Bauer, Frömming, Führer, $6^{th}$ edition).

Compositions According to the Invention

The present invention concerns compositions, preferably pulverulent compositions such as e.g. spray-dried powders, containing a) one antibody or one antibody derivative as pharmaceutical active substance and b) one or more 1,4 O-linked saccharose derivative(s) selected from the combinations: 1,4 O-linked D-Gal-saccharose (lactosucrose), 1,4 O-linked D-Glu-saccharose (glucosyl sucrose), or 1,4 O-linked Glu-Glu-saccharose (maltosyl sucrose).

According to a further embodiment form of the invention, the corresponding compositions contain, alongside the antibody or antibody derivative and the 1,4 O-linked saccharose derivative, additionally one or more mono-, di, and/or polysaccharides, whereby the additional application of mono- and/or di-saccharides is preferred particularly during powder production. The invention also consequently embraces compositions, preferably pulverulent compositions, such as e.g. spray-dried powders with lactosucrose, lactose, and saccharose, whereby the fraction of lactosucrose in relation to the total sugar fraction of the composition amounts to ≧40% (w/w), preferably ≧55% (w/w), and also ≧88% (w/w). According to a preferred embodiment form, the compositions according to the invention, alongside one antibody or antibody derivative as pharmaceutical active substance, contain a sugar mixture specified as Nyuka-Oligo® LS55P (abbreviated to LS55P) of Hayashibara Shoji Inc., Japan which contains at least 55% lactosucrose, max 25% (w/w) lactose, and max 10% (w/w) saccharose. According to a further preferred embodiment form, the compositions according to the invention, alongside the pharmaceutical active substance, contain a sugar mixture specified as Nyuka-Oligo® LS90P (abbreviated to LS90P) of Hayashibara Shoji Inc., Japan which contains at least 88% lactosucrose and max 10% (w/w) lactose and saccharose.

Compositions, preferably pulverulent compositions such as e.g. spray-dried powders consisting of a combination of an antibody and antibody derivative with glucosyl and maltosyl sucrose, have moreover proven to accord with the invention, again preferably in combination with other mono-, di, and/or polysaccharides. The invention also consequently covers corresponding compositions, preferably pulverulent compositions, which, alongside the antibody or antibody derivative, contain a mixture of glucosyl and maltosyl sucrose, saccharose, glucose, and/or fructose, whereby the fraction of glucosyl and maltosyl sucrose in relation to the total sugar fraction of the composition preferably amounts to 25% (w/w) or more.

According to a further preferred embodiment form, the respective fraction of glucosyl and maltosyl sucrose amounts to at least 18% (w/w) of the total sugar fraction of the composition. According to a preferred embodiment form, the compositions according to the invention, preferably the pulverulent compositions, alongside the antibody or antibody derivative as pharmaceutical active substance, contain a sugar mixture described as Coupling Sugar® of Hayashibara Shoji Inc., Japan which respectively contains at least 18% (w/w) glucosyl and maltosyl sucrose, between 11 and 15% (w/w) saccharose, and respectively between 5 and 9% (w/w) glucose and fructose. The present invention further concerns compositions, preferably pulverulent compositions, which, alongside the antibody or antibody derivative as pharmaceutical active substance, contain a sugar mixture described as Coupling Sugar S® of Hayashibara Shoji Inc., Japan which contains at least 25% (w/w) glucosyl and maltosyl sucrose, between 48 and 56% (w/w) saccharose, and not more than 10% (w/w) glucose and fructose.

Compositions, preferably pulverulent compositions such as e.g. spray-dried powders, which have proven to be particularly advantageous are those whose fraction of 1,4 O-linked saccharose derivative or of a sugar mixture containing at least one 1,4 O-linked saccharose derivative in relation to the dry weight of the composition amounts to between 25 and 99.99% (w/w), preferably between 40 and 99% (w/w), further preferably between 60 and 99% (w/w), and yet further preferably between 60 and 90% (w/w), for example 25, 25.1, 25.2, 25.3, . . . 25.7, 25.8, 25.9, etc; 26, 27, 28, 29 30, etc; 31, 32, 33, . . . 38, 39, 40, etc; 41, 42, 43, . . . 48, 49, 50, etc; 51, 52, 53, . . . 58, 59, 60, etc; 61, 62, 63, . . . 68, 69, 70, etc; 71, 72, 73, . . . 78, 79, 80, etc; 81, 82, 83, . . . 88, 89, 90, etc; 91, 92, 93, . . . 98, etc; 99, 99.1, 99.2, 99.3, . . . 99.8, 99.9, etc; 99.91, 99.92, 99.93, . . . 99.98, 99.99% (w/w). In conjunction with application of LS55P or also LS90P, a fraction of 60-90% (w/w) has proven to be particularly advantageous. Where the composition refers to a pulverulent composition, such as e.g. a spray-dried powder, the fraction of 1,4 O-linked saccharose derivative or of sugar mixture containing at least one 1,4 O-linked saccharose derivative should be selected so that the pulverulent composition is at least partially amorphous, preferably completely amorphous. The fraction of 1,4 O-linked saccharose derivative or of sugar mixture containing at least one 1,4 O-linked saccharose derivative may also be reduced below 60% (w/w). Powders are then preferably mixed with other stabilizing adjuvants in suitable quantity. Examples of other stabilizing adjuvants are given elsewhere in this patent specification.

The fraction of antibody or antibody derivative in relation to the dry weight of the composition according to the invention generally amounts to between 0.01 and 75% (w/w), preferably between 0.01 and 50% (w/w), further preferably between 0.33 and 50% (w/w), yet further preferably between 0.33 and 40% (w/w). According to a further preferred embodiment form, the fraction of antibody or antibody derivative in relation to the solids content of the composition according to the invention amounts to between 0.33 and 35% (w/w), preferably between 0.33 and 30% (w/w). For example, the fraction thus amounts to: 0.01, 0.02, 0.03, . . . 0.08, 0.09, etc; 0.1, 0.2, 0.3, . . . 0.8, 0.9, etc; 1, 2, 3, . . . 8, 9, 10, etc; 21, 22, 23, . . . 28, 29, 30, etc; 31, 32, 33, . . . 38, 39, 40, etc; 41, 42, 43, . . . 48, 49, 50, etc; 51, 52, 53, . . . 58, 59, 60, etc; 61, 62, 63, . . . 68, 69, 70, etc; 71, 72, 73, 74, 74.1, 74.2, 74.3, . . . 74.8, 74.9, etc; 74.91, 74.92, 74.93, 74.98, 74.99, 75% (w/w).

Compositions according with the invention are thus compositions, preferably pulverulent compositions such as e.g. spray-dried powders, with a ratio of 1,4 O-linked saccharose derivative or sugar mixture containing at least one 1,4 O-linked saccharose derivative to the pharmaceutical active substance (antibody or antibody derivative) of e.g. 25/75, 26/74, 27/73, 28/72, 29/71, 30/70, 31/69, 32/68, 33/67, 34/66, 35/65, 36/64, 37/63, 38/62, 39/61, 40/60, 41/59, 42/58, 43/57, 44/56, 45/55, 46/54, 47/53, 48/52, 49/51, 50/50, 51/49, 52/48, 53/47, 54/46, 55/45, 56/44, 57/43, 58/42, 59/41, 60/40, 61/39, 62/38, 63/37, 64/36, 65/35, 66/34, 67/33, 68/32, 69/31, 70/30, 71/29, 72/28, 73/27, 74/26, 75/25, 76/24, 77/23, 78/22, 79/21, 80/20, 81/19, 82/18, 83/17, 84/16, 85/15, 86/14, 87/13, 88/12, 89/11, 90/10, 91/9, 92/8, 93/7, 94/6, 95/5, 96/4, 97/3, 98/2, 99/1, 99.1/0.9, 99.2/0.8, 99.3/0.7, 99.4/0.6, 99.5/0.5, 99.6/0.4, 99.66/0.33, 99.7/0.3, 99.8/0.2, 99.9/0.1, 99.99/0.01 (w/w). Where the corresponding composition contains one or more additional adjuvants, either a) the fraction of the 1,4 O-linked saccharose derivative or of the sugar mixture containing at least one 1,4 O-linked saccharose derivative, b) the fraction of antibody or antibody derivative, or c) both fractions are correspondingly reduced, whereby the fraction of the 1,4 O-linked saccharose derivative or of the sugar mixture containing at least one 1,4 O-linked saccharose derivative in relation to the dry weight of the composition according to the invention preferably has one of the values between 60 and 90% (w/w).

Pharmaceutical active substances in the sense of the invention are antibodies or antibody derivatives. Examples thereof, alongside other monoclonal, polyclonal, multispecific, and single-chain antibodies, are fragments thereof, such as e.g. Fab, Fab', F(ab')$_2$, Fc, and Fc' fragments, light (L) and heavy (H) antibody chains and their constant, variable, or hypervariable regions as well as Fd and Fv fragments and fusion proteins containing at least an antibody fraction or at least a fragment of a double- or single-chain antibody (Chamov et al., 1999, Antibody Fusion Proteins, Wiley-Liss Inc.). The antibodies may be of human or non-human origin. The following classes known in humans fall under the latter: IgA, IgD, IgE, IgG, and IgM with their various subclasses, such as e.g. IgA1, IgA2, IgG1, IgG2, IgG3, and IgG4. Humanized and chimeral antibodies also arise in this context. Of special therapeutic importance and thus forming the subject of the present invention are compositions, preferably pulverulent compositions such as e.g. spray-dried powders, which contain antibodies against e.g. various surface antigens, such as CD4, CD20, or CD44, or various cytokinins, such as e.g. IL2, IL4, or IL5. Other examples are antibodies against specific antibody classes (e.g. anti-IgE antibodies) or against viral proteins (e.g. anti-RSV, anti-CMV antibodies, etc).

Fragment antigen-binding or Fab fragments consist of the variable regions of both chains that are held together by the adjacent constant regions. Other antibody fragments are F(ab')$_2$ fragments that can be produced by proteolytic digestion with pepsin. Gene cloning can also be used to produce shortened antibody fragments that only consist of the variable region of the heavy (VH) and light (VL) chain. The latter are described as Fv fragments (fragment variable=fragment of the variable part). Such antibody fragments are also described as single-chain Fv (scFv) fragments. Examples of scFv fragments are known and previously described (see e.g. Huston et al., 1988, Proc. Natl. Acad. Sci. USA, 16, 5879ff).

In previous years, various strategies have been developed to produce multimeric scFv derivatives, such as e.g. dia-, tria- and pentabodies. The expert describes a bivalent homodimeric scFv derivative as a "diabody". Shortening of the peptide linker in the scFv molecule to 5-10 amino acids results in the formation of homodimers through the superposition of VH/VL chains. The diabodies can be additionally stabilized through introduced disulphide bridges. Examples of diabodies have been documented in the literature e.g. by Perisic et al., 1994 (Structure, 2, 1217ff). The expert describes a bivalent homodimeric scFv derivative as a "minibody". It consists of a fusion protein that contains the CH3 region of an antibody, preferably IgG, particularly preferably IgG1, as the dimerizing region. The latter connects the scFv fragments via a hinge region, also of IgG, and a linker region. Both examples of such minibodies have been described by Hu et al., 1996, Cancer Research, 56, 3055ff. The expert describes a trivalent homodimeric scFv derivative as a "triabody" (Kortt et al., 1997, Protein Engineering, 10, 423ff). The direct fusion of VH-VL without application of a linker sequence leads to the formation of trimers.

The fragments described by the expert as mini-antibodies that have a bi-, tri- or tetravalent structure also refer to derivatives of scFv fragments. Multimerizing is then accomplished via di-, tri-, or tetrameric "coiled coil" structures (Pack P. et al., 1993, Biotechnology, 11 1271ff, Lovejoy B. et al., 1993, Science, 259, 1288ff, Pack P. et al., 1995, J. Mol. Biol. 246, 28ff).

An especially preferred embodiment of the invention concerns a protein of the antibody class, more specifically type 1 antibody G. The latter refers to a humanized monoclonal antibody with 95% human and 5% murine antibodies. The antibody has a molecular weight of around 148 kilodaltons (kDa), consisting of two light and two heavy chains and altogether four disulphide bridges.

According to a further embodiment form, the present invention concerns compositions, preferably pulverulent compositions such as e.g. spray-dried powders, characterized in that the dry weight of the corresponding composition contains at least 50% (w/w), preferably between 50 and 99.99% (w/w), particularly preferably between 60 and 90% (w/w) sugar, and up to 40% (w/w) of an antibody or antibody derivative as pharmaceutical active substance, whereby the fraction of lactosucrose, maltosyl sucrose, and/or glucosyl sucrose amounts to at least 20% (w/w) in relation to the dry weight of the composition according to the invention, and the sum of the weight percentages amounts to max 100% (w/w). An expert is able to produce corresponding compositions, preferably pulverulent compositions such as e.g. spray-dried powders as well. An expert thus knows that, in relation to the total solids content of the composition according to the invention, he can mix in max 10% (w/w) of an antibody or antibody derivative, if the fraction of 1,4 O-linked saccharose derivative or a sugar mixture containing at least one 1,4 O-linked saccharose derivative should be 90% (w/w).

The compositions according to the invention, particularly pulverulent compositions such as e.g. spray-dried powders, can moreover contain other adjuvants, such as e.g. amino acids, peptides, non-biological or biological polymers, and/or one or more sugars. Other known state-of-the-art adjuvants are e.g. lipids, fatty acids, fatty acid esters, steroids (e.g. cholesterol), or chelating agents (e.g. EDTA), and diverse cations (see above). Particularly preferred for the production of pulverulent compositions such as e.g. spray-dried powders are adjuvants with a high glass transition temperature, e.g. greater than 40° C., preferably greater than 45° C., further preferably greater than 50° C., or preferably greater than 55° C. A listing of suitable adjuvants is given e.g. in Kippe (eds.) *"Handbook of Pharmaceutical Excipients"* 3$^{rd}$ edition, 2000.

Suitable protein-containing adjuvants are e.g. albumin (of human or recombinant origin), gelatin, casein, hemoglobin, and the like. The sugars preferably refer to a mono-, di-, oligo-, or polysaccharide or to a combination thereof.

Examples of monosaccharides are fructose, maltose, galactose, glucose, D-mannose, sorbose, and the like. Suitable disaccharides in the sense of the invention are e.g. lactose, saccharose, trehalose, cellobiose, and the like. Particularly raffinose, melecitose, dextrin, starch, and the like may be suitably used as multiple sugars, or oligo- and polysaccharides. Among sugar alcohols, mannitol, xylitol, maltitol, galactitol, arabinitol, adonitol, lactitol, sorbitol (glucitol), pyranosylsorbitol, inositol, myoinositol, and the like may be considered as suitable adjuvants. Suitable amino acids e.g. include alanine, glycine, arginine, histidine, glutamate, asparagine, cysteine, lucine, lysine, isoleucine, valine, tryptophan, methionine, phenylalanine, tyrosine, citrulline, L-aspartyl-L-phenylalanine-methyl ester (=aspartame), trimethylammonium acetate (=betaine), and the like. Amino acids that act as a buffer (e.g. glycine or histidine) and/or as a dispersing agent are preferably used. The latter groups particularly include primarily hydrophobic amino acids such as e.g. lucine, valine, isoleucine, tryptophan, alanine, methionine, phenylalanine, tyrosine, histidine, or proline.

Within the frame of the present invention, particularly the application of amino acids, preferably isoleucine or citrulline and particularly preferably isoleucine, has proven advantageous alongside the 1,4 O-linked saccharose derivative or a sugar mixture containing at least one 1,4 O-linked saccharose derivative, preferably at a concentration of 1 to 19.99% (w/w), particularly preferably at a concentration of 5 to 19.99% (w/w), particularly preferably at a concentration of 10 to 19.99% (w/w), and yet further preferably at a concentration of 12 to 19.99% (w/w). The fraction, however, can also be increased to values up to 40% (w/w), provided the fraction of the 1,4 O-linked saccharose derivative or a sugar mixture containing at least one 1,4 O-linked saccharose derivative or the fraction or the antibody or antibody derivative is correspondingly reduced, whereby the solids fraction of the powder cannot exceed 100% (w/w).

It is also particularly advantageous to use as other adjuvants di-, tri-, oligo-, or polypeptides that contain one or more of these primarily hydrophobic amino acid remnants. Particularly preferred are peptides with up to 20 amino acids, further preferred are those with up to 15 amino acids, yet further preferred are those with up to 12 amino acids, yet further preferred are those with up to 11 amino acids, yet further preferred are those with up to 10 amino acids, yet further preferred are those with up to 9 amino acids, yet further preferred are those with up to 8 amino acids, yet further preferred are those with up to 7 amino acids, and yet further preferred are those with up to 7, 6. 5, 4, or 3 amino acids. The peptides used for stabilization then do not simultaneously correspond to the pharmaceutical active substance.

Suitable examples of tri-peptides include e.g. one or more of the following tripeptides: Leu-Leu-Gly, Leu-Leu-Ala, Leu-Leu-Val, Leu-Leu-Leu, Leu-Leu-Met, Leu-Leu-Pro, Leu-Leu-Phe, Leu-Leu-Trp, Leu-Leu-Ser, Leu-Leu-Thr, Leu-Leu-Cys, Leu-Leu-Tyr, Leu-Leu-Asp, Leu-Leu-Glu, Leu-Leu-Lys, Leu-Leu-Arg, Leu-Leu-His, Leu-Gly-Leu, Leu-Ala-Leu, Leu-Val-Leu, Leu-Met-Leu, Leu-Pro-Leu, Leu-Phe-Leu, Leu-Trp-Leu, Leu-Ser-Leu, Leu-Thr-Leu, Leu-Cys-Leu, Leu-Try-Leu, Leu-Asp-Leu, Leu-Glu-Leu, Leu-Lys-Leu, Leu-Arg-Leu, and Leu-His-Leu. Application of tripeptides with the general formulae Ile-X-X; X-Ile-X; X-X-Ile has proven particularly advantageous, where X may be any one of the following amino acids: alanine, glycine, arginine, histidine, glutamic acid, glutamine, asparagine, asparaginic acid, cysteine, lucine, lysine, isoleucine (Ile), valine, tryptophan, methionine, phenylalanine, proline, serine, threonine, tyrosine, L-aspartyl-L-phenylalanine-methyl ester (=aspartame), trimethylammonium acetate. Particularly preferred are corresponding tripeptides with the formula $(Ile)_2$-X, such as e.g. Ile-Ile-X, ILe-X-Ile, or X-Ile-Ile, where X may again be any one of the amino acids specified above. For example, the following peptides are included here: Ile-Ile-Gly, Ile-Ile-Ala, Ile-Ile-Val, Ile-Ile-Ile, Ile-Ile-Met, Ile-Ile-Pro, Ile-Ile-Phe, Ile-Ile-Trp, Ile-Ile-Ser, Ile-Ile-Thr, Ile-Ile-Cys, Ile-Ile-Tyr, Ile-Ile-Asp, Ile-Ile-Glu, Ile-Ile-Lys, Ile-Ile-Arg, Ile-Ile-His, Ile-Gly-Ile, Ile-Ala-Ile, Ile-Val-Ile, Ile-Met-Ile, Ile-Pro-Ile, Ile-Phe-Ile, Ile-Trp-Ile, Ile-Ser-Ile, Ile-Thr-Ile, Ile-Cys-Ile, Ile-Try-Ile, Ile-Asp-Ile, Ile-Glu-Ile, Ile-Lys-Ile, Ile-Arg-Ile, Ile-His-Ile. It is particularly advantageous to use Ile-Ile-Ile.

Suitable polymers e.g. include those specified above as adjuvants, polyvinyl pyrrolidone, derivatized celluloses, such as e.g. hydroxymethyl, hydroxyethyl, or hydroxypropyl ethylcellulose, polymeric sugars, such as e.g. fiscoll, starches, such as e.g. hydroxyethyl or hydroxypropyl starch, dextrins, such as e.g. cyclodextrin (2-hydroxypropyl-β-cyclodextrin, sulphobutylether-β-cyclodextrin), polyethylene glycols, and/or pectins.

The salts e.g. refer to inorganic salts such as chloride, sulphate, phosphate, diphosphate, hydrobromide, and/or nitrate salts. The powders according to the invention may further contain organic salts such as e.g. malate, maleate, fumarate, tartrate, succinate, ethylsuccinate, citrate, acetate, lactate, methanesulphonate, benzoate, ascorbate, para-toluenesulphonate, palmoate, salicylate, stearate, estolate, gluceptate, and lactobionate salts. Corresponding salts may simultaneously contain pharmaceutically acceptable cations such as e.g. sodium, potassium, calcium, aluminium, lithium, or ammonium. Application of corresponding cations during stabilization of antibodies or antibody derivatives has proven particularly suitable.

The present invention thus also concerns compositions, preferably pulverulent compositions such as e.g. spray-dried powders, which, alongside the 1,4 O-linked saccharose derivative or a sugar mixture containing at least one 1,4 O-linked saccharose derivative and one antibody or one antibody derivative as pharmaceutical active substance, contain one or more pharmaceutically compatible adjuvants and/or one or more salts. The adjuvants may e.g. refer to the amino acids, peptides and their salts, sugars, polyols, salts of organic acids, and/or polymers specified above.

According to a further embodiment form, the present invention concerns compositions, preferably pulverulent compositions such as e.g. spray-dried powders, which, alongside the 1,4 O-linked saccharose derivative or a sugar mixture containing at least one 1,4 O-linked saccharose derivative and one antibody or one antibody derivative as pharmaceutical active substance, contain one or more amino acid(s), preferably one amino acid, as a further adjuvant. In this context, the present invention also concerns compositions, preferably pulverulent compositions such as e.g. spray-dried powders, which, in relation to their dry weight, contain a) at least 25% (w/w), preferably between 50 and 90% (w/w), particularly preferably between 60 and 90% (w/w) of one 1,4 O-linked saccharose derivative or one sugar mixture containing at least one 1,4 O-linked saccharose derivative, b) between 1 and 19.99% (w/w) amino acids, and c) between 0.01 and 74% (w/w) antibodies or antibody derivatives as pharmaceutical active substance, whereby the sum of the weight fractions gives 100% (w/w). According to a preferred embodiment form, the fraction of the 1,4 O-linked saccharose derivative or a sugar mixture containing at least one 1,4 O-linked saccharose derivative is at least 60% (w/w), preferably between 70 and 90% (w/w) in relation to the dry weight of the corresponding composition. In a corresponding formulation, the fraction of amino acids preferably amounts to between 1 and 19.99% (w/w) and the fraction of the antibody or antibody derivative to between 0.01 and 39% (w/w).

The present invention according to a further embodiment form also consequently concerns compositions, preferably pulverulent compositions such as e.g. spray-dried powders, which e.g. contain 80% (w/w) of a 1,4 O-linked saccharose derivative or a sugar mixture containing at least one 1,4 O-linked saccharose derivative/19% (w/w) amino acid/1% (w/w) antibody or antibody derivative (80/19/1); or, for example, (80/18/2); (80/17/3); (80/16/4); (80/15/5); (80/14/6); (80/13/7); (80/12/8); (80/11/9); (80/10/10); (70/20/10); (70/19/11); (70/18/12); (70/17/13); (70/16/14); (70/15/15); (70/14/16); (70/13/17); (70/12/18); (70/11/19); (70/10/20); (60/20/20); (60/19/21); (60/18/22); (60/17/23); (60/16/24); (60/15/25); (60/14/26); (60/13/27); (60/12/28); or (60/11/29) or consist thereof. Provided the fraction of antibody or antibody derivative at a constant amino acid fraction is reduced from 20% (w/w) to 0.01% (w/w), e.g. to 9.99, . . . 9.9, 9.8, 9.7, . . . 9.3, 9.2, 9.1, . . . 9, 8, 7, 6, 5, 4, 3, 2, 1, . . . 0.9, 0.8, 0.7, . . . 0.66, . . . 0.6, 0.5, 0.4, 0.3, 0.2, 0.1, 0.09, 0.08, 0.07, 0.06, 0.05, 0.04, 0.03, 0.02, 0.01% (w/w), the fraction of the 1,4 O-linked saccharose derivative or a sugar mixture containing at least one 1,4 O-linked saccharose derivative can be accordingly increased e.g. to 80.01, . . . 80.1, 80.2, 80.3, . . . 80.8, 80.9, . . . 81, 82, 83, 84, 85, 86, 87, 88, 89, . . . 89.1, 89.2, 89.3, . . . 89.33, . . . 89.4, 89.5, 89.6, 89.7, 89.8, 89.9, . . . 89.91, 89.92, 89.93, . . . 89.97, 89.98, 89.99% (w/w), so that the sum of the weight fractions of the individual components of the composition in relation to their dry weight gives 100% (w/w). Through the addition of other adjuvants or salts, the fraction of the 1,4 O-linked saccharose derivative or a sugar mixture containing at least one 1,4 O-linked saccharose derivative amino acids/peptides, and/or antibody or antibody derivative can be correspondingly adjusted/reduced, so that the weight fractions of the individual components in total give 100% (w/w).

Where the added amino acid is isoleucine, then, according to a further embodiment form, compositions, preferably pulverulent compositions such as e.g. spray-dried powders, with a) a fraction of 1,4 O-linked saccharose derivative or a sugar mixture containing at least one 1,4 O-linked saccharose derivative of at least 25% (w/w), preferably from 50 to 90% (w/w), particularly preferably from 60 to 90% (w/w), b) an isoleucine fraction of 1 to 19.99% (w/w), and c) a fraction of at least 0.01% (w/w), preferably 0.01 to max 74% (w/w) of an antibody or antibody derivative as pharmaceutical active substance, preferably a peptide/protein, accord with the invention. The isoleucine fraction preferably amounts to 5 to 19.99% (w/w), further preferably to 10 to 19.99% (w/w), of the total solids fraction of the composition according to the invention. Also valid here is that the sum of the weight percentages of the individual components gives max 100% (w/w). Compositions, preferably pulverulent compositions such as e.g. spray-dried powders, with the following composition also accord with the invention: 80% (w/w) 1,4 O-linked saccharose derivative or a sugar mixture containing at least one 1,4 O-linked saccharose derivative/10% (w/w) amino acid or peptide/10% (w/w) antibody or antibody derivative (80/10/10); (79/11/10); (78/12/10); (77/13/10); (76/14/10); (75/15/10); (74/16/10); (73/17/10); (72/18/10); (71/19/10); (70/20/10), whereby the fraction of antibody or antibody derivative can also be reduced from 10 to 0.01% (w/w), e.g. to 9.99, . . . 9.9, 9.8, 9.7, . . . 9.3, 9.2, 9.1, . . . 9, 8, 7, 6, 5, 4, 3, 2, 1, . . . 0.9, 0.8, 0.7, . . . 0.66, . . . 0.6, 0.5, 0.4, 0.3, 0.2, 0.1, 0.09, 0.08, 0.07, 0.06, 0.05, 0.04, 0.03, 0.02, 0.01% (w/w), and the fraction of the 1,4 O-linked saccharose derivative or a sugar mixture containing at least one 1,4 O-linked saccharose derivative can be accordingly increased e.g. to 80.01, . . . 80.1, 80.2, 80.3, . . . 80.8, 80.9, . . . 81, 82, 83, 84, 85, 86, 87, 88, 89, . . . 89.1, 89.2, 89.3, . . . 89.33, . . . 89.4, 89.5, 89.6, 89.7, 89.8, 89.9, . . . 89.91, 89.92, 89.93, . . . 89.97, 89.98, 89.99% (w/w), so that the sum of the weight fractions of the individual components of the composition in relation to the dry weight of the corresponding composition gives max 100% (w/w). Compositions, preferably pulverulent compositions such as e.g. spray-dried powders, with the following composition thus also accord with the invention: 80% (w/w) 1,4 O-linked saccharose derivative or a sugar mixture containing at least one 1,4 O-linked saccharose derivative/19% (w/w) isoleucine/1% (w/w) antibody or antibody derivative (80/19/1); (80/18/2); (80/17/3); (80/16/4); (80/15/5); (80/14/6); (80/13/7); (80/12/8); (80/11/9); (80/10/10); (70/19/11); (70/18/12); (70/17/13); (70/16/14); (70/15/15); (70/14/16); (70/13/17); (70/12/18); (70/11/19); (70/10/20); (60/19/21); (60/18/22); (60/17/23); (60/16/24); (60/15/25); (60/14/26); (60/13/27); (60/12/28); (60/11/29); (60/10/30). Where other adjuvants or salts are added, the fraction of 1,4 O-linked saccharose derivative or a sugar mixture containing at least one 1,4 O-linked saccharose derivative, isoleucine, and/or antibody or antibody derivative should be correspondingly adjusted, so that the weight fractions of the individual components in total give 100% (w/w).

A further embodiment form of the present invention concerns the application of at least one 1,4 O-linked saccharose derivative or a sugar mixture containing at least one 1,4 O-linked saccharose derivative and a peptide, preferably a di- or tri-peptide, for stabilization of compositions, preferably pulverulent compositions such as e.g. spray-dried powders containing an antibody or antibody derivative as pharmaceutical active substance, preferably in the form of a peptide, protein, or mixture thereof. The present patent specification e.g. specifies a number of tri-peptides which, together with the 1,4 O-linked saccharose derivative or a sugar mixture containing at least one 1,4 O-linked saccharose derivative, can be used for production of the compositions according to the invention, preferably pulverulent compositions such as e.g. spray-dried powders. According to a special embodiment form, the peptides, preferably di- or tri-peptides, refer to those that contain at least one isoleucine remnant, preferably two isoleucine remnants, or, according to a particularly advantageous embodiment form, to tripeptides that consist of three isoluecines.

In this context, compositions, preferably pulverulent compositions such as e.g. spray-dried powders, are deemed to accord with the invention with a) a fraction of at least one 1,4 O-linked saccharose derivative or a sugar mixture containing at least one 1,4 O-linked saccharose derivative of at least 25% (w/w), preferably from 60 to 99% (w/w), particularly preferably from 60 to 90% (w/w), b) a fraction of 1 to 19.99% (w/w) of a peptide, preferably a di- or tri-peptide, particularly preferably an isoleucine-containing peptide, and c) 0.01 to max 74% (w/w) of an antibody or antibody derivative. Also valid here is that the sum of individual solids may not exceed 100% (w/w). Compositions, preferably pulverulent compositions such as e.g. spray-dried powders, with the following composition further accord with the invention: 89% (w/w) of at least one 1,4 O-linked saccharose derivative or a sugar mixture containing at least one 1,4 O-linked saccharose derivative/1% (w/w) peptide, preferably a di- or tri-peptide, particularly preferably an isoleucine-containing tri-peptide, yet further preferably tri-isoleucine/10% (w/w) antibody or antibody derivative (89/1/10); (88/2/10); (87/3/10); (86/4/10); (85/5/10); (84/6/10); (83/7/10); (82/8/10); (81/9/10); (80/10/10); (79/11/10); (78/12/10); (77/13/10); (76/14/10); (75/15/10); (74/16/10); (73/17/10); (72/18/10); or (71/19/10), whereby the fraction of antibody or antibody derivative can also be reduced from 10 to 0.01% (w/w), e.g. to 9.99, . . . 9.9, 9.8, 9.7, . . . 9.3, 9.2, 9.1, . . . 9, 8, 7, 6, 5, 4, 3, 2, 1, . . . 0.9, 0.8, 0.7, . . . 0.66, . . . 0.6, 0.5, 0.4, 0.3, 0.2, 0.1, 0.09, 0.08, 0.07, 0.06, 0.05, 0.04, 0.03, 0.02, 0.01% (w/w), and the fraction of the 1,4 O-linked saccharose derivative or a sugar mixture containing at least one 1,4 O-linked saccharose derivative can be accordingly increased e.g. to 80.01, . . . 80.1, 80.2, 80.3, . . . 80.8, 80.9, . . . 81, 82, 83, 84, 85, 86, 87, 88, 89, . . . 89.1, 89.2, 89.3, . . . 89.33, . . . 89.4, 89.5, 89.6, 89.7, 89.8, 89.9, . . . 89.91, 89.92, 89.93, . . . 89.97, 89.98, 89.99% (w/w), so that the sum of the weight fractions of the individual components of the composition in relation to the dry weight of the composition gives max 100% (w/w). Compositions, preferably pulverulent compositions such as e.g. spray-dried powders, with the following composition further accord with the invention: 80% (w/w) of at least one 1,4 O-linked saccharose derivative or a sugar mixture containing at least one 1,4 O-linked saccharose derivative/19% (w/w) peptide, preferably a di- or tri-peptide, particularly preferably an isoleucine-containing peptide, yet further preferably tri-isoleucine/1% (w/w) antibody or antibody derivative (80/19/1); (80/18/2); (80/17/3); (80/16/4); (80/15/5); (80/14/6); (80/13/7); (80/12/8); (80/11/9); (80/10/10); (70/19/11); (70/18/12); (70/17/13); (70/16/14); (70/15/15); (70/14/16); (70/13/17); (70/12/18); (70/11/19); (70/10/20); (60/19/21); (60/18/22); (60/17/23); (60/16/24); (60/15/25); (60/14/26); (60/13/27); (60/12/28); (60/11/29); (60/10/30), whereby the fraction of antibody or antibody derivative can also be reduced from 10 to 1% (w/w), e.g. to 9.99, . . . 9.9, 9.8, 9.7, . . . 9.3, 9.2, 9.1, . . . 9, 8, 7, 6, 5, 4, 3, 2, 1.9, 1.8, 1.7, . . . 1.66, . . . 1.6, 1.5, 1.4, 1.3, 1.2, 1.1, 1% (w/w), and the fraction of the 1,4 O-linked saccharose derivative or a sugar mixture containing at least one 1,4 O-linked saccharose derivative can be accordingly increased e.g. to 30.1, 30.2, 30.3, . . . 30.8, 30.9, 31, 32, 33, 34, 35, 36, 37, 38, 38.1, 38.2, 38.3, . . . 38.33, . . . 38.4, 38.5, 38.6, 38.7, 38.8, 38.9, . . . 39% (w/w), so that the sum of the weight fractions of the individual components of the composition in relation to the dry weight of the composition gives max 100% (w/w). If the fraction of peptide (di-, tri-, isoleucine-containing peptide, tri- or di-peptide, or tri-isoleucine) is reduced from 10 to 1% (w/w), as represented here, the fraction of the 1,4 O-linked saccharose derivative or a sugar mixture containing at least one 1,4 O-linked saccharose derivative in the powder can also be increased. For example, at a constant active substance fraction of antibody or antibody derivative of 10% (w/w), corresponding compositions with a fraction of 1,4 O-linked saccharose derivative or a sugar mixture containing at least one 1,4 O-linked saccharose derivative of 80.1, 80.2, 80.3, . . . 80.8, 80.9, 81, 82, 83, 84, 85, 86, 87, 88, 88.1, 88.2, 88.3, . . . 88.33, . . . 88.4, 88.5, 88.6, 88.7, 88.8, 88.9, or 89% (w/w) can be produced.

Compositions that have proven to be particularly preferred are compositions, preferably pulverulent compositions such as e.g. spray-dried powders, with a) a fraction of at least one 1,4 O-linked saccharose derivative or a sugar mixture containing at least one 1,4 O-linked saccharose derivative of 60 to 80% (w/w), b) a fraction of 10 to 19.99% (w/w) of a peptide, preferably a di- or tri-peptide, particularly preferably an isoleucine-containing peptide, further preferably a tri-peptide, preferably of tri-isoleucine, and c) 0.01 to max 30% (w/w) of an antibody or antibody derivative. Also valid here is that the sum of individual solids may not exceed 100% (w/w).

According to a further embodiment form that accords with the invention, the compositions, preferably pulverulent compositions such as e.g. spray-dried powders, may additionally contain surface-active substances, such a Tween 20, 40, 60, 80, Brij 35, Pluronic F 88, and Pluronic F 127. The latter substances are preferably used at a concentration of 0.01-0.1% (w/w). Particularly preferred are compositions, preferably pulverulent compositions such as e.g. spray-dried powders, which contain, as adjuvant, at least one 1,4 O-linked saccharose derivative or a sugar mixture containing at least one 1,4 O-linked saccharose derivative and additionally Tween 20, preferably at a concentration of 0.01-0.1% (w/w) as surface-active substances.

According to a further embodiment form, the particles in the pulverulent compositions according to the invention have a MMD between 1 and 10 μm, preferably between 1 and 5 μm.

According to a further embodiment form, the present invention concerns compositions, preferably pulverulent compositions such as e.g. spray-dried powders, that contain a) at least one 1,4 O-linked saccharose derivative or a sugar mixture containing at least one 1,4 O-linked saccharose derivative and b) one antibody or one antibody derivative, whereby the pulverulent composition is characterized by a glass transition temperature greater than 40° C. The corresponding powders according to the invention normally have a maximum glass transition temperature of around 96 to 110° C. In individual cases, however, the value may be even higher.

The present invention further concerns pharmaceutical compositions that contain at least one of the compositions described here.

Production of the Compositions According to the Invention

The compositions according to the invention refer to liquid, semi-solid, or solid compositions that contain a) at least one 1,4 O-linked saccharose derivative or a sugar mixture containing at least one 1,4 O-linked saccharose derivative and b) one antibody or one antibody derivative. Particularly preferred are solid pulverulent compositions, such as e.g. those generated by freeze drying or spray drying of an aqueous solution or suspension. Aqueous solutions or suspensions can be obtained through mixing or suspension of corresponding components (such as e.g. a 1,4 O-linked saccharose derivative and an antibody) in a suitable solvent. The respective substances can also be added as dry substances to a solvent and dissolved or suspended therein. Semi-solid preparations are also suitable. Semi-solid preparations consist of a simple or composition base wherein, according to the invention, a) a 1,4 O-linked saccharose derivative or a sugar mixture containing at least one 1,4 O-linked saccharose derivative and b) antibodies or antibody derivatives are dissolved or dispersed. The 1,4 O-linked saccharose derivative or a sugar mixture containing at least one 1,4 O-linked saccharose derivative and antibodies or antibody derivatives can be added to the base individually or, as described above, within a powder produced by a suitable process described above. The preparations may further contain suitable adjuvants such as preservatives, antioxidants, stabilizers, emulsifiers, thickeners, and penetration accelerators, or other suitable adjuvants. Suitable semi-solid bases are, without being limited thereto, hydrophobic ointments, water-absorbing ointments, hydrophilic ointments, lipophilic creams, hydrophilic creams, lipophilic gels, hydrophilic gels, pastes, and enrobing pastes.

Particularly preferred are solid pulverulent compositions generated e.g. through drying of previously aqueous solutions or suspensions. Known drying processes include, inter alia, freeze drying, spray drying, vacuum drying, infrared drying, or microwave drying. A general description of appropriate processes is given e.g. in the publication by Willmann (Dissertation, 2000, Dr. Hut Verlag, Munich, Germany—ISBN 3-89963-027-0), to whose contents reference is made. Pulverulent compositions consisting of a) at least one 1,4 O-linked saccharose derivative or a sugar mixture containing at least one 1,4 O-linked saccharose derivative and b) one antibody or antibody derivative which have been produced by spray drying or freeze drying have proven to be particularly stable.

Production of Dried Powders According to the Invention

The present invention also provides processes for the production of a dried powder described in more detail above, preferably a spray-dried powder. The spray drying process is e.g. characterized in that a solution/suspension to be sprayed that contains a) an antibody or antibody derivative as pharmaceutical active substance and b) at least one 1,4 O-linked saccharose derivative or a sugar mixture containing at least one 1,4 O-linked saccharose derivative is sprayed below a temperature of 200/120° C. (inlet/outlet temperature), preferably at a temperature below 186/96° C., preferably between 186/96° C. and 60/40° C., e.g. at 180-150/95-80° C. The process according to the invention is described in more detail on the basis of a number of examples in the section on EXAMPLES.

The powders according to the invention can be basically produced through the antibody or antibody derivative being dissolved in an aqueous solution depending on the solubility conditions of the antibody or antibody derivative. Buffered solutions with a pH of 3-11, preferably 3.5-9, are mostly used. During the production of inhalable powders, an aqueous solution with a pH of 4-7.8 is particularly advantageous. To guarantee adequate solubility, the pH value of the solution should be below the pH value of the antibody/antibody derivative. The aqueous solution may optionally contain additional water-soluble organic solvents, such as e.g. acetone, alcohols, or the like. Particularly suitable are lower alcohols, such as e.g. methanol, ethanol, or propanol (n- or iso-propanol). Such mixed solvent systems normally contain between 10-20% (v/v) of a water-soluble organic solvent. The solids fraction in the solution to be dried generally amounts to between 0.01-20% (w/w), preferably between 0.05-10% (w/w), particularly preferably between 0.1-5% (w/w). Within the frame of the present invention, spray-dried powders were produced on the basis of an aqueous solution with a solids fraction of 10% (w/w), 3.33% (w/w), or 2.00% (w/w) as well as freeze-dried powders on the basis of an aqueous solution with a solids fraction of 10% (w/w).

The adjuvant or a mixture of suitable adjuvants, as e.g. specified above, is normally dissolved in a second container in purest water or a suitable buffer solution with a pH value of 3 to 11, preferably 3.5 to 9, and particularly preferably 4.0 to 7.8, and mixed in a second step with the active substance solution that contains the antibody or antibody derivative. The solution/suspension is then adjusted to the required solids content with purest water or a suitable buffer solution with a pH value of 3 to 11, preferably 3.5 to 9, and particularly preferably 4.0 to 7.8.

The present invention consequently concerns a process for the production of a powder, characterized in that
  a) an antibody or antibody derivative is dissolved in an aqueous solution/suspension;
  b) one or more 1,4 O-linked saccharose derivatives selected from the combinations lactosucrose, glucosyl sucrose, or maltosyl sucrose or a sugar mixture containing at least one of these 1,4 O-linked saccharose derivatives is/are dissolved/suspended in an aqueous solution/suspension;
  c) where an antibody or antibody derivative and 1,4 O-linked saccharose derivatives or the sugar mixture containing at least one 1,4 O-linked saccharose derivative are dissolved/suspended in different solutions/suspensions, these are mixed;
  d) The solution/suspension containing one or more 1,4 O-linked saccharose derivative(s) and the antibody or antibody derivative is dried.

Where the drying process refer to spray drying, drying proceeds under point d) through spraying of the corresponding solution/suspension below a temperature of 200/120° C. (inlet/outlet temperature), preferably between 60/40° C. and 186/96° C.

The 1,4 O-linked saccharose derivative may also form part of a sugar mixture containing at least one 1,4 O-linked saccharose derivative. Examples of correspondingly suitable sugar mixtures are e.g. described in more detail in "Definitions". The sugar mixtures, alongside the 1,4 O-linked saccharose derivative, may then additionally contain one or more mono-, di, and/or polysaccharides, whereby the additional application of mono- and/or di-saccharides is preferred, particularly during powder production. Within the frame of the invention, sugar mixtures may thus e.g. be used with lactosucrose, lactose, and saccharose, whereby the fraction of lactosucrose in relation to the total sugar fraction of the composition amounts to $\geq 40\%$ (w/w), preferably $\geq 55\%$ (w/w), and also $\geq 88\%$ (w/w). The sugar mixture preferably refers to a sugar mixture specified as Nyuka-Oligo® LS55P (abbreviated to LS55P) of Hayashibara Shoji Inc, Japan which contains at least 55% lactosucrose, max 25% (w/w) lactose, and max 10% (w/w) saccharose. According to a further preferred embodiment form, the sugar mixture preferably refers to a sugar mixture specified as Nyuka-Oligo® LS90P (abbreviated to LS90P) of Hayashibara Shoji Inc, Japan which contains at least 88% lactosucrose and max 10% (w/w) lactose and saccharose. Sugar mixtures consisting of a combination of glucosyl and maltosyl sucrose, again preferably in combination with other mono-, di, and/or polysaccharides, may further be used. Sugar molecules that are suitable in the sense of the present invention are consequently those that consist of glucosyl and maltosyl sucrose, saccharose, glucose, and/or fructose, whereby the fraction of glucosyl and maltosyl sucrose in relation to the total sugar fraction of the composition preferably amounts to 25% (w/w) or more. According to a further preferred embodiment form, the respective fraction of glucosyl and maltosyl sucrose amounts to at least 18% (w/w) of the total sugar fraction. According to another preferred embodiment form, the used sugar mixture refers to a Coupling Sugar® of Hayashibara Shoji Inc, Japan which respectively contains at least 18% (w/w) glucosyl and maltosyl sucrose, between 11 and 15% (w/w) saccharose, and respectively between 5 and 9% (w/w) glucose and fructose. Also suitable in the sense of the present invention is a sugar mixture described as Coupling Sugar S® of Hayashibara Shoji Inc, Japan which contains at least 25% (w/w) glucosyl and/or maltosyl sucrose, between 48 and 56% (w/w) saccharose, and not more than 10% (w/w) glucose and fructose.

The adjuvant content of the 1,4 O-linked saccharose derivative or a sugar mixture containing at least one 1,4 O-linked saccharose derivative in the solution/suspension to be dried amounts to between 25% and 99.99% (w/w), preferably between 60% and 99% (w/w), and particularly preferably between 60% and 90% (w/w), in relation to the solids content of the solution or suspension to be dried. The active substance concentration of antibody or antibody derivative normally amounts to between 0.01 and 75% (w/w), preferably between 0.01 and 40% (w/w), particularly preferably between 0.01 and 30% (w/w), in relation to the solids content of the solution or suspension to be dried. On the basis of the powder compositions according to the invention described above, the expert is able to produce solutions/suspensions to be dried which, after drying, particularly after spraying, lead to the corresponding powder compositions.

The present invention also consequently concerns processes for the production of a dried powder, as described above, characterized in that the solids content of the solution/suspension to be dried contains between 25 and 99.99% (w/w), preferably between 60 and 99% (w/w), of at least one 1,4 O-linked saccharose derivative or a sugar mixture containing at least one 1,4 O-linked saccharose derivative. According to a further preferred embodiment form, the present invention concerns a corresponding process, characterized in that the solids fraction of the solution/suspension to be dried contains between 0.01 and 75% (w/w), preferably between 0.01 and 30% (w/w), particularly preferably between 0.33 and 30% (w/w), of antibodies or antibody derivatives as pharmaceutical active substance.

According to a further embodiment form, a solution/suspension to be dried with a solids content of a) at least 25% (w/w), e.g. between 25 and 99.99% (w/w), of at least one 1,4 O-linked saccharose derivative or a sugar mixture containing at least one 1,4 O-linked saccharose derivative and b) at least 0.01% (w/w), preferably 0.01 to 75% (w/w), of an antibody or antibody derivative as pharmaceutical active substance is produced and dried, preferably sprayed, whereby the sum of the weight percentages amounts to max 100% (w/w). According to a preferred embodiment form, a solution/suspension to be dried with a solids content a) of at least one 1,4 O-linked saccharose derivative or a sugar mixture containing at least one 1,4 O-linked saccharose derivative of at least 60% (w/w), preferably between 60 and 90% (w/w), and b) 0.01 and 40% (w/w) of an antibody or antibody derivative is produced and dried, preferably sprayed, whereby the sum of the weight percentages of the solution or suspension amounts to max 100% (w/w) in relation to the solids content of the spray solution/spray suspension.

Depending on the powders according to the invention as described above, the solution/suspension to be dried according to a further embodiment form additionally contains one or more pharmaceutically compatible adjuvants and/or one or more salts. The adjuvants chiefly refer to amino acids, peptides or their salts, sugars, polyols, salts of organic acids, and/or polymers.

The solution/suspension to be dried, alongside a) one antibody or antibody derivative as pharmaceutical active substance and b) at least one 1,4 O-linked saccharose derivative or a sugar mixture containing at least one 1,4 O-linked saccharose derivative, preferably contains c) one or more amino acids and/or peptides or proteins as other adjuvants. The present invention also consequently concerns a process for the production of dried, preferably spray-dried, powders, characterized in that the solution/suspension to be dried, in relation to its solids content, a) at least 25% (w/w), preferably at least 60 to 90% (w/w), of at least one 1,4 O-linked saccharose derivative or a sugar mixture containing at least one 1,4 O-linked saccharose derivative, b) between 1 and 19.99% (w/w) of at least one amino acid and/or at least one peptide, and c) between 0.01 and 74% (w/w) of antibodies or antibody derivatives. Examples of suitable adjuvants, including pharmaceutically compatible salts, peptides, and amino acids, are given under "Powders according to the invention" in this patent specification. An expert is then able to produce corresponding powders and to adjust the weight fractions in such a way that the sum of the solid fractions amounts to max 100% (w/w). Where the fraction (in relation to the total solids content) of antibody or antibody derivative amounts e.g. to 10% (w/w) and the fraction of at least one 1,4 O-linked saccharose derivative or a sugar mixture containing at least one 1,4 O-linked saccharose derivative amounts to 80% (w/w), the expert knows that he can add max 10% (w/w) of amino acids to the solution/suspension to be dried.

According to a further preferred embodiment form, the solution/suspension to be dried, alongside at least one 1,4 O-linked saccharose derivative or a sugar mixture containing at least one 1,4 O-linked saccharose derivative, additionally contains isoleucine as a further adjuvant. Solutions/suspensions deemed advantageous are those whose solids fraction contains a) at least 25% (w/w), preferably at least 60 to 90% (w/w), of at least one 1,4 O-linked saccharose derivative or a sugar mixture containing at least one 1,4 O-linked saccharose derivative, b) between 1 and 19.99% (w/w) of isoleucine, and c) at least 0.01% (w/w) of an antibody or antibody derivative as pharmaceutical active substance. The fraction of antibody or antibody derivative is then preferably 0.01 to max 74% (w/w), whereby the sum of the solid fractions amounts to max 100% (w/w). An expert is then able to produce corresponding powders, preferably by spray drying, and to adjust the weight fractions in such a way that the sum of the solid fractions amounts to max 100% (w/w). Where the fraction (in relation to the total solids content) of antibody or antibody derivative amounts e.g. to 10% (w/w) and the fraction of at least one 1,4 O-linked saccharose derivative or a sugar mixture containing at least one 1,4 O-linked saccharose derivative amounts to 80% (w/w), the expert knows that he can add max 10% (w/w) of isoleucine to the solution/suspension to be dried.

According to a further embodiment form, the solution/suspension to be dried, alongside at least one 1,4 O-linked saccharose derivative or a sugar mixture containing at least one 1,4 O-linked saccharose derivative, contains one or more tri-peptides, particularly preferably tri-isoleucine. Solutions/suspensions deemed advantageous are those whose solids fraction contains a) at least 25% (w/w), preferably 60 to 99.99% (w/w), particularly preferably 60 to 90% (w/w), of at least one 1,4 O-linked saccharose derivative or a sugar mixture containing at least one 1,4 O-linked saccharose derivative, b) between 1 and 19.99% (w/w) of a peptide, preferably a di- or tri-peptide, particularly preferably an isoleucine-containing peptide, further preferably tri-isoleucine, and c) at least 0.01% (w/w) of an antibody or antibody derivative as pharmaceutical active substance, whereby the sum of the solid fractions amounts to max 100% (w/w). The fraction of the antibody or antibody derivative then preferably amounts to 0.01 to max 74% (w/w). An expert is then able to produce corresponding powders and to adjust the weight fractions in such a way that the sum of the solid fractions amounts to max 100% (w/w). Where the fraction (in relation to the total solids content) of antibody or antibody derivative amounts e.g. to 10% (w/w) and the fraction of at least one 1,4 O-linked saccharose derivative or a sugar mixture containing at least one 1,4 O-linked saccharose derivative amounts to 80% (w/w), the expert knows that he can add max 10% (w/w) of a peptide, preferably a di- or tri-peptide, particularly preferably an isoleucine-containing peptide, further preferably tri-isoleucine, to the solution or suspension to be dried, preferably sprayed.

As already noted, it is advantageous to produce and spray solutions to be dried, preferably sprayed, with a pH value of 3 to 11, preferably 3.5 to 9, and particularly preferably 4.0 to 7.8. Suitable buffer systems are known to the expert. The application of inorganic or organic salts as buffer system normally proves to be particularly advantageous.

The optimum adjuvant and protein content for each antibody or antibody derivative is typically determined experimentally. Preferred formulations of the invention may also contain a further adjuvant in order to improve powder properties such as dispersibility and fluidity with retention of superior aggregate suppression.

Spray Drying

Spray drying proceeds in conventional spray dryers, such as e.g. in facilities manufactured by Niro A/S (Soeborg, DK), Büchi Labortechnik GmbH (Flawil, CH), or the like. The optimum conditions for spray drying respectively depend on the corresponding formulation and should be experimentally determined. Air is typically used as gas. However, other inert gases, such as nitrogen or argon, are suitable. The spray drying temperature, which means the inlet and outlet temperature, is further determined depending on the temperature sensitivity of the active substance used and in each case depending on the stabilizers used. It is usual to have an inlet temperature of 50-200° C., whereas the outlet temperature is mostly 30-150° C. Operations within the frame of the present invention were performed at an inlet temperature of around 170-185° C. and an outlet temperature of 80-100° C. However, it is also possible to have an inlet temperature of up to 200° C., preferably 60-185° C., and an outlet temperature of up to 120° C., preferably 40-105° C., depending on the stabilizer fraction. Spraying generally proceeds at a pressure of around 29-150 psi, preferably around 30- or 40-100 psi, e.g. at around 30, 40, 50, 60, 70, 80, 90, or 100 psi.

In respect of the Büchi type B-290 Spray Dryer, the liquid feed rate is normally between 0.1 and 100 ml/min, preferably between 0.1 and 30 ml/min, such as e.g. around 3 ml/min. In this context, an aspirator flow rate of 20-40 $m^3/h$, preferably 30-40 $m^3/h$, such as e.g. 38.3 $m^3/h$, and atomizing flow rates of 0.3-2.5 $m^3/h$, preferably of around 0.67 $m^3/h$, 1.05 $m^3/h$, and 1.74 $m^3/h$, have proven to be particularly suitable.

The spray-dried antibody or antibody derivative formulations may be optionally subjected to a second gentle drying (after-drying). The purpose is to obtain a standard residual water content in formulations, preferably less than 2% (w/w), and thereby to improve both the active substance stability and powder properties, such as glass transition temperature, fluidity, and dispersibility. The conditions of the after-drying process must be selected in such a way that aggregation of the antibody or antibody derivative does not significantly increase. The spray-dried active substance formulations are preferably produced, further processed, and stored under dry conditions (at low relative air humidity). The after-drying process enables the powder, despite relatively high initial residual water contents after spray drying, to be reduced further in terms of moisture content. Surprisingly, adjuvants as objects of the invention are stabilized in the preferred formulations, which are superior to proteins even under non-optimum process and storage conditions.

Freeze Drying

Freeze drying of aqueous solutions can be performed according to the description given in "Lyophilisation" by Essig and Oschmann (Wissenschaftliche Verlagsgesellschaft, Stuttgart, 1993). The therapeutic active substance and an antibody or antibody derivative are normally freeze-dried as an aqueous solution or suspension. Consideration should be given to suitable concentrations and pH values. In a preferred formulation, the antibody or antibody derivative is initially dissolved in an aqueous solution with a suitable buffer system. The pH value of protein-containing solutions is generally from 3 to 11, preferably 3.5 to 9, and particularly preferably between 4.0 and 8. The pH value of the solution must be set below or above the isoelectric point of the antibody/antibody derivative. In a second container, the adjuvant or a mixture of suitable adjuvants is dissolved in purest water or a suitable buffer solution with a pH value of 3 to 11, preferably 3.5 to 9, and particularly preferably 4.0 to 8.5, and in a second step mixed with the protein solution. Finally, the solution with purest water or a suitable buffer solution with a pH value of 3 to 11, preferably 3.5 to 9, and particularly preferably 4.0 to 8.5. is set to the required solids content. Suitable total solids contents are between 0.1 and 30% (w/w), preferably between 0.5 and 20% (w/w), and particularly preferably between 0.75 and 15.0% (w/w).

The solutions are then freeze-dried in a conventional commercial freeze dryer, such as type Christ LPC-16/NT Epsilon 2-12 D manufactured by Martin Christ Gefriertrocknungsanlagen GmbH, or the like. The product is a protein-containing powder or cake, which, before of any further processing, is then is reduced in size in a suitable process in order to obtain a polydisperse powder.

The temperatures in the freeze dryer are experimentally optimized and generally range between −70° C. and +100° C., preferably between −50° C. and +40° C. Preferred pressure parameters in the freeze dryer are a pressure of $10*e\text{-}5$ to 1013 mbar. After their size reduction, the freeze-dried protein formulations may be preferably subjected to a second gentle drying (after-drying). The purpose is to retain a standard residual water content in formulations of less than 2% (w/w) and thereby to improve both the antibody stability and powder properties, such as glass transition temperature, fluidity, and dispersibility. The conditions of the after-drying process must be selected in such a way that aggregation of the protein does not significantly increase.

Properties of the Spray-Dried Dry Powder Formulations

The dry protein-powder formulations produced within the frame of this invention have a residual water content of less than 15% (w/w), usually less than 10% (w/w), and preferably less than 6% (w/w). The spray-dried protein-powder formulations also preferably have a residual water content of less than 5% (w/w), particularly preferably less than 3% (w/w), and most preferably between 0.2 and 2.0% (w/w). Formulations with a low residual moisture content generally exhibit improved stability during packing and storage. The dry protein-powder formulations according to the invention are moreover especially hygroscopic, ie they tend to absorb moisture from their environment. To avoid this, such powders are usually stored in containers such as blister packs ensuring exclusion of airborne moisture. Surprisingly, it was found for selected formulations of powders according to the invention that the powders, even after one month's open storage at 43% relative air humidity, remain stable in terms of both protein stability and inhalability.

The stabilizing effects of the adjuvants described here are able to protect the protein from extreme loadings during spray drying and storage. Pure protein formulations spray-dried in the absence of adjuvants form aggregates to a large extent. Process-dependent factors such as heat, shear stress, and denaturation at the air-water interfaces give rise to aggregation (up to around 6.6% aggregates) during spray drying and ensuing after-drying (up to around 5.8% aggregates). In the course of storage, the absence of the stabilizing hydrate shell of proteins gives rise to massive aggregation (of around 11.8 to around 18.9% aggregates).

The preferred spray-dried formulations of the invention, in contrast to the pure protein formulations, are able both to reduce the formation of aggregates after spray drying and to keep this to a very low level even under a variety of storage conditions. Through spray drying and ensuing vacuum drying, only around 0.5 to around 1.8% aggregates form in the preferred formulations in contrast to around 4.0% aggregates in pure protein formulations. Under particularly challenging storage conditions (40° C., 75% relative humidity) of forced storage stability, the preferred formulations show clear superiority (aggregates of around 1.0 to around 13.1%) over the pure protein formulations (around 18.2 to 18.9% aggregates) as well as over an analogous reference formulation with trehalose as adjuvant. This advantage becomes particularly evident in the comparison made with the formulation given in example 4. The addition of tri-isoleucine in the spray solution leads to significant improvement of the aerodynamic properties of powders. Surprisingly, only the combinations that contain at least one 1,4 O-linked saccharose derivative, preferably lactosucrose and tri-isoleucine, particularly LS55P and tri-isoleucine as well as LS90P and tri-isoleucine, are able to safeguard the protein from aggregation (only 0.7 to 4.4% aggregates). Neither the raffinose (12.6% aggregates) and hydroxyethyl starch (around 18.6% aggregates) used in combination with tri-isoleucine described in WO 01/32144 nor the state-of-the-art trehalose described as a superior stabilizer are able to protect the protein from aggregation under particularly challenging conditions in combination with tri-isoleucine. Both the LS55P-tri-isoleucine formulations and the LS90P-tri-isoleucine formulations also appear clearly advantageous over a saccharose-tri-isoleucine formulation (5.6% aggregates) and a saccharose-lactose-tri-isoleucine formulation (8.8% aggregates). This is even more surprising in that LS55P, alongside saccharose, also contains up to 25% lactose. It is clearly the case that the negative effect exerted by the reducing sugar lactose on protein stability is overcompensated in LS55P by the 1,4 O-linked saccharose derivative lactosucrose. A high fraction of lactosucrose in the sugar fraction of the formulation is even more advantageous for protein stability (see LS90P formulations).

Formulations which, during relatively short-term storage under particularly destabilizing conditions (one week at 40° C., 75% relative humidity), already have a significant stabilizing effect on the incorporated proteins and stabilize the proteins in the long term under much milder standard storage conditions (e.g. one year dry at around 25° C.).

After equilibration with ensuing four weeks' storage under dry conditions at 40° C. (equilibrated storage stability), the LS55P and Coupling Sugar containing powder formulations are distinguished by low aggregate contents (around 1.4 to 3.2% aggregates), particularly in comparison with pure protein powders (around 11.8% aggregates).

After vacuum drying with ensuing four weeks' storage under dry conditions at 40° C. (vacuum-dried storage stability), the LS55P and Coupling Sugar containing powder formulations are distinguished by low aggregate contents (around 1.1 to 2.1% aggregates), particularly in comparison with pure protein powders (around 13.2% aggregates).

LS55P (80%), isoleucine (10%), and IgG1 (10%) formulations with a fine particle fraction of around 35% show aggregate contents below 1.9% after vacuum drying with ensuing filling in nitrogen after three months' storage under dry conditions at 2 to 8° C., 25° C., and 40° C.

LS55P (80%), tri-isoleucine (10%), and IgG1 (10%) formulations with a MMAD of around 3.9 µm and a fine particle fraction of 58.3% after spray drying show aggregate contents below 1.9% after vacuum drying with ensuing filling in nitrogen after three months' storage under dry conditions at 2 to 8° C., and 25° C. and ag contents below 2.6% under dry storage conditions at 40° C. (3 months' stability).

After one month's open storage at around 43% relative air humidity and 25° C. (open 1 month's stability), the specified LS55P (80%), tri-isoleucine (10%), and IgG1 (10%) formulations further show a low aggregate content (around 1.3%) at approximately the same low MMAD (around 3.8 µm) and the same high fine particle fraction (around 59.6%).

LS90P (90%) and IgG1 (10%) formulations with a MMAD of around 3.8 µm, a MMD of around 2.8 µm, and a fine particle fraction of around 24% after spray drying show aggregate contents below 1.2 and 2.2% respectively after vacuum drying with ensuing filling in nitrogen after one and three months' storage under dry conditions at 2 to 8° C., 25° C., and 40° C. (1 and 3 months' stability).

LS90P (80%), isoleucine (10%), and IgG1 (10%) formulations with a fine particle fraction of around 28% spray drying show aggregate contents below 0.9 and 1.1% respectively after vacuum drying with ensuing filling in nitrogen after one and three months' storage under dry conditions at 2 to 8° C., 25° C., and 40° C. (1 and 3 months' stability).

LS90P (80%), tri-isoleucine (10%), and IgG1 (10%) formulations with a MMAD of around 4.8 µm and a fine particle fraction of around 53.2% after spray drying show aggregate contents below 1.0 and 2.3% respectively after vacuum drying with ensuing filling in nitrogen after one and three months' storage under dry conditions at 2 to 8° C., 25° C., and 40° C. (1 and 3 months' stability).

After one and three months' open storage at around 43% relative air humidity and 25° C. (open 1 and 3 months' stability), variations in the LS90P (80%), tri-isoleucine (10%), and IgG1 (10%) formulations specified above further show low aggregate contents below around 0.5% and 0.8%. After spray drying, the MMAD values range between 3.9 and 3.3 µm and the FPF values between around 55.6 and 58.9%. After one month's open storage at around 43% relative air humidity and 25° C., the formulations specified above further show small MMAD values (around 4.1 to 3.5 µm) and a high fine particle fraction (around 62.3 to 67.3%).

Through variation in the spray drying conditions, powders which preferably have a particle size (MMD) of less than 20 µm, preferably less than 10 µm, can be produced. According to a particularly preferred embodiment form, these particles according to the invention have a particle size of less than 7.5 µm, preferably less than 5 µm. Particularly preferred are particles with a particle size of less than 4 µm, and further preferably less than 3.5 µm. Particles with a particle diameter of 0.1-5 µm, preferably 0.2-4 µm, can also be produced. In a further embodiment form, the corresponding particles are mixed with non-respirable particles, such as e.g. lactose, with a particle size of at least 40 µm. The fraction preferably amounts to at least 15%, further preferably to at least 20%, yet further preferably to at least 30%, yet further preferably to at least 40%, particularly preferably to at least 50 or 60%.

Alongside the median particle size (MMD), the inhalability largely depends on the median aerodynamic particle diameter (MMAD). The particles according to the invention preferably have a MMAD smaller than 10 µm, further preferably smaller than 7.5 µm. Particularly advantageous are particles consisting of particles with a MMAD smaller than 5.5 µm, preferably smaller than 5 µm, yet further preferably smaller than 4.5 µm. The powders described in the examples can be produced with corresponding particle sizes through the combination of optimum spray drying conditions and appropriate selection and concentrations of adjuvants according to the invention. The addition of amino acids and/or tri-peptides particularly leads to improved particle performance with an increased fraction of inhalable particles with a MMAD smaller than 7.5 µm, preferably smaller than 5.5 µm. Through additions of isoleucine and tri-isoleucine being made, inhalable particles with a FPF greater than 28%, preferably greater than 40%, further preferably greater than 50%, and yet further preferably greater than 55% (see EXAMPLES), can be produced.

The powders according to the invention are moreover distinguished by a glass transition temperature of at least 40° C., preferably at least 50° C., further preferably at least 55° C., yet further preferably at least 60° C. Particularly preferred powders have a glass transition temperature of at least 65° C. The glass transition temperature of powders according to the invention generally amounts to 40 to 110° C. The present invention accordingly also concerns powders, preferably spray-dried powders, containing a pharmaceutical active substance and LS90P, LS55P, and Coupling Sugar or Coupling Sugar S, whereby the glass transition temperature amounts to 40° C. and more, preferably to between 45 and 60° C. or higher. According to a further preferred embodiment form, the glass transition temperature amounts to 55° C. and more, preferably to between 55 and 60° C. or higher.

Application of the Spray-Dried Powder

The powders according to the invention are suitable for the production of a medicinal drug, preferably the production of a medicinal inhalant.

Freeze-Dried Powders

Powders can also be alternatively produced by freeze drying with ensuing pulverization (see examples). In the examples given in this context, pulverization was performed in the simplest way conceivable by means of a spatula in the lyophilisation vial. The lyophilisate can also be self-evidently pulverized by suitable mills, such as an attrition mill, ball mill, rod mill, mortar mill, air-jet mill, or other suitable processes (see Bauer, Frömming, Führer, $6^{th}$ edition).

Properties of the Freeze-Dried, Pulverized Dry Powder Formulations

The dry protein-powder formulations produced within the frame of this invention have a residual water content of less than 15% (w/w), usually less than 10% (w/w), and preferably less than 5% (w/w). The freeze-dried protein-powder formulations also preferably have a residual water content of less than 3% (w/w), particularly preferably less than 2% (w/w), and most preferably between 0.2 and 1.5% (w/w). Formulations with a low residual moisture content generally exhibit improved stability during packing and storage. The dry protein-powder formulations according to the invention are moreover especially hygroscopic, ie they tend to absorb moisture from their environment. To avoid this, such powders are usually stored in containers such as blister packs ensuring exclusion of airborne moisture.

The stabilizing effects of the adjuvants described here are able to protect the protein from extreme loadings during freeze drying and storage. Pure protein formulations freeze-dried in the absence of adjuvants form aggregates to a large extent. Process-dependent factors such as heat, shear stress, and denaturation at the air-water interfaces give rise to aggregation (up to around 2.1% aggregates) during freeze drying. In the course of storage, the absence of the stabilizing hydrate shell of proteins gives rise to massive aggregation (around 20.5% aggregates).

The preferred freeze-dried formulations of the invention, in contrast to the pure protein formulations, are able both to reduce the formation of aggregates after freeze drying and to keep this to a very low level even under different storage conditions. Under particularly challenging storage conditions (40° C., 75% relative humidity) of forced storage stability, the freeze-dried and pulverized lyophilisates show clear superiority (aggregates of around 1.2 to around 1.5%) over the pure protein formulations (around 14.5% aggregates) as well as over an analogous reference formulation with mannitol as adjuvant (around 34.0% aggregates).

Formulations which, during relatively short-term storage under particularly destabilizing conditions (one week at 40° C., 75% relative humidity), already have a significant stabilizing effect on the incorporated proteins and stabilize the proteins in the long term under much milder standard storage conditions (e.g. one year dry at around 25° C.).

After freeze drying, pulverization, and equilibration with ensuing four weeks' storage under dry conditions at 40° C. (equilibrated storage stability), the LS55P and Coupling Sugar containing powder formulations are distinguished by low aggregate contents (around 2.6 and 4.6% aggregates), particularly in comparison with pure protein powders (around 15.3% aggregates) and an analogous reference formulation with mannitol as adjuvant (around 11.6% aggregates).

After freeze drying, pulverization, and vacuum drying with ensuing four weeks' storage under dry conditions at 40° C. (vacuum-dried storage stability), the LS55P and Coupling Sugar containing powder formulations are distinguished by low aggregate contents (around 1.2 and 1.5% aggregates), particularly in comparison with pure protein powders (around 14.5% aggregates) and an analogous reference formulation with mannitol as adjuvant (around 6.2% aggregates).

The powders according to the invention are moreover distinguished by a glass transition temperature of at least 40° C., preferably at least 50° C., further preferably at least 55° C. The glass transition temperature of powders according to the invention generally amounts to 40 to 110° C. but may exceed this value in individual cases. The present invention accordingly also concerns powders, preferably freeze-dried and pulverized powders, containing a pharmaceutical active substance and LS90P, LS55P, and Coupling Sugar or Coupling Sugar S, whereby the glass transition temperature amounts to 40° C. and more, preferably to between 45 and 60° C. or higher. According to a further preferred embodiment form, the glass transition temperature amounts to 55° C. and more, preferably to between 55 and 60° C. or to 110° C.

Application of the Dried Powder

The powders according to the invention are suitable for the production of a medicinal drug, preferably the production of a medicinal inhalant.

Delivery of the Powders According to the Invention

The spray-dried powder preparations according to the invention can be basically applied directly as dry powder via so-called dry powder inhalers or else, after reconstitution, in the form of aerosols via so-called atomizers. The inhalation powders according to the invention can then be applied by means of known state-of-the-art inhalers.

Inhalation powders according to the invention can be applied e.g. by means of inhalers that deliver an individual dose from a storage container by means of a metering chamber, as described in U.S. Pat. No. 4,570,630A, or via other apparatuses, as described in DE 36 25 685 A. The inhalation powders according to the invention are preferably filled in capsules (to form so-called inhalettes) that are used in inhalers, as e.g. described in WO 94/28958.

Further examples of suitable inhalers are e.g. given in U.S. Pat. No. 5,458,135, U.S. Pat. No. 5,785,049, or WO 01/00263. Further suitable inhalers are known from WO 97/41031, U.S. Pat. No. 3,906,950, and U.S. Pat. No. 4,013,075. Further dispersion inhalers for dry powder preparations are described in EP 129 985, EP 472 598, EP 467 172, and U.S. Pat. No. 5,522,385.

The inhalation powders according to the invention can be e.g. applied by means of the inhaler known by the proprietary name of Turbuhaler® (AstraZeneca LP) or else by means of inhalers as e.g. published in EP 237 507 A. Other suitable inhalers are the Rotahaler® or the Discus® (both of GlazoSmithKline Corporation), the Spiros™ inhaler (Dura Pharmaceuticals), and the Spinhaler® (Fiscon).

An inhaler particularly preferred for application of the drug combination according to the invention in the form of inhalettes is shown in FIG. 24. This inhaler (Handihaler) for the inhalation of pulverulent drugs in capsules is characterized by a housing 1 containing two windows 2, a deck 3, wherein air inlet openings are located and which is provided with sieve 5 fixed in place via sieve housing 4, an inhalation chamber 6 connected with deck 3, whereon a trigger 9 provided with two ground needles 7 and able to move against a spring 8, a mouthpiece 12 hinged via an axis 10 with housing 1, deck 3, and cap 11, and air holes 13 for adjustment of the flow resistance.

Where the inhalation powders according to the invention in respect of the preferred application specified above are filled in capsules (inhalettes), fill amounts of 1 to 30 mg per capsule are appropriate.

The inhalation powders according to the invention may further be applied as propellant-containing or propellant-free inhalation aerosols. For this purpose, the powders according to the invention are suspended in pressure-liquefiable solvents or solvent mixtures or reconstituted in an aqueous solution. Suitable suspensions or solutions are known from the state-of-the-art. For example, reconstitution is advantageous in physiological solutions with a pH of 3-11, preferably 4-9. Particularly advantageous is reconstitution in an aqueous solution with a pH of 5.5-7.8. The propellant-containing suspensions or solutions for reconstitution of the powders according to the invention may further contain other adjuvants in the form of stabilizers, emulsifiers, surface-active substances, or water-soluble organic solvents. Appropriate substances are known to the expert, being described e.g. in (Bauer, Textbook of Pharmaceutical Technology, Wissenschaft Verlagsgesellschaft GmbH, Stuttgart, 178-184; Adler, 1998, Journal of Pharmaceutical Sciences, 88(2) 199-208). Corresponding inhalation aerosols produced by suspension or reconstitution of the powders according to the invention are also the object of the present invention.

The propellants used to produce the inhalation aerosols according to the invention are also known from the state-of-the-art. Suitable propellants are selected from the group consisting of hydrocarbons, such as n-propane, n-butane, or isobutane, and halogenated hydrocarbons, such as preferably chlorinated and fluorinated derivatives of methane, ethane, propane, butane, cyclopropane, or cyclobutane. The propellants specified above may be used individually or in mixtures thereof. Particularly preferred propellants are halogenated alkane derivatives selected from TG11, TG12, TG134a (1,1,1,2-tetrafluoroethane), TG227 (1,1,1,2,3,3,3-heptafluoropropane), and mixtures thereof, whereby the propellants TG134a, TG227, and mixtures thereof are preferred.

The propellant-containing inhalation aerosols according to the invention may contain up to 5% (w/w) active substance. Aerosols according to the invention e.g. contain 0.002-5% (w/w), 0.01-3% (w/w), 0.015-2% (w/w), 0.1-2% (w/w), 0.5-2% (w/w), or 0.5-1% (w/w) of pharmaceutical active substance. Inhalation aerosols with a corresponding active substance concentration can be prepared in an appropriate quantity of solvent by targeted reconstitution of the powders according to the invention.

The propellant-containing inhalation aerosols according to the invention as specified above can also be applied by means of known state-of-the-art inhalers (MDIs=metred dose inhalers). In this context, reference may be made to the Ventolin® (Ventolin Pharmacy) or to the inhalers described in U.S. Pat. No. 5,320,094 or U.S. Pat. No. 5,672,581. A further aspect of the present invention accordingly concerns medicinal drugs in the form of propellant-containing aerosols as described above in conjunction with one or more inhalers suitable for delivery of these aerosols. The present invention further concerns inhalers characterized in that they contain propellant-containing aerosols according to the invention as described above.

The present invention further concerns cartridges that may be used through being equipped with a suitable valve in a suitable inhaler and which contain the propellant-containing inhalation aerosols according to the invention as specified above. Suitable cartridges and processes for filling these cartridges with the propellant-containing inhalation aerosols according to the invention are known from the state-of-the-art.

The powders according to the invention may further be reconstituted in propellant-free inhalation solutions or suspensions. Corresponding propellant-free inhalation solutions e.g. contain aqueous or alcoholic, preferably ethanolic, solvents, where necessary ethanolic solvents mixed with aqueous solvents. In the case of aqueous/ethanolic solvent mixtures, the relative fraction of ethanol in relation to water is not limited, although the maximum limit is preferably up to 70% (v/v), particularly up to 60% (v/v) ethanol. The residual volume percentages are water. The propellant-free inhalation solutions according to the invention may be mixed with co-solvents and/or other adjuvants as described above. For example, it is possible to use co-solvents containing hydroxyl groups or other polar groups, such as e.g. alcohols, particularly isopropyl alcohol, glycols, particularly propylene glycol, polyethylene glycol, polypropylene glycol, glycol ether, glycerol, polyoxyethylene alcohols, and polyoxyethylene fatty acids. In this context, adjuvants and additives are understood to mean any pharmacologically compatible substance which is not an active substance but which, together with the active substance(s), can be formulated in the pharmacologically suitable solvent in order to enhance the qualities of the active substance formulation. These substances preferably unfold no, or in the context of the therapy being sought, no appreciable or at least no unwanted pharmacological effect. Adjuvants and additives, alongside the surface-active substances, such as e.g. soya lecithin, oleic acid, sorbitane esters, such as polysorbate, polyvinylpyrrolidone, other stabilizers, complexing agents, antioxidants, and/or preservatives which guarantee or prolong the shelf life of the finished drug formulation, include flavourings, vitamins, and/or other additives known from the state-of-the-art. Additives also include pharmacologically harmless salts, such as e.g. sodium chloride, as isotonic agents. Preferred adjuvants include antioxidants such as e.g. ascorbic acid, unless already used to adjust the pH value, vitamin A, vitamin E, tocopherols, and similar vitamins or provitamins occurring in the human organism. Preservatives may be used to protect the formulation from contamination by germs. Suitable preservatives known from the state-of-the-art particularly include cetyl pyridinium chloride, benzalconium chloride, or bezoic acid or bezoates, such as sodium bezoate, at the concentrations known from the state-of-the-art. The preservatives specified above are preferably contained at concentrations of up to 50 mg/100 ml, particularly preferably between 5 and 20 mg/100 ml. The present invention also accordingly concerns propellant-free inhalation aerosols produced by reconstitution of the powders according to the invention.

Particularly suitable for application of the propellant-free inhalation solutions according to the invention are inhalers able to atomize a small quantity of a liquid formulation in the therapeutically necessary dose within a few seconds into a suitable therapeutic aerosol for use in an inhaler. Preferred within the frame of the present invention are atomizers wherein a quantity of less than 100 µL, preferably less than 50 µL, particularly preferably between 10 and 30 µL, active substance solution can be atomized in one stroke to form an aerosol with an average particle size of less than 20 µm, preferably less than 10 µm, in such a way that the inhalable fraction of aerosol already corresponds to the therapeutically efficacious quantity.

Such a device for propellant-free delivery of a dosed quantity of a liquid drug for application in an inhaler is e.g. described in detail in international patent applications WO 91/14468 and WO 97/12687 (particularly in FIGS. 6a and 6b thereof).

Within the frame of the present invention, reference is expressly made to corresponding FIGS. 6a and 6b of WO 97/12687, including the associated parts used in the description. The atomizers (devices) described in this application are also known under the description of Respimat® (Boehringer Ingelheim Pharma). Thanks to its near-cylindrical shape and handy size of less than 9 to 15 cm in length and 2 to 4 cm in width, this device can be carried with the patient at all times. The atomizer sprays a specific volume of drug formulation under high pressures through small nozzles in such a way as to generate inhalable aerosols.

The preferred atomizer basically consists of an upper housing unit, pump housing, nozzle, blocking tensioning mechanism, spring housing, spring, and storage container, characterized in that a pump housing fixed in place in the upper housing unit and carrying, at one end, a nozzle body with the nozzle or nozzle arrangement, a hollow piston with valve body, a power take-off flange wherein the hollow piston is fixed in place and which is located in the upper housing unit, a blocking tensioning mechanism located in the upper housing unit, a spring housing with the spring located therein, which is rotatably mounted on the upper housing unit by means of a pivot bearing, a lower housing unit inserted on the spring housing in the axial direction.

The hollow piston with valve body corresponds to a device published in WO 97/12687. It partially projects into the cylinder of the pump housing and has axial displaceability inside the cylinder. Within the frame of the present invention, reference is made to FIGS. 1-4—particularly to FIG. 3—and to the associated parts used in the description. The hollow piston with valve body, on its high-pressure side at the time of spring tripping, exerts a pressure of 5 to 60 MPa (around 50 to 600 bar), preferably 10 to 60 MPa (around 100 to 600 bar), on the fluid, the metered active substance solution. Volumes of 10 to 50 microliters are preferred. Particularly preferred are volumes of 10 to 20 microliters, particularly a volume of 15 microliters per stroke.

The valve body is preferably arranged at the end of the hollow piston, which faces the nozzle body.

The nozzle in the nozzle body is preferably microstructured, ie produced by microtechnology. Microstructured nozzle bodies are e.g. published in WO 94/07607, to whose contents this specification makes reference, particularly to published FIG. 1 and its description. The nozzle body e.g. consists of two rigidly interconnected plates made of glass and/or silicon, whereof at least one plate incorporates one or more microstructured channels which connect the nozzle inlet side with the nozzle outlet side. Located on the nozzle outlet side is at least one circular and one non-circular opening of 2-10 µm depth and 5-15 µm width, whereby the depth preferably amounts to 4, 5 to 6.5 µm and the length to 7-9 µm. In the case of several nozzle openings, two being preferred, the jet directions of the nozzles in the nozzle body can run parallel to each other, or else they are inclined against each other in the nozzle opening direction. In a nozzle body with at least two nozzle openings on the outlet side, the jet directions can be inclined against each other at an angle of 20-160 degrees. An angle of 60-150 degrees is preferred, particularly 80-100 degrees. The nozzle openings are preferably arranged at a distance of 10-200 µm, more preferably at a distance of 10-100 µm, and particularly preferably at a distance of 30-70 µm. Most preferable is a distance of 50 µm.

The jet directions accordingly converge near the nozzle openings.

The liquid drug preparation engages the nozzle body at an inlet pressure of up to 600 bar, preferably 200 to 300 bar, being atomized to form an inhalable aerosol via the nozzle openings. The preferred particle or droplet sizes of the aerosol range up to 20 µm, preferably 3-10 µm.

The blocking tensioning mechanism incorporates a spring, preferably a cylindrical screw-shaped pressure spring, for storage of mechanical energy. The spring acts on the take-off flange as a resilient member, whose movement is determined by the position of a blocking element. The path of the take-off flange is precisely limited by an upper and lower end stop. The spring is preferably tensioned via a power transmission gear, such as e.g. a screw thrust gear, by an external torque generated during rotation of the upper housing unit against the spring housing in the lower housing unit. In this case, the upper housing unit and take-off flange incorporate a one- or multi-threaded V gear.

The blocking element with engaging blocking surfaces is arranged around the take-off flange in a ring shape. It consists e.g. of an inherently radially elastically deformable ring made of plastic or metal. The ring is arranged in a plane vertical to the atomizer axis. After the spring is tensioned, the blocking surfaces of the blocking element slide into the path of the take-off flange and prevent relaxation of the spring. The blocking element is tripped by means of a button. The tripping button is connected or coupled with the blocking element. To trip the blocking tensioning mechanism, the tripping button is displaced parallel to the ring plane, and preferably into the atomizer, causing the deformable ring to be deformed in the ring plane. Design details of the blocking tensioning mechanism are described in WO 97/20590.

The lower housing unit is slid in the axial direction over the spring housing and covers the bearing, spindle drive, and fluid storage container.

During operation of the atomizer, the upper housing unit is rotated against the lower housing unit, whereby the lower housing unit picks up the spring housing. The spring is then compressed and tensioned by the screw thrust gear, and the blocking mechanism automatically engages. The angle of rotation is preferably an integer fraction of 360 degrees, such as e.g. 180 degrees. Simultaneously as the spring is tensioned, the take-off unit in the upper housing unit is displaced over a preset path, and the hollow piston is retracted inside the cylinder in the pump housing, whereby a partial quantity of the fluid is drawn from the storage container into the high-pressure space ahead of the nozzle.

Several interchangeable storage containers containing fluid to be atomized can be where necessary consecutively inserted in the atomizer and used. The storage container contains the aqueous aerosol preparation according to the invention.

The atomization process is started through the tripping button being lightly pressed. The blocking mechanism then vacates the path for the drive unit. The tensioned spring slides the piston into the cylinder of the pump housing. The fluid emerges from the atomizer nozzle in atomized form.

Further design details are published in PCT applications WO 97/12683 and WO 97/20590, to whose contents reference is made.

The atomizer components are made of a functionally suitable material. The atomizer housing and—insofar as function allows—other parts as well are preferably made of plastic, e.g. produced by injection moulding. For medical purposes, physiologically safe materials are used.

FIGS. 6 a/b of WO 97/12687, including the associated description, to whose contents reference is again made in this context, shows a corresponding atomizer (Respimat®). This atomizer is particularly suitable for application of the propellant-free inhalation aerosols according to the invention.

FIG. 6a of WO 97/12687 shows a longitudinal section through the atomizer with the spring tensioned, and FIG. 6b of WO 97/12687 shows a longitudinal section through the atomizer with the spring relaxed. The upper housing unit (51) incorporates the pump housing (52), at whose end the holder (53) for the atomizer nozzle is arranged. The nozzle body (54) and a filter (55) are located in the holder. The hollow piston (57) fixed in the take-off flange (56) of the blocking tensioning mechanism to some extent projects into the cylinder of the pump housing. At its end, the hollow piston carries the valve body (58). The hollow piston is sealed by means of the seal (59). Located inside the upper housing unit is the end stop (60) whereon the take-off flange bears when the spring is relaxed. Located on the take-off flange is the end stop (61) whereon the take-off flange bears when the spring is tensioned. After the spring is tensioned, the blocking element (62) slides between the end stop (61) and a support (63) in the upper housing unit. The tripping button (64) connects with the blocking element. The upper housing unit terminates in the mouthpiece (65) and is sealed by the insertable protective cap (66). The spring housing (67) with pressure spring (68) is rotatably mounted on the upper housing unit by means of the snap lugs (69) and pivot bearing. The lower housing unit (70) is slid over the spring housing. The interchangeable storage container (71) for the fluid to be atomized (72) is located inside the spring housing. The storage container is sealed by the stopper (73), through which the hollow piston projects into the storage container and immerses in the fluid (supply of active substance solution) with its end. The spindle (74) for the mechanical counter is arranged in the spring housing casing. The drive pinion (75) is located at the end of the spindle that faces the upper housing unit. The slider (76) is seated on the spindle.

Where the formulation according to the invention is atomized by means of the technology (Respimat®) described above, the delivered weight during at least 97%, preferably at least 98%, of all inhaler actuations (strokes) should correspond to a specific quantity with a tolerance range of max 25%, preferably 20%, of this quantity. Between 5 and 30 mg formulation as specific weight, particularly preferably between 5 and 20 mg, should preferably be delivered per stroke.

The formulation according to the invention, however, may also be atomized by means of inhalers other than those described above, such as e.g. jet-stream inhalers or other stationary atomizers.

A further aspect of the present invention accordingly concerns medicinal drugs in the form of propellant-free inhalation solutions or suspensions as described above in conjunction with a device suitable for delivery of these formulations, preferably in conjunction with the Respimat®. The present invention preferably targets propellant-free inhalation solutions or suspensions containing one of the powders according to the invention in conjunction with the device known under the description of Respimat®. The present invention further concerns inhalation devices specified above, preferably the Respimat®, characterized in that it contains the propellant-free inhalation solutions or suspensions described above.

Inhalation solutions containing one of the powders according to the invention as described in this context in a unique commercially available form preferably accord with the invention.

The propellant-free inhalation solutions or suspensions according to the invention may, alongside the solutions and suspensions envisaged as described above for application in the Respimat®, may also be used as concentrates or sterile ready-to-use inhalation solutions or suspensions. Through addition of isotonic cooking salt solutions, ready-to-use formulations can be e.g. generated from concentrates. Sterile ready-to-use formulations can be applied by means of power-driven stationary or transportable atomizers that produce inhalable aerosols by means of ultrasound or compressed air according to the venturi principle or other principles.

A further aspect of the present invention accordingly concerns medicinal drugs in the form of propellant-free inhalation solutions or suspensions as described above which are used as concentrates or sterile ready-to-use formulations in conjunction with a device suitable for delivery of these solutions, characterized in that this device refers to a power-driven stationary or transportable atomizer that produces inhalable aerosols by means of ultrasound or compressed air according to the venturi principle or other principles.

Other suitable atomizers for application of reconstituted aerosols in an inhaler are the AERx™ (Aradigm), the Ultravent® (Mallinkrodt), and the Aconll® (Maquest Medical Products).

EMBODIMENT EXAMPLES

Materials and Methods

Materials

A humanized monoclonal antibody with a molecular weight of around 148 kDa of Boehringer Ingelheim, Germany was used as IgG1. The antibody is derived from a murine antibody wherein the complementary-determining regions of the murine antibody were transferred to a human antibody framework. This produced a chimeral antibody with a 95% human and 5% murine fraction. The antibody was expressed from murine myeloma cell strains. The cells are removed with the aid of tangential flow microfiltration and the cell-free solution cleansed by various chromatographic methods. Further steps include nuclease treatment, treatment at low pH value, and nanofiltration. The antibody-containing bulk solution contained 25 mM histidine and 1.6 mM glycine as buffer and was concentrated to around 100 mg/ml by diafiltration for production of the spray drying solution. The bulk for production of the solution to be sprayed contained 0.4 to 0.8% aggregates. The finished drug can be kept for at least two years at 2-8° C. Nyuka-Oligo® LS55P, Nyuka-Oligo® LS90P, Coupling Sugar®, and Coupling Sugar S® were supplied by Hayashibara Shoji Inc, Japan. Saccharose, lactose, mannitol, raffinose, hydroxyethyl starch, and L-isoleucine were supplied by Sigma-Aldrich Chemie GmbH, Germany. Trehalose was procured from Georg Breuer GmbH, Germany. Tri-isoleucine was supplied by Iris Biotech GmbH, Germany. Egg white lysozyme (135500 U/mg) was supplied by SERVA Electrophoresis GmbH, Germany. Synthetic salmon calcitonin (calcitonin) was supplied by Biotrend Chemikalien GmbH, Germany.

Spray Drying with Büchi B-290

Spray drying was performed with the aid of a type B-290 Büchi Mini Spray Dryer of Büchi Labortechnik GmbH. Spray drying of the formulations was basically performed in accordance with the description given in "Spray Drying Handbook", $5^{th}$ edition, K. Masters, John Wiley and Sons, Inc., NY, N.Y. (1991):

The sprayer dryer is built from a heating system, a filter, an aspirator, a drying system, a cyclone, temperature sensors for measurement of the inlet and outlet temperature, and a collecting vessel. A peristaltic pump is used to pump the solution to be sprayed into a twin-substance nozzle, where compressed air is used to atomize the solution into small droplets. Drying proceeds in the spraying tower by warmed air, which is drawn through the spraying tower by the aspirator in a continuous flow process. The product is collected in the collecting vessel after passing through the cyclone. Two different cyclones were used:

Cyclone I: Büchi cyclone (serial number 4189)

Cyclone II: Büchi high-performance cyclone (serial number 46369)

The solids fraction of the sprayed solutions was 10% (w/v), 3.33%, and 2.00% in 50 to 600 ml. The inlet temperature was around 170 to 185° C., the liquid feed rate around 3 to 3.33 ml/min, the aspirator flow rate around 36.8 to 38.3 $m^3$/h, and the atomizing rate (AAF=atomizing air flow) around 0.67 $m^3$/h, 1.05 $m^3$/h, and 1.74 $m^3$/h, resulting in an outlet temperature of around 80-95° C.

Freeze Drying

Freeze drying was performed with the aid of a type Christ LPC-16/NT Epsilon 2-12 D freeze dryer of Martin Christ Gefriertrocknungsanlagen GmbH. The freeze dryer consists of a drying chamber, a condenser for separation of the sublimated solvent, a pump for vacuum generation, and electrical equipment. Drying is controlled via the control surface temperature and drying chamber vacuum.

The solids fraction of the freeze drying solution was 5% (w/v). The solution was portioned in 2R vials containing 0.5 ml each and placed in the freeze dryer with threaded freeze drying stoppers. The solutions were initially frozen at −40° C.×30 minutes. This was followed by main drying at 0.11 mbar in three steps: first −40° C.×30 hours, then −30° C.×8 hours, and finally −16° C.×8 hours. The next step was after-drying, which proceeded at 20° C.×20 hours×0.001 mbar. As a final step, the vials were automatically sealed with the freeze drying stoppers only inserted at the start. The thus obtained lyophilisates have been pulverized with a spatula inside the vials.

X-Ray Diffractometry (Wide-Angle X-Ray Diffractometry (WAXS))

To determine the crystallinity of the dried samples, the samples were investigated with a type XRD 3000 TT X-ray diffractometer (of Seifert, Ahrensburg, Germany) in a room attemperated to 22° C. The Cu anode X-ray tube using Cu-Kα radiation with λ=0.15418 mm (Ni primary filter) was operated at an anodic voltage of 40 kV and current intensity of 30 mA. After the sample plate was placed in the instrument, the sample was measured over the 5 to 40° range at a scanning rate of 2θ=0.05° and measurement time of 2 seconds at each angle.

The powder diffractograms were recorded with the aid of the ScanX-Rayflex version 3.07, device XRD 3000 (Scan) and the Rayflex version 2.1, 1996 (analysis) on a type SC 1000 V detector.

Size Exclusion Chromatography (SEC-HPLC)

a) IgG1 Protein Aggregates

To quantify the IgG1 protein aggregates in the reconstituted powders, a SEC-HPLC was performed. The SEC-HPLC was performed with a type HP1090 unit of Agilent. A type TSK3000SWXL column (300×7.8 mm) of Tosoh Biosep (Tosoh Bioscience, Stuttgart, Germany) was used for separation. As the fluid, a buffer consisting of 0.1M disodium hydrogen phosphate dihydrate and 0.1M sodium sulphate was dehydrated and adjusted with 85% ortho-phosphoric acid to pH 6.8. The amount of sample charged was 25 μl at a protein concentration of 2-10 mg/ml. Protein detection was performed at 280 nm with the aid of a diode array detector of Agilent. HP Chemstation software of Agilent was used to evaluate the chromatograms.

b) Calcitonin Protein Aggregates

To quantify the calcitonin protein aggregates in the reconstituted powders, a SEC-HPLC was performed. The SEC-HPLC was performed with a type HP1100 unit of Agilent. A type TSK2000SWXL column (300×7.8 mm) of Tosoh Biosep (Tosoh Bioscience, Stuttgart, Germany) was used for separation. As the fluid, a buffer consisting of 0.25 sodium sulphate with a pH of around 6 was used (Windisch et al., 1997). Alternatively, a dehydrated buffer consisting of 0.1M disodium hydrogen phosphate dihydrate and 0.1M sodium sulphate adjusted with 85% ortho-phosphoric acid to pH 6.8 can be used. The amount of sample charged was 20 μl at a protein concentration of 0.5-2 mg/ml. Protein detection was performed at 210 nm with the aid of a UV detector of Agilent. HP Chemstation software of Agilent was used to evaluate the chromatograms.

c) Lysozyme Residual Monomer Content

To quantify the lysozyme residual monomer content in the reconstituted lysozyme formulations, a modified SEC-HPLC (van de Weert, 2000) was performed. A type TSK2000SWXL column (300×7.8 mm) of Tosoh Biosep (Tosoh Bioscience, Stuttgart, Germany) was used for separation. As the fluid, a buffer consisting of 0.1M disodium hydrogen phosphate dihydrate and 0.2M sodium chloride was adjusted with 85% ortho-phosphoric acid to pH 7.0. The amount of sample charged was 25 μl at a protein concentration of 2-10 mg/ml. Protein detection was performed at 280 nm with the aid of a diode array detector of Agilent. HP Chemstation software of Agilent was used to evaluate the chromatograms.

To evaluate the formulations, the residual soluble monomer was quantified by the following method. A calibration line was initially produced with lysozyme standard solutions with concentrations of 2.5 mg/ml, 5.0 mg/ml, and 10 mg/ml.

Consideration was then given to the AUC of the monomer peaks in relation to the corresponding lysozyme concentrations in the investigated standard solutions.

The residual monomer content of the different investigated lysozyme formulations was calculated on the basis of the calibration lines. The higher the residual monomer content of a formulation, the better is the protein stability.

Particle Size Determination (MMD)

The mass median diameter (MMD) or the median particle size was determined with the aid of the Sympatech Helos unit of Sympatech GmbH, Clausthal-Zellerfeld, Germany. The measurement principle is based on laser diffraction, a helium-neon laser being used. Some 1-3 mg powder are dispersed at an air pressure of 2 bar and guided in front of a 50 mm Fourier lens by a parallel laser beam. The particle size distribution is evaluated with a Fraunhofer model. Two measurements were performed per powder.

Mass Median Aerodynamic Diameter (MMAD) and Fine Particle Fraction (FPF)

Some 12-18 mg powder respectively filled in size 3 hard-gelatin capsules and introduced into the Handihaler (powder inhaler of Boehringer Ingelheim) were used for the measurements. An adapter was used to couple the Handihaler to the USP EP throat of the instrument impactor inlet. The powder was drawn off at a rate of 39.0 l/min at a suction time of 6.15 seconds. The air throughput was controlled via an external control panel. At least three capsules were measured for each powder.

The APS 3321 unit of TSI Inc., MN, USA was simultaneously used in combination with the impactor inlet 3306 to determine the aerodynamic particle size (mass median aerodynamic diameter, MMAD) via a time of flight determination and the fine particle fraction (FPF) via a single-stage impactor (with an effective cut-off diameter of 5.0 µm at 39 L/min). After being drawn off via the EP/USP throat or sample induction port, the powder passes to a thin capillary, where 0.2% of the powder quantity is sampled for time of flight measurement under isokinetic conditions. The time of flight measurement is performed after capillary passage through two laser beams, which, as in a light barrier, detect the flight times over a specific distance. The result is a numerical distribution that is subsequently converted into a mass distribution and then to the mass median aerodynamic diameter (MMAD).

The residual 99.8% of the powder population that has passed by the capillary is separated via the single-stage impactor. The fraction greater than 5.0 µm separates in the impactor on an impact plate as a result of mass inertia. The fine particle fraction (FPF) follows the airflow, being finally separated in a depth filter. The fine particle fraction is gravimetrically determined. The fine particle fraction is calculated from the fraction of powder separated in the filter in relation to the total quantity of powder used, ie the weighed powder per capsule.

Residual Water Content

The residual water content of the dried products was determined by means of coulometric titration (Metrohm 737 KF coulometer with type 703 titration stand, Germany). To determine the residual water content, powder was dissolved or dispersed in methanol (Hydranal—Methanol dry, VWR/Merck Eurolab). The measured solution (Hydranal—Coulomat solution, VWR/Merck Eurolab) of the Metrohm coulometer was conditioned at the start of the measurements, ie the measured solution was calibrated to zero water content. The sample was injected into the titration cell and measured.

Stability Determination

The powders or proteins contained in the powder were investigated for different stabilities after spray drying. The percentage fraction of protein aggregates was set at the measurement unit for formulation stability. Pure protein formulations, analogous trehalose formulations, analogous raffinose formulations, analogous saccharose formulations, analogous saccharose-lactose formulations, or analogous hydroxyethyl starch formulations were partially compared as references with the innovative adjuvants described in the invention. Aggregates were analyzed by validated size exclusion chromatography (SEC-HPLC) with UV detection (DAD). For this purpose, the pretreated powders were initially reconstituted in purest water (with a pH of 6 to 8).

Forced storage stability: Selected formulations were investigated for stability after one week's open storage at around 40° C. and around 75% relative air humidity (40° C., 75% RH) in open glass vials.

Equilibrated storage stability: Selected formulations after spray drying were stored in open glass vials for one day at around 22° C. and 50 to 55% relative air humidity (equilibration). The glass vials were subsequently sealed and beaded under the conditions specified above and investigated for stability after four weeks' dry storage at around 40° C.

Vacuum-dried storage stability: Selected formulations after spray drying were stored for one day in open glass vials in a vacuum drying cabinet of Memmert, Germany at around 30° C. and around 0.15 mbar (vacuum drying). The glass vials were subsequently removed from the vacuum drying cabinet, sealed, and beaded and investigated for stability after four weeks' dry storage at around 40° C.

3 months' stability: Selected formulations after spray drying were vacuum-dried in open glass vials (see above). The glass vials were sealed and beaded under nitrogen and stored at three different temperatures of 2-8° C., 25° C., and 40° C. The powders were investigated for stability after one month.

Open 3 months' stability: Selected formulations after spray drying were respectively stored in open glass vials at 25° C. and around 29% and/or 43% relative air humidity. The powders were investigated for stability after one and three months. For selected formulations. the aerodynamic performance of the powder was also determined by means of time of flight measurements (see above).

Example 1

Spray Drying of a 10% (w/v) IgG1 Formulation

Pure IgG1 with a concentration of around 109 mg/ml formulated in a pH 6 glycine-histidine buffer (see Materials) was diluted with demineralized water (with a pH of around 7.5) to a content of 100 mg/ml and, in the absence of any other adjuvants, spray-dried as described above with application of cylone I at an atomizing air flow of around 0.67 m³/h. The solution volume was 50 ml. The aggregate content was investigated as described above.

After one week's open storage at 75% relative air humidity and 40° C. (forced storage stability), the solution prepared from the reconstituted powder had around 18.9% and 18.2% aggregates respectively.

After one day's equilibration and four weeks' dry storage at 40° C., the solution prepared from the reconstituted powder had around 11.8% aggregates.

After one day's vacuum drying and four weeks' dry storage at 40° C., the solution prepared from the reconstituted powder had around 13.2% aggregates.

Spray Drying of a 3.33% (w/v) IgG1 Formulation

Pure IgG1 with a concentration of around 102.8 mg/ml formulated in a pH 6 glycine-histidine buffer (see Materials) was diluted with demineralized water (with a pH of around 7.5) to a content of 33 mg/ml and, in the absence of any other adjuvants, spray-dried as described above with application of cylone I at an atomizing air flow of around 0.67 m$^3$/h. The solution volume was 150 ml. The aggregate content was investigated as described above.

After one week's open storage at 75% relative air humidity and 40° C. (forced storage stability), the solution prepared from the reconstituted powder had around 16.3% aggregates.

After 1 and 3 months' storage at 2-8° C. (3 months' stability), the solution prepared from the reconstituted powder had around 4.5% and 4.4% aggregates respectively.

After 1 and 3 months' storage at 25° C. (3 months' stability), the solution prepared from the reconstituted powder had around 7.4% and 7.1% aggregates respectively.

After 1 and 3 months' storage at 40° C. (3 months' stability), the solution prepared from the reconstituted powder had around 13.3% and 18.1% aggregates respectively.

After 1 and 3 months' storage at around 29% relative air humidity and 25° C., the solution prepared from the reconstituted powder had around 5.5% and 6.6% aggregates respectively.

After 1 and 3 months' storage at around 43% relative air humidity and 25° C., the solution prepared from the reconstituted powder had around 5.6% and 7.0% aggregates respectively.

Spray Drying of a 9% (w/v) Trehalose 1% (w/v) IgG1 Formulation 4.5 g trehalose were dissolved in around 40 ml demineralized water (with a pH of around 7.5). As the next step, around 4.6 ml pure IgG1 with a concentration of around 109 mg/ml formulated in a pH 6 glycine-histidine buffer (see Materials) were added and diluted with demineralized water (with a pH of around 7.5) to a volume of 50 ml. The thus obtained solution contained around 9% (w/v) adjuvant or matrix and 1% (w/v) protein and was spray-dried as described above with application of cylone I at an atomizing air flow of around 0.67 m$^3$/h. The aggregate content was investigated as described above.

The following aggregate contents were obtained for its storage stability:

After one week's open storage at 75% relative air humidity and 40° C. (forced storage stability), the solution prepared from the reconstituted powder had around 12.6% aggregates.

Spray Drying of a 3.00% (w/v) LS90P 0.33% (w/v) IgG1 Formulation 4.5 g LS90P were dissolved in around 140 ml demineralized water (with a pH of around 7.5). As the next step, around 4.864 ml pure IgG1 with a concentration of around 102.8 mg/ml formulated in a pH 6 glycine-histidine buffer (see Materials) were added and diluted with demineralized water (with a pH of around 7.5) to a volume of 150 ml. The thus obtained solution contained around 3.00% (w/v) adjuvant or matrix and 0.33% (w/v) protein and was spray-dried as described above with application of cylone I at an atomizing air flow of around 0.67 m$^3$/h. The aggregate content was investigated as described above.

The following aggregate contents were obtained for its storage stability:

After one week's open storage at 75% relative air humidity and 40° C. (forced storage stability), the solution prepared from the reconstituted powder had around 1.0% aggregates.

After 1 and 3 months' storage at 2-8° C. (3 months' stability), the solution prepared from the reconstituted powder had around 0.6% and 0.9% aggregates respectively.

After 1 and 3 months' storage at 25° C. (3 months' stability), the solution prepared from the reconstituted powder had around 0.8% and 1.3% aggregates respectively.

After 1 and 3 months' storage at 40° C. (3 months' stability), the solution prepared from the reconstituted powder had around 1.1% and 2.2% aggregates respectively.

The MMD of the powder was determined as described above.

The MMD of the powder after spray drying was 2.8 μm.

The MMAD and FPF of the powder were determined as described above.

The MMAD of the powder after spray drying was 3.8 μm, and the FPF was 23.6% in relation to the powder capsule weight.

Spray Drying of a 9.9% (w/v) LS55P 0.1% (w/v) IgG1 Formulation 4.950 g LS55P were dissolved in around 40 ml demineralized water (with a pH of around 7.5). As the next step, around 0.518 ml pure IgG1 with a concentration of around 96.55 mg/ml formulated in a pH 6 glycine-histidine buffer (see Materials) were added and diluted with demineralized water (with a pH of around 7.5) to a volume of 50 ml. The thus obtained solution contained around 9.9% (w/v) adjuvant or matrix and 0.1% (w/v) protein and was spray-dried as described above with application of cylone I at an atomizing air flow of around 0.67 m$^3$/h. The aggregate content was investigated as described above.

The following aggregate contents were obtained for its storage stability:

After one week's open storage at 75% relative air humidity and 40° C. (forced storage stability), the solution prepared from the reconstituted powder had around 5.7% aggregates.

After one day's vacuum drying and four weeks' dry storage at 40° C., the solution prepared from the reconstituted powder had around 4.7% aggregates.

Spray Drying of a 9% (w/v) LS55P 1% (w/v) IgG1 Formulation 4.5 g LS55P were dissolved in around 40 ml demineralized water (with a pH of around 7.5). As the next step, around 4.6 ml pure IgG1 with a concentration of around 109 mg/ml formulated in a pH 6 glycine-histidine buffer (see Materials) were added and diluted with demineralized water (with a pH of around 7.5) to a volume of 50 ml. The thus obtained solution contained around 9% (w/v) adjuvant or matrix and 1% (w/v) protein and was spray-dried as described above with application of cylone I at an atomizing air flow of around 0.67 m$^3$/h. The aggregate content was investigated as described above.

The following aggregate contents were obtained for its storage stability:
- After one week's open storage at 75% relative air humidity and 40° C. (forced storage stability), the solution prepared from the reconstituted powder had around 2.3% aggregates.
- After one day's equilibration and four weeks' dry storage at 40° C., the solution prepared from the reconstituted powder had around 1.8% aggregates.
- After one day's vacuum drying and four weeks' dry storage at 40° C., the solution prepared from the reconstituted powder had around 1.4% aggregates.

Spray Drying of a 6% (w/v) LS55P 4% (w/v) IgG1 Formulation 3.0 g LS55P were dissolved in around 15 ml demineralized water (with a pH of around 7.5). As the next step, around 19.45 ml pure IgG1 with a concentration of around 102.8 mg/ml formulated in a pH 6 glycine-histidine buffer (see Materials) were added and diluted with demineralized water (with a pH of around 7.5) to a volume of 50 ml. The thus obtained solution contained around 6% (w/v) adjuvant or matrix and 4% (w/v) protein and was spray-dried as described above with application of cylone I at an atomizing air flow of around 0.67 m$^3$/h. The aggregate content was investigated as described above.

The following aggregate contents were obtained for its storage stability:
- After one week's open storage at 75% relative air humidity and 40° C. (forced storage stability), the solution prepared from the reconstituted powder had around 4.0% aggregates.

Spray Drying of a 4% (w/v) LS55P 6% (w/v) IgG1 Formulation 2.0 g LS55P were dissolved in around 15 ml demineralized water (with a pH of around 7.5). As the next step, around 29.18 ml pure IgG1 with a concentration of around 102.8 mg/ml formulated in a pH 6 glycine-histidine buffer (see Materials) were added and diluted with demineralized water (with a pH of around 7.5) to a volume of 50 ml. The thus obtained solution contained around 4% (w/v) adjuvant or matrix and 6% (w/v) protein and was spray-dried as described above with application of cylone I at an atomizing air flow of around 0.67 m$^3$/h. The aggregate content was investigated as described above.

The following aggregate contents were obtained for its storage stability:
- After one week's open storage at 75% relative air humidity and 40° C. (forced storage stability), the solution prepared from the reconstituted powder had around 6.9% aggregates.

Spray Drying of a 2.5% (w/v) LS55P 7.5% (w/v) IgG1 Formulation 1.25 g LS55P were dissolved in around 10 ml demineralized water (with a pH of around 7.5). As the next step, around 38.84 ml pure IgG1 with a concentration of around 96.55 mg/ml formulated in a pH 6 glycine-histidine buffer (see Materials) were added and diluted with demineralized water (with a pH of around 7.5) to a volume of 50 ml. The thus obtained solution contained around 2.5% (w/v) adjuvant or matrix and 7.5% (w/v) protein and was spray-dried as described above with application of cylone I at an atomizing air flow of around 0.67 m$^3$/h. The aggregate content was investigated as described above.

The following aggregate contents were obtained for its storage stability:
- After one week's open storage at 75% relative air humidity and 40° C. (forced storage stability), the solution prepared from the reconstituted powder had around 5.9% aggregates.
- After one day's vacuum drying and four weeks' dry storage at 40° C., the solution prepared from the reconstituted powder had around 6.1% aggregates.

Spray Drying of a 1.0% (w/v) LS55P 9.0% (w/v) IgG1 Formulation 0.50 g LS55P was dissolved in around 5 ml demineralized water (with a pH of around 7.5). As the next step, around 41.43 ml pure IgG1 with a concentration of around 96.55 mg/ml formulated in a pH 6 glycine-histidine buffer (see Materials) were added and diluted with demineralized water (with a pH of around 7.5) to a volume of 50 ml. The thus obtained solution contained around 1.0% (w/v) adjuvant or matrix and 9.0% (w/v) protein and was spray-dried as described above with application of cylone I at an atomizing air flow of around 0.67 m$^3$/h. The aggregate content was investigated as described above.

The following aggregate contents were obtained for its storage stability:
- After one week's open storage at 75% relative air humidity and 40° C. (forced storage stability), the solution prepared from the reconstituted powder had around 10.8% aggregates.
- After one day's vacuum drying and four weeks' dry storage at 40° C., the solution prepared from the reconstituted powder had around 8.0% aggregates.

Spray Drying of a 0.5% (w/v) LS55P 9.5% (w/v) IgG1 Formulation 0.25 g LS55P was dissolved in around 2.5 ml demineralized water (with a pH of around 7.5). As the next step, around 46.21 ml pure IgG1 with a concentration of around 102.8 mg/ml formulated in a pH 6 glycine-histidine buffer (see Materials) were added and diluted with demineralized water (with a pH of around 7.5) to a volume of 50 ml. The thus obtained solution contained around 0.5% (w/v) adjuvant or matrix and 9.5% (w/v) protein and was spray-dried as described above with application of cylone I at an atomizing air flow of around 0.67 m$^3$/h. The aggregate content was investigated as described above.

The following aggregate contents were obtained for its storage stability:
- After one week's open storage at 75% relative air humidity and 40° C. (forced storage stability), the solution prepared from the reconstituted powder had around 13.7% aggregates.

Spray Drying of a 3.00% (w/v) LS55P 0.33% (w/v) IgG1 Formulation 9.0 g LS55P were dissolved in around 280 ml demineralized water (with a pH of around 7.5). As the next step, around 9.73 ml pure IgG1 with a concentration of around 102.8 mg/ml formulated in a pH 6 glycine-histidine buffer (see Materials) were added and diluted with demineralized water (with a pH of around 7.5) to a volume of 300 ml. The thus obtained solution contained around 3.0% (w/v) adjuvant or matrix and 0.33% (w/v) protein and was spray-dried as described above with application of cylone II at an atomizing air flow of around 0.67 m³/h. The aggregate content was investigated as described above.

The following aggregate contents were obtained for its storage stability:

After one week's open storage at 75% relative air humidity and 40° C. (forced storage stability), the solution prepared from the reconstituted powder had around 5.0% aggregates.

The MMD of the powder was determined as described above.

The MMD of the powder after spray drying was 2.9 µm.

The MMAD and FPF of the powder were determined as described above.

The MMAD of the powder after spray drying was 4.3 µm, and the FPF was 15.9% in relation to the powder capsule weight.

Spray Drying of a 9.9% (w/v) Coupling Sugar 0.1% (w/v) IgG1 Formulation 6.290 g Coupling Sugar-containing syrup (equivalent to 4.950 g Coupling Sugar) were dissolved in around 40 ml demineralized water (with a pH of around 7.5). As the next step, around 0.518 ml pure IgG1 with a concentration of around 96.55 mg/ml formulated in a pH 6 glycine-histidine buffer (see Materials) were added and diluted with demineralized water (with a pH of around 7.5) to a volume of 50 ml. The thus obtained solution contained around 9.9% (w/v) adjuvant or matrix and 0.1% (w/v) protein and was spray-dried as described above with application of cylone I at an atomizing air flow of around 0.67 m³/h. The aggregate content was investigated as described above.

The following aggregate contents were obtained for its storage stability:

After one week's open storage at 75% relative air humidity and 40° C. (forced storage stability), the solution prepared from the reconstituted powder had around 14.9% aggregates.

Spray Drying of a 9% (w/v) Coupling Sugar 1% (w/v) IgG1 Formulation 5.71 g Coupling Sugar-containing syrup (equivalent to 4.5 g Coupling Sugar) were dissolved in around 40 ml demineralized water (with a pH of around 7.5). As the next step, around 4.6 ml pure IgG1 with a concentration of around 109 mg/ml formulated in a pH 6 glycine-histidine buffer (see Materials) were added and diluted with demineralized water (with a pH of around 7.5) to a volume of 50 ml. The thus obtained solution contained around 9% (w/v) adjuvant or matrix and 1% (w/v) protein and was spray-dried as described above with application of cylone I at an atomizing air flow of around 0.67 m³/h. The aggregate content was investigated as described above.

The following aggregate contents were obtained for its storage stability:

After one week's open storage at 75% relative air humidity and 40° C. (forced storage stability), the solution prepared from the reconstituted powder had around 4.9% aggregates.

After one day's equilibration and four weeks' dry storage at 40° C., the solution prepared from the reconstituted powder had around 3.2% aggregates.

After one day's vacuum drying and four weeks' dry storage at 40° C., the solution prepared from the reconstituted powder had around 2.1% aggregates.

Spray Drying of a 6% (w/v) Coupling Sugar 4% (w/v) IgG1 Formulation 3.81 g Coupling Sugar-containing syrup (equivalent to 3.0 g Coupling Sugar) were dissolved in around 25 ml demineralized water (with a pH of around 7.5). As the next step, around 19.45 ml pure IgG1 with a concentration of around 102.8 mg/ml formulated in a pH 6 glycine-histidine buffer (see Materials) were added and diluted with demineralized water (with a pH of around 7.5) to a volume of 50 ml. The thus obtained solution contained around 6% (w/v) adjuvant or matrix and 4% (w/v) protein and was spray-dried as described above with application of cylone I at an atomizing air flow of around 0.67 m³/h. The aggregate content was investigated as described above.

The following aggregate contents were obtained for its storage stability:

After one week's open storage at 75% relative air humidity and 40° C. (forced storage stability), the solution prepared from the reconstituted powder had around 5.0% aggregates.

Spray Drying of a 4% (w/v) Coupling Sugar 6% (w/v) IgG1 Formulation 2.54 g Coupling Sugar-containing syrup (equivalent to 2.0 g Coupling Sugar) were dissolved in around 15 ml demineralized water (with a pH of around 7.5). As the next step, around 29.18 ml pure IgG1 with a concentration of around x mg/ml formulated in a pH 6 glycine-histidine buffer (see Materials) were added and diluted with demineralized water (with a pH of around 7.5) to a volume of 50 ml. The thus obtained solution contained around 4% (w/v) adjuvant or matrix and 6% (w/v) protein and was spray-dried as described above with application of cylone I at an atomizing air flow of around 0.67 m³/h. The aggregate content was investigated as described above.

The following aggregate contents were obtained for its storage stability:

After one week's open storage at 75% relative air humidity and 40° C. (forced storage stability), the solution prepared from the reconstituted powder had around 9.9% aggregates.

Spray Drying of a 2.5% (w/v) Coupling Sugar 7.5% (w/v) IgG1 Formulation 1.59 g Coupling Sugar-containing syrup (equivalent to 1.250 g Coupling Sugar) was dissolved in around 8 ml demineralized water (with a pH of around 7.5). As the next step, around 38.84 ml pure IgG1 with a concentration of around 96.56 mg/ml formulated in a pH 6 glycine-histidine buffer (see Materials) were added and diluted with demineralized water (with a pH of around 7.5) to a volume of 50 ml. The thus obtained solution contained around 2.5% (w/v) adjuvant or matrix and 7.5% (w/v) protein and was spray-dried as described above with application of cylone I at an atomizing air flow of around 0.67 m³/h. The aggregate content was investigated as described above.

The following aggregate contents were obtained for its storage stability:

After one week's open storage at 75% relative air humidity and 40° C. (forced storage stability), the solution prepared from the reconstituted powder had around 10.8% aggregates.

Spray Drying of a 1.0% (w/v) Coupling Sugar 9.0% (w/v) IgG1 Formulation 0.653 g Coupling Sugar-containing syrup (equivalent to 0.50 g Coupling Sugar) was dissolved in around 5 ml demineralized water (with a pH of around 7.5). As the next step, around 41.43 ml pure IgG1 with a concentration of around 96.56 mg/ml formulated in a pH 6 glycine-histidine buffer (see Materials) were added and diluted with demineralized water (with a pH of around 7.5) to a volume of 50 ml. The thus obtained solution contained around 1.0% (w/v) adjuvant or matrix and 9.0% (w/v) protein and was spray-dried as described above with application of cylone I at an atomizing air flow of around 0.67 m³/h. The aggregate content was investigated as described above.

The following aggregate contents were obtained for its storage stability:

After one week's open storage at 75% relative air humidity and 40° C. (forced storage stability), the solution prepared from the reconstituted powder had around 13.1% aggregates.

Spray Drying of a 9% (w/v) Coupling Sugar S 1% (w/v) IgG1 Formulation 5.86 g Coupling Sugar S-containing syrup (equivalent to 4.5 g Coupling Sugar S) were dissolved in around 40 ml demineralized water (with a pH of around 7.5). As the next step, around 4.6 ml pure IgG1 with a concentration of around 109 mg/ml formulated in a pH 6 glycine-histidine buffer (see Materials) were added and diluted with demineralized water (with a pH of around 7.5) to a volume of 50 ml. The thus obtained solution contained around 9% (w/v) adjuvant or matrix and 1% (w/v) protein and was spray-dried as described above with application of cylone I at an atomizing air flow of around 0.67 m³/h. The aggregate content was investigated as described above.

The following aggregate contents were obtained for its storage stability:

After one week's open storage at 75% relative air humidity and 40° C. (forced storage stability), the solution prepared from the reconstituted powder had around 5.4% aggregates.

Example 2

Spray Drying of an 8% (w/v) Trehalose 1% (w/v) L-Isoleucine 1% (w/v) IgG1 Formulation 4.0 g trehalose and 0.5 g L-isoleucine were dissolved in around 40 ml demineralized water (with a pH of around 7.5) in an ultrasonic bath. As the next step, around 4.6 ml pure IgG1 with a concentration of around 109 mg/ml formulated in a pH 6 glycine-histidine buffer (see Materials) were added and diluted with demineralized water (with a pH of around 7.5) to a volume of 50 ml. The thus obtained solution contained around 9% (w/v) adjuvant or matrix and 1% (w/v) protein and was spray-dried as described above with application of cylone I at an atomizing air flow of around 0.67 m³/h. The aggregate content was investigated as described above.

After one week's open storage at 75% relative air humidity and 40° C. (forced storage stability), the solution prepared from the reconstituted powder had around 22.2% aggregates.

Spray Drying of a 2.66% (w/v) LS90P 0.33% (w/v) L-Isoleucine 0.33% (w/v) IgG1 Formulation 4.0 g LS90P and 0.50 g L-isoleucine were dissolved in around 140 ml demineralized water (with a pH of around 7.5) in an ultrasonic bath. As the next step, around 4.864 ml pure IgG1 with a concentration of around 102.8 mg/ml formulated in a pH 6 glycine-histidine buffer (see Materials) were added and diluted with demineralized water (with a pH of around 7.5) to a volume of 150 ml. The thus obtained solution contained around 3.00% (w/v) adjuvant or matrix and 0.33% (w/v) protein and was spray-dried as described above with application of cylone II at an atomizing air flow of around 0.67 m³/h. The aggregate content was investigated as described above.

The following aggregate contents were obtained for its storage stability:

After one week's open storage at 75% relative air humidity and 40° C. (forced storage stability), the solution prepared from the reconstituted powder had around 0.7% aggregates.

After 1 and 3 months' storage at 2-8° C. (3 months' stability), the solution prepared from the reconstituted powder had around 0.7% and 1.0% aggregates respectively.

After 1 and 3 months' storage at 25° C. (3 months' stability), the solution prepared from the reconstituted powder had around 0.8% and 1.1% aggregates respectively.

After 1 and 3 months' storage at 40° C. (3 months' stability), the solution prepared from the reconstituted powder had around 0.6% and 1.1% aggregates respectively.

The MMAD and FPF of the powder were determined as described above.

The MMAD of the powder after spray drying was 7.3 μm, and the FPF was 28.1% in relation to the powder capsule weight.

Spray Drying of an 8% (w/v) LS55P 1% (w/v) L-Isoleucine 1% (w/v) IgG1 Formulation 4.00 g LS90P and 0.50 g L-isoleucine were dissolved in around 40 ml demineralized water (with a pH of around 7.5) in an ultrasonic bath. As the next step, around 4.60 ml pure IgG1 with a concentration of around 109 mg/ml formulated in a pH 6 glycine-histidine buffer (see Materials) were added and diluted with demineralized water (with a pH of around 7.5) to a volume of 50 ml. The thus obtained solution contained around 9% (w/v) adjuvant or matrix and 1% (w/v) protein and was spray-dried as described above with application of cylone I at an atomizing air flow of around 0.67 $m^3/h$. The aggregate content was investigated as described above.

After one week's open storage at 75% relative air humidity and 40° C. (forced storage stability), the solution prepared from the reconstituted powder had around 5.5% aggregates.

After one day's equilibration and four weeks' dry storage at 40° C., the solution prepared from the reconstituted powder had around 1.8% aggregates.

After one day's vacuum drying and four weeks' dry storage at 40° C., the solution prepared from the reconstituted powder had around 1.8% aggregates.

Spray Drying of a 2.66% (w/v) LS55P 0.33% (w/v) L-Isoleucine 0.33% (w/v) IgG1 Formulation 8.0 g LS55P and 1 g L-isoleucine were dissolved in around 280 ml demineralized water (with a pH of around 7.5) in an ultrasonic bath. As the next step, around 9.7 ml pure IgG1 with a concentration of around 102.8 mg/ml formulated in a pH 6 glycine-histidine buffer (see Materials) were added and diluted with demineralized water (with a pH of around 7.5) to a volume of 300 ml. The thus obtained solution contained around 3% (w/v) adjuvant or matrix and 0.33% (w/v) protein and was spray-dried as described above with application of cylone II at an atomizing air flow of around 0.67 m³/h. The aggregate content was investigated as described above.

After one week's open storage at 75% relative air humidity and 40° C. (forced storage stability), the solution prepared from the reconstituted powder had around 5.9% aggregates.

After 1 and 3 months' storage at 2-8° C. (3 months' stability), the solution prepared from the reconstituted powder had around 1.6% aggregates respectively.

After 1 and 3 months' storage at 25° C. (3 months' stability), the solution prepared from the reconstituted powder had around 1.6% and 1.8% aggregates respectively.

After 1 and 3 months' storage at 40° C. (3 months' stability), the solution prepared from the reconstituted powder had around 1.6% and 1.8% aggregates respectively.

The MMAD and FPF of the powder were determined as described above.

The MMAD of the powder after spray drying was 4.9 μm, and the FPF was 34.7% in relation to the powder capsule weight.

Spray Drying of an 8% (w/v) Coupling Sugar 1% (w/v) L-Isoleucine 1% (w/v) IgG1 Formulation 5.08 g Coupling Sugar-containing syrup (equivalent to 4.0 g Coupling Sugar) and 0.50 g L-isoleucine were dissolved in around 40 ml demineralized water (with a pH of around 7.5) in an ultrasonic bath. As the next step, around 4.60 ml pure IgG1 with a concentration of around 109 mg/ml formulated in a pH 6 glycine-histidine buffer (see Materials) were added and diluted with demineralized water (with a pH of around 7.5) to a volume of 50 ml. The thus obtained solution contained around 9% (w/v) adjuvant or matrix and 1% (w/v) protein and was spray-dried as described above with application of cylone I at an atomizing air flow of around 0.67 $m^3$/h. The aggregate content was investigated as described above.

After one week's open storage at 75% relative air humidity and 40° C. (forced storage stability), the solution prepared from the reconstituted powder had around 7.1% aggregates.

After one day's equilibration and four weeks' dry storage at 40° C., the solution prepared from the reconstituted powder had around 2.5% aggregates.

After one day's vacuum drying and four weeks' dry storage at 40° C., the solution prepared from the reconstituted powder had around 1.1% aggregates.

Spray Drying of an 8% (w/v) Coupling Sugar S 1% (w/v) L-Isoleucine 1% (w/v) IgG1 Formulation 5.21 g Coupling Sugar S-containing syrup (equivalent to 4.0 g Coupling Sugar S) and 0.50 g L-isoleucine were dissolved in around 40 ml demineralized water (with a pH of around 7.5) in an ultrasonic bath. As the next step, around 4.60 ml pure IgG1 with a concentration of around 109 mg/ml formulated in a pH 6 glycine-histidine buffer (see Materials) were added and diluted with demineralized water (with a pH of around 7.5) to a volume of 50 ml. The thus obtained solution contained around 9% (w/v) adjuvant or matrix and 1% (w/v) protein and was spray-dried as described above with application of cylone I at an atomizing air flow of around 0.67 $m^3$/h. The aggregate content was investigated as described above.

After one week's open storage at 75% relative air humidity and 40° C. (forced storage stability), the solution prepared from the reconstituted powder had around 6.8% aggregates.

Example 3

Spray Drying of a 3% (w/v) Trehalose 6% (w/v) L-Citrulline 1% (w/v) IgG1 Formulation 1.50 g trehalose and 3.00 g L-citrulline were dissolved in around 40 ml demineralized water (with a pH of around 7.5) in an ultrasonic bath. As the next step, around 4.6 ml pure IgG1 with a concentration of around 109 mg/ml formulated in a pH 6 glycine-histidine buffer (see Materials) were added and diluted with demineralized water (with a pH of around 7.5) to a volume of 50 ml. The thus obtained solution contained around 9% (w/v) adjuvant or matrix and 1% (w/v) protein and was spray-dried as described above with application of cylone I at an atomizing air flow of around 0.67 $m^3$/h. The aggregate content was investigated as described above.

After one week's open storage at 75% relative air humidity and 40° C. (forced storage stability), the solution prepared from the reconstituted powder had around 5.9% aggregates.

Spray Drying of a 3% (w/v) LS55P 6% (w/v) L-Citrulline 1% (w/v) IgG1 Formulation 1.50 g LS55P and 3.00 g L-citrulline were dissolved in around 40 ml demineralized water (with a pH of around 7.5) in an ultrasonic bath. As the next step, around 4.60 ml pure IgG1 with a concentration of around 109 mg/ml formulated in a pH 6 glycine-histidine buffer (see Materials) were added and diluted with demineralized water (with a pH of around 7.5) to a volume of 50 ml. The thus obtained solution contained around 9% (w/v) adjuvant or matrix and 1% (w/v) protein and was spray-dried as described above with application of cylone I at an atomizing air flow of around 0.67 $m^3$/h. The aggregate content was investigated as described above.

After one week's open storage at 75% relative air humidity and 40° C. (forced storage stability), the solution prepared from the reconstituted powder had around 2.9% aggregates.

After one day's equilibration and four weeks' dry storage at 40° C., the solution prepared from the reconstituted powder had around 1.8% aggregates.

After one day's vacuum drying and four weeks' dry storage at 40° C., the solution prepared from the reconstituted powder had around 1.3% aggregates.

Spray Drying of a 3% (w/v) Coupling Sugar 6% L-Citrulline 1% (w/v) IgG1 Formulation 1.91 g Coupling Sugar-containing syrup (equivalent to 1.5 g Coupling Sugar) and 3.00 g L-citrulline were dissolved in around 40 ml demineralized water (with a pH of around 7.5) in an ultrasonic bath. As the next step, around 4.60 ml pure IgG1 with a concentration of around 109 mg/ml formulated in a pH 6 glycine-histidine buffer (see Materials) were added and diluted with demineralized water (with a pH of around 7.5) to a volume of 50 ml. The thus obtained solution contained around 9% (w/v) adjuvant or matrix and 1% (w/v) protein and was spray-dried as described above with application of cylone I at an atomizing air flow of around 0.67 $m^3$/h. The aggregate content was investigated as described above.

After one week's open storage at 75% relative air humidity and 40° C. (forced storage stability), the solution prepared from the reconstituted powder had around 3.9% aggregates.

After one day's equilibration and four weeks' dry storage at 40° C., the solution prepared from the reconstituted powder had around 1.4% aggregates.

After one day's vacuum drying and four weeks' dry storage at 40° C., the solution prepared from the reconstituted powder had around 1.3% aggregates.

Spray Drying of a 3% (w/v) Coupling Sugar S 6% L-Citrulline 1% (w/v) IgG1 Formulation 1.95 g Coupling Sugar S-containing syrup (equivalent to 1.5 g Coupling Sugar S) and 3.00 g L-citrulline were dissolved in around 40 ml demineralized water (with a pH of around 7.5) in an ultrasonic bath. As the next step, around 4.60 ml pure IgG1 with a concentration of around 109 mg/ml formulated in a pH 6 glycine-histidine buffer (see Materials) were added and diluted with demineralized water (with a pH of around 7.5) to a volume of 50 ml. The thus obtained solution contained around 9% (w/v) adjuvant or matrix and 1% (w/v) protein and was spray-dried as described above with application of cylone I at an atomizing air flow of around 0.67 $m^3$/h. The aggregate content was investigated as described above.

After one week's open storage at 75% relative air humidity and 40° C. (forced storage stability), the solution prepared from the reconstituted powder had around 3.1% aggregates.

Example 4

Spray Drying of a 2.66% (w/v) Trehalose 0.33% (w/v) Tri-Isoleucine 0.33% (w/v) IgG1 Formulation 8.0 g trehalose and 1 g tri-isoleucine were dissolved in around 280 ml demineralized water (with a pH of around 7.5) in an ultrasonic bath. As the next step, around 12.30 ml pure IgG1 with a concentration of around 96.55 mg/ml formulated in a pH 6 glycine-histidine buffer (see Materials) were added and diluted with demineralized water (with a pH of around 7.5) to a volume of 300 ml. The thus obtained solution contained around 3% (w/v) adjuvant or matrix and 0.33% (w/v) protein and was spray-dried as described above with application of cylone II at an atomizing air flow of around 0.67 $m^3$/h. The aggregate content was investigated as described above.

After one week's open storage at 75% relative air humidity and 40° C. (forced storage stability), the solution prepared from the reconstituted powder had around 26.7% aggregates.

Spray Drying of a 2.66% (w/v) Raffinose 0.33% (w/v) Tri-Isoleucine 0.33% (w/v) IgG1 Formulation 8.0 g raffinose and 1 g tri-isoleucine were dissolved in around 140 ml demineralized water (with a pH of around 7.5) in an ultrasonic bath. As the next step, around 4.87 ml pure IgG1 with a concentration of around 102.8 mg/ml formulated in a pH 6 glycine-histidine buffer (see Materials) were added and diluted with demineralized water (with a pH of around 7.5) to a volume of 300 ml. The thus obtained solution contained around 3% (w/v) adjuvant or matrix and 0.33% (w/v) protein and was spray-dried as described above with application of cylone II at an atomizing air flow of around 0.67 $m^3$/h. The aggregate content was investigated as described above.

After one week's open storage at 75% relative air humidity and 40° C. (forced storage stability), the solution prepared from the reconstituted powder had around 12.6% aggregates.

Spray Drying of a 2.66% (w/v) Hydroxyethyl Starch (HES) 0.33% (w/v) Tri-Isoleucine 0.33% (w/v) IgG1 Formulation 8.0 g HES and 1 g tri-isoleucine were dissolved in around 140 ml demineralized water (with a pH of around 7.5) in an ultrasonic bath at around 80° C. with stirring. As the next step, around 4.87 ml pure IgG1 with a concentration of around 102.8 mg/ml formulated in a pH 6 glycine-histidine buffer (see Materials) were added to the previously refrigerated turbid solution and diluted with demineralized water (with a pH of around 7.5) to a volume of 150 ml. The thus obtained solution contained around 3% (w/v) adjuvant or matrix and 0.33% (w/v) protein and was spray-dried as described above with application of cylone II at an atomizing air flow of around 0.67 $m^3$/h. The aggregate content was investigated as described above.

After one week's open storage at 75% relative air humidity and 40° C. (forced storage stability), the solution prepared from the reconstituted powder had around 18.6% aggregates.

After 1 and 3 months' open storage at around 43% relative air humidity and 25° C. (open 3 months' stability), the solution prepared from the reconstituted powder had around 11.9% and 15.4% aggregates respectively.

Spray Drying of a 2.00% (w/v) Saccharose 0.66% (w/v) Lactose 0.33% (w/v) Tri-Isoleucine 0.33% (w/v) IgG1 Formulation 6.0 g saccharose, 2.0 g lactose, and 1 g tri-isoleucine were dissolved in around 280 ml demineralized water (with a pH of around 7.5) in an ultrasonic bath. As the next step, around 9.73 ml pure IgG1 with a concentration of around 102.8 mg/ml formulated in a pH 6 glycine-histidine buffer (see Materials) were added and diluted with demineralized water (with a pH of around 7.5) to a volume of 300 ml. The thus obtained solution contained around 3% (w/v) adjuvant or matrix and 0.33% (w/v) protein and was spray-dried as described above with application of cylone II at an atomizing air flow of around 0.67 $m^3$/h. The aggregate content was investigated as described above.

After one week's open storage at 75% relative air humidity and 40° C. (forced storage stability), the solution prepared from the reconstituted powder had around 8.8% aggregates.

Spray Drying of a 2.66% (w/v) Saccharose 0.33% (w/v) Tri-Isoleucine 0.33% (w/v) IgG1 Formulation 8.0 g saccharose and 1 g tri-isoleucine were dissolved in around 280 ml demineralized water (with a pH of around 7.5) in an ultrasonic bath. As the next step, around 9.73 ml pure IgG1 with a concentration of around 102.8 mg/ml formulated in a pH 6 glycine-histidine buffer (see Materials) were added and diluted with demineralized water (with a pH of around 7.5) to a volume of 300 ml. The thus obtained solution contained around 3% (w/v) adjuvant or matrix and 0.33% (w/v) protein and was spray-dried as described above with application of cylone II at an atomizing air flow of around 0.67 m³/h. The aggregate content was investigated as described above.

After one week's open storage at 75% relative air humidity and 40° C. (forced storage stability), the solution prepared from the reconstituted powder had around 5.6% aggregates.

Spray Drying of a 2.66% (w/v) LS90P 0.33% (w/v) Tri-Isoleucine 0.33% (w/v) IgG1 Formulation 4.0 g LS90P and 0.50 g tri-isoleucine were dissolved in around 140 ml demineralized water (with a pH of around 7.5). As the next step, around 4.864 ml pure IgG1 with a concentration of around 102.8 mg/ml formulated in a pH 6 glycine-histidine buffer (see Materials) were added and diluted with demineralized water (with a pH of around 7.5) to a volume of 150 ml. The thus obtained solution contained around 3.00% (w/v) adjuvant or matrix and 0.33% (w/v) protein and was spray-dried as described above with application of cylone II at an atomizing air flow of around 0.67 m³/h. The aggregate content was investigated as described above.

The following aggregate contents were obtained for its storage stability:

After one week's open storage at 75% relative air humidity and 40° C. (forced storage stability), the solution prepared from the reconstituted powder had around 2.3% aggregates.

After 1 and 3 months' storage at 2-8° C. (3 months' stability), the solution prepared from the reconstituted powder had around 0.7% and 1.0% aggregates respectively.

After 1 and 3 months' storage at 25° C. (3 months' stability), the solution prepared from the reconstituted powder had around 0.8% and 1.4% aggregates respectively.

After 1 and 3 months' storage at 40° C. (3 months' stability), the solution prepared from the reconstituted powder had around 0.9% and 2.2% aggregates respectively.

After 1 and 3 months' open storage at around 29% relative air humidity and 25° C., the solution prepared from the reconstituted powder had around 0.4% and 0.7% aggregates respectively.

After 1 and 3 months' open storage at around 43% relative air humidity and 25° C., the solution prepared from the reconstituted powder had around 0.5% and 0.6% aggregates respectively.

The MMD of the powder was determined as described above.

The MMD of the powder after spray drying was 4.7 μm.

The MMAD and FPF of the powder were determined as described above.

The MMAD of the powder after spray drying was 4.8 μm, and the FPF was 53.2% in relation to the powder capsule weight.

Spray Drying of a 2.66% (w/v) LS90P 0.33% (w/v) Tri-Isoleucine 0.33% (w/v) IgG1 Formulation 4.0 g LS90P and 0.50 g tri-isoleucine were dissolved in around 140 ml demineralized water (with a pH of around 7.5). As the next step, around 4.864 ml pure IgG1 with a concentration of around 102.8 mg/ml formulated in a pH 6 glycine-histidine buffer (see Materials) were added and diluted with demineralized water (with a pH of around 7.5) to a volume of 150 ml. The thus obtained solution contained around 3.00% (w/v) adjuvant or matrix and 0.33% (w/v) protein and was spray-dried as described above with application of cylone II at an atomizing air flow of around 1.05 m³/h. The aggregate content was investigated as described above.

The following aggregate contents were obtained for its storage stability:

After one week's open storage at 75% relative air humidity and 40° C. (forced storage stability), the solution prepared from the reconstituted powder had around 2.2% aggregates.

After 1 and 3 months' storage at around 29% relative air humidity and 25° C. (open 3 months' stability), the solution prepared from the reconstituted powder had around 0.5% and 0.6% aggregates respectively.

After 1 and 3 months' storage at around 43% relative air humidity and 25° C. (open 3 months' stability), the solution prepared from the reconstituted powder had around 0.5% and 0.7% aggregates respectively.

The MMD of the powder was determined as described above.

The MMD of the powder after spray drying was 2.7 μm.

The MMAD and FPF of the powder were determined as described above.

The MMAD of the powder after spray drying was 3.6 μm, and the FPF was 58.0% in relation to the powder capsule weight.

Spray Drying of a 2.66% (w/v) LS90P 0.33% (w/v) Tri-Isoleucine 0.33% (w/v) IgG1 Formulation 4.0 g LS90P and 0.50 g tri-isoleucine were dissolved in around 140 ml demineralized water (with a pH of around 7.5). As the next step, around 4.864 ml pure IgG1 with a concentration of around 102.8 mg/ml formulated in a pH 6 glycine-histidine buffer (see Materials) were added and diluted with demineralized water (with a pH of around 7.5) to a volume of 150 ml. The thus obtained solution contained around 3.00% (w/v) adjuvant or matrix and 0.33% (w/v) protein and was spray-dried as described above with application of cylone II at an atomizing air flow of around 1.74 m³/h. The aggregate content was investigated as described above.

The following aggregate contents were obtained for its storage stability:

After one week's open storage at 75% relative air humidity and 40° C. (forced storage stability), the solution prepared from the reconstituted powder had around % aggregates.

After 1 and 3 months' storage at around 29% relative air humidity and 25° C. (open 3 months' stability), the solution prepared from the reconstituted powder had around 0.5% and 0.6% aggregates respectively.

After 1 and 3 months' storage at around 43% relative air humidity and 25° C. (open 3 months' stability), the solution prepared from the reconstituted powder had around 0.5% and 0.8% aggregates respectively.

The MMD of the powder was determined as described above.

The MMD of the powder after spray drying was 2.6 μm.

The MMAD and FPF of the powder were determined as described above.

The MMAD of the powder after spray drying was 3.3 μm, and the FPF was 58.9% in relation to the powder capsule weight.

Spray Drying of a 1.60% (w/v) LS90P 0.20% (w/v) Tri-Isoleucine 0.20% (w/v) IgG1 Formulation 4.0 g LS90P and 0.50 g tri-isoleucine were dissolved in around 220 ml demineralized water (with a pH of around 7.5). As the next step, around 4.864 ml pure IgG1 with a concentration of around 102.8 mg/ml formulated in a pH 6 glycine-histidine buffer (see Materials) were added and diluted with demineralized water (with a pH of around 7.5) to a volume of 250 ml. The thus obtained solution contained around 1.80% (w/v) adjuvant or matrix and 0.20% (w/v) protein and was spray-dried as described above with application of cylone II at an atomizing air flow of around 0.67 m$^3$/h. The aggregate content was investigated as described above.

The following aggregate contents were obtained for its storage stability:
  After one week's open storage at 75% relative air humidity and 40° C. (forced storage stability), the solution prepared from the reconstituted powder had around 2.2% aggregates.
  After 1 and 3 months' storage at around 29% relative air humidity and 25° C. (open 3 months' stability), the solution prepared from the reconstituted powder had around 0.5% and 0.5% aggregates respectively.
  After 1 and 3 months' storage at around 43% relative air humidity and 25° C. (open 3 months' stability), the solution prepared from the reconstituted powder had around 0.7% and 0.7% aggregates respectively.

The MMD of the powder was determined as described above.

The MMD of the powder after spray drying was 3.2 μm.

The MMAD and FPF of the powder were determined as described above.

The MMAD of the powder after spray drying was 3.9 μm, and the FPF was 55.6% in relation to the powder capsule weight.

Spray Drying of a 2.833% (w/v) LS90P 0.166% (w/v) Tri-Isoleucine 0.33% (w/v) IgG1 Formulation 4.25 g LS90P and 0.25 g tri-isoleucine were dissolved in around 140 ml demineralized water (with a pH of around 7.5). As the next step, around 4.864 ml pure IgG1 with a concentration of around 102.8 mg/ml formulated in a pH 6 glycine-histidine buffer (see Materials) were added and diluted with demineralized water (with a pH of around 7.5) to a volume of 150 ml. The thus obtained solution contained around 3.00% (w/v) adjuvant or matrix and 0.33% (w/v) protein and was spray-dried as described above with application of cylone II at an atomizing air flow of around 0.67 m$^3$/h. The aggregate content was investigated as described above.

The following aggregate contents were obtained for its storage stability:
  After one week's open storage at 75% relative air humidity and 40° C. (forced storage stability), the solution prepared from the reconstituted powder had around 1.5% aggregates.
  After 1 and 3 months' storage at around 29% relative air humidity and 25° C. (open 3 months' stability), the solution prepared from the reconstituted powder had around 0.5% and 0.5% aggregates respectively.
  After 1 and 3 months' storage at around 43% relative air humidity and 25° C. (open 3 months' stability), the solution prepared from the reconstituted powder had around 0.5% and 0.6% aggregates respectively.

The MMD of the powder was determined as described above.

The MMD of the powder after spray drying was 4.8 μm.

The MMAD and FPF of the powder were determined as described above.

The MMAD of the powder after spray drying was 5.2 μm, and the FPF was 45.7% in relation to the powder capsule weight.

Spray Drying of a 2.9166% (w/v) LS90P 0.0833% (w/v) Tri-Isoleucine 0.33% (w/v) IgG1 Formulation 4.375 g LS90P and 0.125 g tri-isoleucine were dissolved in around 140 ml demineralized water (with a pH of around 7.5). As the next step, around 4.864 ml pure IgG1 with a concentration of around 102.8 mg/ml formulated in a pH 6 glycine-histidine buffer (see Materials) were added and diluted with demineralized water (with a pH of around 7.5) to a volume of 150 ml. The thus obtained solution contained around 3.00% (w/v) adjuvant or matrix and 0.33% (w/v) protein and was spray-dried as described above with application of cylone II at an atomizing air flow of around 0.67 m$^3$/h. The aggregate content was investigated as described above.

The following aggregate contents were obtained for its storage stability:
  After one week's open storage at 75% relative air humidity and 40° C. (forced storage stability), the solution prepared from the reconstituted powder had around 1.2% aggregates.
  After 1 and 3 months' storage at around 29% relative air humidity and 25° C. (open 3 months' stability), the solution prepared from the reconstituted powder had around 0.4% and 0.5% aggregates respectively.
  After 1 and 3 months' storage at around 43% relative air humidity and 25° C. (open 3 months' stability), the solution prepared from the reconstituted powder had around 0.5% and 0.6% aggregates respectively.

The MMD of the powder was determined as described above.

The MMD of the powder after spray drying was 4.2 μm.

The MMAD and FPF of the powder were determined as described above.

The MMAD of the powder after spray drying was 6.1 μm, and the FPF was 39.6% in relation to the powder capsule weight.

Spray Drying of a 2.66% (w/v) LS55P 0.33% (w/v) Tri-Isoleucine 0.33% (w/v) IgG1 Formulation 8.0 g LS55P and 1 g tri-isoleucine were dissolved in around 280 ml demineralized water (with a pH of around 7.5) in an ultrasonic bath. As the next step, around 9.73 ml pure IgG1 with a concentration of around 102.8 mg/ml formulated in a pH 6 glycine-histidine buffer (see Materials) were added and diluted with demineralized water (with a pH of around 7.5) to a volume of 300 ml. The thus obtained solution contained around 3% (w/v) adjuvant or matrix and 0.33% (w/v) protein and was spray-dried as described above with application of cylone II at an atomizing air flow of around 0.67 m$^3$/h. The aggregate content was investigated as described above.

After one week's open storage at 75% relative air humidity and 40° C. (forced storage stability), the solution prepared from the reconstituted powder had around 2.1% aggregates.

After 1 and 3 months' storage at 2-8° C. (3 months' stability), the solution prepared from the reconstituted powder had around 0.8% and 1.5% aggregates respectively.

After 1 and 3 months' storage at 25° C. (3 months' stability), the solution prepared from the reconstituted powder had around 0.9% and 1.5% aggregates respectively.

After 1 and 3 months' storage at 40° C. (3 months' stability), the solution prepared from the reconstituted powder had around 1.3% and 2.6% aggregates respectively.

After 1 and 3 months' storage at around 43% relative air humidity and 25° C. (open 3 months' stability), the solution prepared from the reconstituted powder had around 1.0% and 1.0% aggregates respectively.

The MMD of the powder was determined as described above.

The MMD of the powder after spray drying was 3.4 µm.

The MMAD and FPF of the powder were determined as described above.

The MMAD of the powder after spray drying was 3.9 µm, and the FPF was 58.3% in relation to the powder capsule weight.

After one month's storage at around 43% relative air humidity and 25° C. (open 3 months' stability), the MMAD was 3.8 µm, and the FPF was 59.6% in relation to the powder capsule weight.

Spray Drying of a 2.833% (w/v) LS55P 0.166% (w/v) Tri-Isoleucine 0.33% (w/v) IgG1 Formulation 8.5 g LS90P and 0.5 g tri-isoleucine were dissolved in around 280 ml demineralized water (with a pH of around 7.5) in an ultrasonic bath. As the next step, around 9.73 ml pure IgG1 with a concentration of around 102.8 mg/ml formulated in a pH 6 glycine-histidine buffer (see Materials) were added and diluted with demineralized water (with a pH of around 7.5) to a volume of 300 ml. The thus obtained solution contained around 3% (w/v) adjuvant or matrix and 0.33% (w/v) protein and was spray-dried as described above with application of cylone II at an atomizing air flow of around 0.67 m³/h. The aggregate content was investigated as described above.

After one week's open storage at 75% relative air humidity and 40° C. (forced storage stability), the solution prepared from the reconstituted powder had around 3.4% aggregates.

After 1 and 3 months' storage at around 43% relative air humidity and 25° C. (open 3 months' stability), the solution prepared from the reconstituted powder had around 1.3% and 1.5% aggregates respectively.

The MMD of the powder was determined as described above.

The MMD of the powder after spray drying was 2.9 µm.

The MMAD and FPF of the powder were determined as described above.

The MMAD of the powder after spray drying was 4.4 µm, and the FPF was 58.6% in relation to the powder capsule weight.

Spray Drying of a 2.9166% (w/v) LS55P 0.0833% (w/v) Tri-Isoleucine 0.33% (w/v) IgG1 Formulation 8.75 g LS90P and 0.25 g tri-isoleucine were dissolved in around 280 ml demineralized water (with a pH of around 7.5). As the next step, around 9.73 ml pure IgG1 with a concentration of around 102.8 mg/ml formulated in a pH 6 glycine-histidine buffer (see Materials) were added and diluted with demineralized water (with a pH of around 7.5) to a volume of 300 ml. The thus obtained solution contained around 3% (w/v) adjuvant or matrix and 0.33% (w/v) protein and was spray-dried as described above with application of cylone II at an atomizing air flow of around 0.67 m³/h. The aggregate content was investigated as described above.

After one week's open storage at 75% relative air humidity and 40° C. (forced storage stability), the solution prepared from the reconstituted powder had around 4.4% aggregates.

After 1 and 3 months' storage at around 43% relative air humidity and 25° C. (open 3 months' stability), the solution prepared from the reconstituted powder had around 0.7% and 0.8% aggregates respectively.

The MMD of the powder was determined as described above.

The MMD of the powder after spray drying was 2.9 µm.

The MMAD and FPF of the powder were determined as described above.

The MMAD of the powder after spray drying was 4.4 µm, and the FPF was 58.6% in relation to the powder capsule weight.

Example 5

Production of Further Powders According to the Invention

Spray Drying of a 3.33% (w/v) Lysozyme Formulation 5 g lysozyme were dissolved in around 140 ml demineralized water (with a pH of around 7.5) and diluted with demineralized water (with a pH of around 7.5) to a volume of 150 ml. The thus obtained solution was spray-dried as described above with application of cylone II.

The residual monomer content was determined as described above. After forced storage, the solution prepared from the reconstituted powder had a residual monomer content of 35.3%. The MMD of the powder was determined as described above. The MMD of the powder was 3.2 µm. The MMAD and FPF of the powder were determined as described above. The MMAD was 4.0 µm, and the FPF was 70.4% in relation to the powder capsule weight.

Spray Drying of a 3.00% (w/v) LS90P 0.33% (w/v) Lysozyme Formulation 9.0 g LS90P were dissolved in around 280 ml demineralized water (with a pH of around 7.5) in an ultrasonic bath. As the next step, 1 g lysozyme was added and diluted with demineralized water (with a pH of around 7.5) to a volume of 300 ml. The thus obtained solution was spray-dried as described above with application of cylone II.

The residual monomer content was determined as described above. After forced storage, the solution prepared from the reconstituted powder had a residual monomer content of 62.1%. The MMD of the powder was determined as described above. The MMD of the powder was 4.0 µm. The MMAD and FPF of the powder were determined as described above. The MMAD was 3.7 µm, and the FPF was 24.7% in relation to the powder capsule weight.

Spray Drying of a 2.66% (w/v) LS90P 0.33% (w/v) Isoleucine 0.33% (w/v) Lysozyme Formulation 8.0 g LS90P and 1 g isoleucine were dissolved in around 280 ml demineralized water (with a pH of around 7.5) in an ultrasonic bath. As the next step, 1 g lysozyme was added and diluted with demineralized water (with a pH of around 7.5) to a volume of 300 ml. The thus obtained solution was spray-dried as described above with application of cylone II.

The residual monomer content was determined as described above. After forced storage, the solution prepared from the reconstituted powder had a residual monomer content of 47.9%. The MMD of the powder was determined as described above. The MMD of the powder was 3.9 µm. The MMAD and FPF of the powder were determined as described above. The MMAD was 4.1 µm, and the FPF was 29.0% in relation to the powder capsule weight.

Spray Drying of a 2.66% (w/v) LS90P 0.33% (w/v) Tri-Isoleucine 0.33% (w/v) Lysozyme Formulation 8.0 g LS90P and 1 g tri-isoleucine were dissolved in around 280 ml demineralized water (with a pH of around 7.5) in an ultrasonic bath. As the next step, 1 g lysozyme was added and diluted with demineralized water (with a pH of around 7.5) to a volume of 300 ml. The thus obtained solution was spray-dried as described above with application of cylone II.

The residual monomer content was determined as described above. After forced storage, the solution prepared from the reconstituted powder had a residual monomer content of 47.9%. The MMD of the powder was determined as described above. The MMD of the powder was 2.7 µm. The MMAD and FPF of the powder were determined as described above. The MMAD was 3.6 µm, and the FPF was 58.6% in relation to the powder capsule weight.

Spray Drying of a 3.33% (w/v) Calcitonin Formulation 1 g calcitonin was dissolved in around 25 ml demineralized water (with a pH of around 7.5) and diluted with demineralized water (with a pH of around 7.5) to a volume of 30 ml. The thus obtained solution was spray-dried as described above with application of cylone II.

The aggregate content was investigated as described above.

After 3 months' storage at 2-8° C. (3 months' stability), the solution prepared from the reconstituted powder had around 4.1% aggregates respectively.

After 3 months' storage at 25° C. (3 months' stability), the solution prepared from the reconstituted powder had around 4.9% aggregates respectively.

After 3 months' storage at 40° C. (3 months' stability), the solution prepared from the reconstituted powder had around 7.4% aggregates respectively.

The MMAD and FPF of the powder were determined as described above. The MMAD was 3.9 µm, and the FPF was 59.0% in relation to the powder capsule weight.

Spray Drying of a 3.166% (w/v) LS90P 0.166% (w/v) Calcitonin Formulation 4.750 g LS90P were dissolved in around 140 ml demineralized water (with a pH of around 7.5). As the next step, 0.250 g calcitonin was added and diluted with demineralized water (with a pH of around 7.5) to a volume of 150 ml. The thus obtained solution was spray-dried as described above with application of cylone II.

The aggregate content was investigated as described above.

After 3 months' storage at 2-8° C. (3 months' stability), the solution prepared from the reconstituted powder had around 3.6% aggregates respectively.

After 3 months' storage at 25° C. (3 months' stability), the solution prepared from the reconstituted powder had around 3.9% aggregates respectively.

After 3 months' storage at 40° C. (3 months' stability), the solution prepared from the reconstituted powder had around 4.6% aggregates respectively.

The MMD of the powder was determined as described above. The MMD of the powder was 2.6 µm. The MMAD and FPF of the powder were determined as described above. The MMAD was 4.3 µm, and the FPF was 47.3% in relation to the powder capsule weight.

Spray Drying of a 2.833% (w/v) LS90P 0.33% (w/v) Isoleucine 0.166% (w/v) Calcitonin Formulation 4.250 g LS90P and 0.50 g isoleucine were dissolved in around 140 ml demineralized water (with a pH of around 7.5) in an ultrasonic bath. As the next step, 0.250 g calcitonin was added and diluted with demineralized water (with a pH of around 7.5) to a volume of 150 ml. The thus obtained solution was spray-dried as described above with application of cylone II.

The aggregate content was investigated as described above.

After 3 months' storage at 2-8° C. (3 months' stability), the solution prepared from the reconstituted powder had around 3.3% aggregates respectively.

After 3 months' storage at 25° C. (3 months' stability), the solution prepared from the reconstituted powder had around 3.6% aggregates respectively.

After 3 months' storage at 40° C. (3 months' stability), the solution prepared from the reconstituted powder had around 3.6% aggregates respectively.

The MMD of the powder was determined as described above. The MMD of the powder was 2.8 µm. The MMAD and FPF of the powder were determined as described above. The MMAD was 4.4 µm, and the FPF was 49.2% in relation to the powder capsule weight.

Spray Drying of a 2.866% (w/v) LS90P 0.33% (w/v) Tri-Isoleucine 0.166% (w/v) Calcitonin Formulation 4.250 g LS90P and 0.50 g tri-isoleucine were dissolved in around 140 ml demineralized water (with a pH of around 7.5) in an ultrasonic bath. As the next step, 0.250 g calcitonin was added and diluted with demineralized water (with a pH of around 7.5) to a volume of 150 ml. The thus obtained solution was spray-dried as described above with application of cylone II.

The aggregate content was investigated as described above.

After 3 months' storage at 2-8° C. (3 months' stability), the solution prepared from the reconstituted powder had around 3.3% aggregates respectively.

After 3 months' storage at 25° C. (3 months' stability), the solution prepared from the reconstituted powder had around 3.6% aggregates respectively.

After 3 months' storage at 40° C. (3 months' stability), the solution prepared from the reconstituted powder had around 3.9% aggregates respectively.

The MMD of the powder was determined as described above. The MMD of the powder was 2.5 µm. The MMAD and FPF of the powder were determined as described above. The MMAD was 3.5 µm, and the FPF was 60.4% in relation to the powder capsule weight.

Example 6

Freeze Drying of a 5% (w/v) IgG1 Formulation

Pure IgG1 with a concentration of around 109 mg/ml formulated in a pH 6 glycine-histidine buffer (see Materials) was diluted with demineralized water (with a pH of around 7.5) to a content of 50 mg/ml and freeze-dried in the absence of any other adjuvants. The solution had a volume of 50 ml and was distributed in commercial 2R vials before freeze drying. The lyophilisate was lyophilised in the 2R vials by means of a spatula and further treated as described above.

The aggregate content was investigated as described above.

After one week's open storage at 75% relative air humidity and 40° C. (forced storage stability), the solution prepared from the reconstituted powder had around 20.5% aggregates.

After one day's equilibration and four weeks' dry storage at 40° C., the solution prepared from the reconstituted powder had around 15.3% aggregates.

After one day's vacuum drying and four weeks' dry storage at 40° C., the solution prepared from the reconstituted powder had around 12.6% aggregates.

Freeze Drying of a 4.5% (w/v) Mannitol 0.5% (w/v) IgG1 Formulation 2.25 g mannitol were dissolved in around 40 ml demineralized water (with a pH of around 7.5). As the next step, 2.3 ml pure IgG1 with a concentration of around 109 mg/ml formulated in a pH 6 glycine-histidine buffer (see Materials) was diluted with demineralized water (with a pH of around 7.5) to a content of 50 mg/ml. The thus obtained solution contained around 4.5% (w/v) adjuvant or matrix and 0.5% (w/v) protein, was distributed in commercial 2R vials, and was freeze-dried as described above. The lyophilisate was lyophilised in the 2R vials by means of a spatula and further treated as described above. The aggregate content was investigated as described above.

The following aggregate contents were obtained for its storage stability:

After one week's open storage at 75% relative air humidity and 40° C. (forced storage stability), the solution prepared from the reconstituted powder had around 34.0% aggregates.

After one day's equilibration and four weeks' dry storage at 40° C., the solution prepared from the reconstituted powder had around 11.6% aggregates.

After one day's vacuum drying and four weeks' dry storage at 40° C., the solution prepared from the reconstituted powder had around 6.2% aggregates.

Freeze Drying of a 4.5% (w/v) LS55P 0.5% (w/v) IgG1 Formulation 2.25 g LS55P were dissolved in around 40 ml demineralized water (with a pH of around 7.5). As the next step, 2.3 ml pure IgG1 with a concentration of around 109 mg/ml formulated in a pH 6 glycine-histidine buffer (see Materials) was diluted with demineralized water (with a pH of around 7.5) to a content of 50 mg/ml. The thus obtained solution contained around 4.5% (w/v) adjuvant or matrix and 0.5% (w/v) protein, was distributed in commercial 2R vials, and was freeze-dried as described above.

The lyophilisate was lyophilised in the 2R vials by means of a spatula and further treated as described above. The aggregate content was investigated as described above.

The following aggregate contents were obtained for its storage stability:

After one week's open storage at 75% relative air humidity and 40° C. (forced storage stability), the solution prepared from the reconstituted powder had around 2.5% aggregates.

After one day's equilibration and four weeks' dry storage at 40° C., the solution prepared from the reconstituted powder had around 2.6% aggregates.

After one day's vacuum drying and four weeks' dry storage at 40° C., the solution prepared from the reconstituted powder had around 1.2% aggregates.

Freeze Drying of a 4.5% (w/v) Coupling Sugar 0.5% (w/v) IgG1 Formulation 2.25 g Coupling Sugar were dissolved in around 40 ml demineralized water (with a pH of around 7.5). As the next step, 2.3 ml pure IgG1 with a concentration of around 109 mg/ml formulated in a pH 6 glycine-histidine buffer (see Materials) was diluted with demineralized water (with a pH of around 7.5) to a content of 50 mg/ml. The thus obtained solution contained around 4.5% (w/v) adjuvant or matrix and 0.5% (w/v) protein, was distributed in commercial 2R vials, and was freeze-dried as described above. The lyophilisate was lyophilised in the 2R vials by means of a spatula and further treated as described above. The aggregate content was investigated as described above.

The following aggregate contents were obtained for its storage stability:

After one week's open storage at 75% relative air humidity and 40° C. (forced storage stability), the solution prepared from the reconstituted powder had around 5.5% aggregates.

After one day's equilibration and four weeks' dry storage at 40° C., the solution prepared from the reconstituted powder had around 4.6% aggregates.

After one day's vacuum drying and four weeks' dry storage at 40° C., the solution prepared from the reconstituted powder had around 1.5% aggregates.

The invention claimed is:

1. A composition for pharmaceutical use comprising at least one antibody or one derivative thereof and a sugar fraction comprising:
    a) one or more 1,4 O-linked saccharose derivatives selected from the group consisting of 1,4 O-linked D-Gal-saccharose (lactosucrose), 1,4 O-linked D-Glu-saccharose (glucosyl sucrose), and 1,4 O-linked Glu-Glu-saccharose (maltosyl sucrose); and
    b) one or more mono-, di, and/or polysaccharides.

2. The composition according to claim 1, which contains lactosucrose as the 1,4 O-linked saccharose derivative.

3. The composition according to claim 2, wherein b) of said sugar fraction comprises lactose and saccharose.

4. The composition according to any one of claims 2 or 3, wherein lactosucrose amounts to at least 55% (w/w) in relation to the sugar fraction contained in the composition.

5. The composition according to claim 1, wherein a) of said sugar fraction comprises a mixture of glucosyl sucrose and maltosyl sucrose.

6. The composition according to claim 5, wherein b) of said sugar fraction of the composition comprises fructose, glucose, and/or saccharose.

7. The composition according to any one of claims 5 or 6, wherein the total amount of glucosyl sucrose and maltosyl sucrose is at least 25% (w/w) in relation to the sugar fraction contained in the composition.

8. The composition according to any one of claims 5 or 6, wherein each of the respective amounts of glucosyl sucrose and maltosyl sucrose is at least 18% (w/w) in relation to the sugar fraction contained in the composition.

9. The composition according to claim 1, wherein the sugar fraction amounts to between 25 and 99.99% (w/w) of the dry weight of the composition.

10. The composition according to claim 1, wherein the weight of antibody or antibody derivative amounts to between 0.1 and 75% (w/w) of the dry weight of the composition, and that the sum of the weight percentages of said sugar fraction and said antibody or antibody derivative amounts to max 100% (w/w).

11. The composition according to claim 1, wherein the dry weight of the composition contains between 60 and 90% (w/w) of said sugar fraction, and up to 40% (w/w) of an antibody or antibody derivative, wherein lactosucrose, maltosyl sucrose, and/or glucosyl sucrose amounts to at least 20% (w/w) of the dry weight of the composition, and the sum of the weight percentages of said sugar fraction and said antibody or antibody derivative amounts to max 100% (w/w).

12. The composition according to claim 1, which further comprises one or more pharmaceutically compatible adjuvants and/or one or more salts.

13. The composition according to claim 12, wherein the adjuvant is an amino acid or peptide.

14. The composition according to claim 13, wherein the amino acid is isoleucine.

15. The composition according to claim 13, wherein the peptide is a di- or tri-peptide.

16. The composition according to claim 13, wherein the peptide is an isoleucine-containing peptide.

17. The composition according to any one of claims 15 or 16, wherein the peptide is di- or tri-isoleucine.

18. The composition according to claim 14, wherein the dry weight of the composition contains between 60 and 99% (w/w) of said sugar fraction, and between 1 and 40% (w/w) isoleucine.

19. The composition according to claim 13, wherein the dry weight of the composition contains between 60 and 99% (w/w) of said sugar fraction, and between 1 and 40% (w/w) of said peptide.

20. The composition according to claim 19, wherein the composition refers to an aqueous solution, semi-solid preparation, or powder.

21. The composition according to claim 20, wherein the composition is in the form of a powder having particles having MMD between 1 and 10 μm.

22. The composition according to claim 20, wherein the composition is in the form of a powder having particles having a MMAD between 1 and 5 μm.

23. A process for production of a powder for pharmaceutical use comprising:
    a) suspending or dissolving an antibody or antibody derivative in an aqueous solution/suspension;
    b) suspending or dissolving in an aqueous solution/suspension a sugar fraction comprising one or more 1,4 O-linked saccharose derivatives selected from the group consisting of lactosucrose, glucosyl sucrose and maltosyl sucrose;
    c) mixing said antibody or antibody derivative and said sugar fraction if they are dissolved/suspended in different solutions/suspensions; and
    d) drying the solution/suspension containing the antibody or antibody derivative and the sugar fraction.

24. The process according to claim 23, wherein the drying process refers to freeze or spray drying.

25. The process according to claim 24, wherein the 1,4 O-linked saccharose derivative is lactosucrose.

26. The process according to claim 25, wherein the solution or suspension further comprises one or more mono-, di, or polysaccharides within said sugar fraction.

27. The process according to claim 26, wherein the solution to be dried additionally contains lactose and saccharose within said sugar fraction.

28. The process according to any one of claims 25 to 27, wherein lactosucrose amounts to at least 55% (w/w) of the sugar fraction present in the solution to be dried.

29. The process according to claim 23 wherein the 1,4 O-linked saccharose derivative is a mixture of glucosyl sucrose and maltosyl sucrose.

30. The process according to claim 29, wherein the solution to be dried additionally contains one or more mono-, di, or polysaccharides within said sugar fraction.

31. The process according to claim 29, wherein the solution to be dried contains fructose, saccharose, and/or glucose within said sugar fraction.

32. The process according to claim 29, wherein the total amount of glucosyl sucrose and maltosyl sucrose is at least 25% (w/w) of that present in the solution to be dried.

33. The process according to claim 29, wherein each of the respective fractions of glucosyl sucrose and maltosyl sucrose amounts to at least 18% (w/w) of that present in the solution to be dried.

34. The process according to claim 23, wherein the sugar fraction amounts to between 25 and 99.99% (w/w) of the dry weight of the solution to be dried.

35. The process according to claim 23, wherein the fraction of antibody or antibody derivative amounts to between 0.1 and 75% (w/w) of the dry weight of the solution to be dried, whereby the sum of the weight percentages of said sugar fraction and said antibody or antibody derivative amounts to max 100% (w/w).

36. The process according to claim 23, wherein the solution to be dried further comprises one or more pharmaceutically compatible adjuvants and/or one or more salts.

37. The process according to claim 36, wherein the adjuvant refers to an amino acid or peptide.

38. The process according to claim 37, wherein the amino acid refers to isoleucine.

39. The process according to claim 37, wherein the peptide refers to a di- or tri-peptide.

40. The process according to claim 37, wherein the peptide refers to an isoleucine-containing peptide.

41. The process according to claim 40, wherein the peptide refers to tri-isoleucine.

42. The process according to claim 37, wherein the dry weight of the solution to be dried contains between 60 and 90% (w/w) of said sugar fraction and between 1 and 19.99% (w/w) amino acid, and the sum of the weight percentages of said sugar fraction and said antibody or antibody derivative amounts to max 100% (w/w).

43. The process according to claim 37 wherein the dry weight of the solution to be dried contains between 60 and 90% (w/w) of said sugar fraction and between 1 and 19.99% of a peptide.

* * * * *

UNITED STATES PATENT AND TRADEMARK OFFICE
CERTIFICATE OF CORRECTION

PATENT NO. : 7,611,709 B2  Page 1 of 1
APPLICATION NO. : 11/120300
DATED : November 3, 2009
INVENTOR(S) : Bassarab et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 511 days.

Signed and Sealed this

Twelfth Day of October, 2010

David J. Kappos
*Director of the United States Patent and Trademark Office*